(12) United States Patent
Nayfach-Battilana

(10) Patent No.: US 8,565,892 B2
(45) Date of Patent: Oct. 22, 2013

(54) NANOPARTICLE-SIZED MAGNETIC ABSORPTION ENHANCERS HAVING THREE-DIMENSIONAL GEOMETRIES ADAPTED FOR IMPROVED DIAGNOSTICS AND HYPERTHERMIC TREATMENT

(75) Inventor: Joseph N. Nayfach-Battilana, San Rafael, CA (US)

(73) Assignee: Qteris, Inc., San Rafael, CA (US)

( * ) Notice: Subject to any disclaimer, the term of this patent is extended or adjusted under 35 U.S.C. 154(b) by 115 days.

(21) Appl. No.: 12/925,904

(22) Filed: Nov. 1, 2010

(65) Prior Publication Data

US 2011/0105825 A1    May 5, 2011

Related U.S. Application Data

(60) Provisional application No. 61/256,986, filed on Oct. 31, 2009.

(51) Int. Cl.
- *A61F 2/00* (2006.01)
- *A61F 7/00* (2006.01)
- *A61F 7/12* (2006.01)
- *G01N 33/553* (2006.01)
- *A61M 37/00* (2006.01)

(52) U.S. Cl.
USPC ............ 607/103; 600/12; 436/526; 977/904; 607/96

(58) Field of Classification Search
USPC ................. 607/96, 103; 600/9–15; 436/526; 977/904
See application file for complete search history.

(56) References Cited

U.S. PATENT DOCUMENTS

| | | |
|---|---|---|
| 4,106,488 A | 8/1978 | Gordon et al. |
| 4,303,636 A | 12/1981 | Gordon et al. |

(Continued)

FOREIGN PATENT DOCUMENTS

| | | |
|---|---|---|
| EP | 0040512 | 11/1981 |
| EP | 0136530 A1 | 6/1988 |

(Continued)

OTHER PUBLICATIONS

Cardinal, et al., Non-invasive radiowave ablation of cancer targeted by gold nanoparticles, Journal of Surgery, 144(2):125-132, 2008.

(Continued)

*Primary Examiner* — Linda Dvorak
*Assistant Examiner* — Jared W Pike
(74) *Attorney, Agent, or Firm* — Marek Alboszta

(57) ABSTRACT

Nanoparticle-sized magnetic absorption enhancers (MAEs) that exhibit a controlled response to a magnetic field, including a controlled mechanical response and inductive thermal response. The MAEs have a magnetic material that exhibits the inductive thermal response to the magnetic field and is embedded in a coating, such that the MAE conforms to a particular shape, e.g., a hemisphere, a dome or a shell, that is chosen to produce the desired controlled mechanical response of the entire MAE to the magnetic field. A targeting moiety for specifically binding the MAE to a pathogen target is also provided. The MAEs are preferably bound by a flexible linker to promote the desired mechanical response, which includes interactions between MAEs that are not bound to their pathogen target for the purpose of forming spheres, spherical shells, or generally spherical dimers. Such forms contain the thermal energy produced by the thermal inductive response of the magnetic material and thus reduce collateral healthy tissue damage during hyperthermic treatment. The inventing extends to appropriate apparatus and methods for diagnostics and hyperthermic treatments employing the MAEs.

24 Claims, 12 Drawing Sheets

(56) References Cited

U.S. PATENT DOCUMENTS

| | | | |
|---|---|---|---|
| 4,312,364 A | 1/1982 | Convert et al. | |
| 4,323,056 A | 4/1982 | Borrelli et al. | |
| 4,392,040 A | 7/1983 | Rand et al. | |
| 4,452,773 A | 6/1984 | Molday et al. | |
| 4,454,234 A | 6/1984 | Czerlinski et al. | |
| 4,545,368 A | 10/1985 | Rand et al. | |
| RE32,066 E | 1/1986 | Leveen et al. | |
| 4,569,836 A | 2/1986 | Gordon et al. | |
| 4,574,782 A | 3/1986 | Borrelli et al. | |
| 4,590,922 A | 5/1986 | Gordon et al. | |
| 4,610,241 A | 9/1986 | Gordon et al. | |
| 4,622,952 A | 11/1986 | Gordon et al. | |
| 4,662,359 A | 5/1987 | Gordon et al. | |
| 4,708,718 A | 11/1987 | Daniels et al. | |
| 4,735,796 A | 4/1988 | Gordon et al. | |
| 4,758,429 A | 7/1988 | Gordon et al. | |
| 4,767,611 A | 8/1988 | Gordon et al. | |
| 4,813,399 A | 3/1989 | Gordon et al. | |
| 4,889,120 A | 12/1989 | Gordon et al. | |
| 4,923,437 A | 5/1990 | Gordon et al. | |
| 4,950,221 A | 8/1990 | Gordon et al. | |
| 4,983,159 A | 1/1991 | Rand et al. | |
| 4,996,991 A | 3/1991 | Gordon et al. | |
| 5,043,101 A | 8/1991 | Gordon et al. | |
| 5,067,952 A | 11/1991 | Gudov et al. | |
| 5,087,438 A | 2/1992 | Gordon et al. | |
| 5,099,756 A | 3/1992 | Franconi et al. | |
| 5,128,147 A | 7/1992 | Leveen et al. | |
| 5,203,782 A | 4/1993 | Gudov et al. | |
| 5,300,750 A | 4/1994 | Carter, Jr. et al. | |
| 5,411,730 A | 5/1995 | Kirpotin et al. | |
| 5,441,746 A | 8/1995 | Chagnon et al. | |
| 5,468,210 A | 11/1995 | Matsui et al. | |
| 5,547,682 A | 8/1996 | Chagnon et al. | |
| 5,612,019 A | 3/1997 | Gordon et al. | |
| 5,620,480 A | 4/1997 | Rudie et al. | |
| 5,622,686 A * | 4/1997 | Gordon et al. | 424/9.32 |
| 5,658,234 A | 8/1997 | Dunlavy et al. | |
| 5,916,539 A | 6/1999 | Pilgrimm et al. | |
| 5,935,866 A | 8/1999 | Chagnon et al. | |
| 5,958,374 A | 9/1999 | Meares et al. | |
| 6,074,337 A | 6/2000 | Tucker et al. | |
| 6,149,576 A | 11/2000 | Gray et al. | |
| 6,165,440 A | 12/2000 | Esenaliev et al. | |
| 6,167,313 A | 12/2000 | Gary et al. | |
| 6,190,870 B1 | 2/2001 | Schmitz et al. | |
| 6,252,050 B1 | 6/2001 | Ashkenazi et al. | |
| 6,347,633 B1 | 2/2002 | Groth et al. | |
| 6,387,888 B1 | 5/2002 | Mincheff et al. | |
| 6,530,944 B2 | 3/2003 | West et al. | |
| 6,541,039 B1 | 4/2003 | Lesniak et al. | |
| 6,767,635 B1 | 7/2004 | Bahr et al. | |
| 6,961,620 B2 | 11/2005 | Rioux et al. | |
| 6,997,863 B2 | 2/2006 | Handy et al. | |
| 7,074,175 B2 | 7/2006 | Handy et al. | |
| 7,174,217 B2 | 2/2007 | Rioux et al. | |
| 7,189,198 B2 | 3/2007 | Harburn et al. | |
| 7,348,001 B2 * | 3/2008 | Hufton et al. | 424/130.1 |
| 7,510,555 B2 | 3/2009 | Kanzius | |
| 7,627,381 B2 | 12/2009 | Kanzius et al. | |
| 7,723,311 B2 | 5/2010 | Seeney et al. | |
| 7,781,228 B2 | 8/2010 | Menon et al. | |
| 7,857,244 B2 * | 12/2010 | Yadav et al. | 241/23 |
| 8,251,885 B2 * | 8/2012 | Ueda et al. | 600/12 |
| 8,435,496 B2 * | 5/2013 | Brougham et al. | 424/9.3 |
| 2003/0219785 A1 | 11/2003 | Hallahan et al. | |
| 2004/0229295 A1 | 11/2004 | Marchitto et al. | |
| 2005/0013778 A1 | 1/2005 | Green et al. | |
| 2005/0118102 A1 | 6/2005 | Xiang et al. | |
| 2005/0130167 A1 | 6/2005 | Bao et al. | |
| 2005/0251233 A1 | 11/2005 | Kanzius et al. | |
| 2005/0251234 A1 | 11/2005 | Kanzius et al. | |
| 2005/0271745 A1 | 12/2005 | Gruettner et al. | |
| 2005/0273143 A1 | 12/2005 | Kanzius et al. | |
| 2006/0067885 A1 | 3/2006 | Goldenberg et al. | |
| 2006/0142749 A1 | 6/2006 | Ivkov et al. | |
| 2006/0190063 A1 | 8/2006 | Kanzius et al. | |
| 2006/0233712 A1 | 10/2006 | Penades et al. | |
| 2006/0240456 A1 | 10/2006 | Chen et al. | |
| 2006/0246143 A1 | 11/2006 | Ege et al. | |
| 2007/0111330 A1 | 5/2007 | Hong et al. | |
| 2007/0111331 A1 | 5/2007 | Hong et al. | |
| 2007/0231908 A1 | 10/2007 | Cai et al. | |
| 2007/0250139 A1 | 10/2007 | Kanzius et al. | |
| 2008/0006281 A1 | 1/2008 | Sih et al. | |
| 2008/0140063 A1 | 6/2008 | Miller et al. | |
| 2008/0213377 A1 | 9/2008 | Bhatia et al. | |
| 2008/0319372 A1 | 12/2008 | Palti et al. | |
| 2009/0082611 A1 | 3/2009 | Levy et al. | |
| 2009/0132015 A1 | 5/2009 | Miller et al. | |
| 2009/0280188 A1 * | 11/2009 | Mirkin et al. | 424/499 |
| 2012/0135237 A1 * | 5/2012 | Gracias et al. | 428/402 |
| 2012/0282182 A1 * | 11/2012 | Brougham et al. | 424/9.1 |
| 2013/0028840 A1 * | 1/2013 | Van Roy et al. | 424/9.1 |

FOREIGN PATENT DOCUMENTS

| | | |
|---|---|---|
| EP | 0913167 A2 | 10/1988 |
| EP | 0333381 A2 | 3/1989 |
| EP | 0344270 | 12/1989 |
| EP | 0400940 A2 | 1/1991 |
| EP | 0543498 B1 | 5/1993 |
| EP | 0913167 | 6/2006 |
| JP | 1244767 | 9/1989 |
| WO | WO/99/19000 | 4/1999 |
| WO | WO/00/52714 | 3/2000 |
| WO | WO/01-00500 | 1/2001 |
| WO | WO/01/00501 | 3/2001 |
| WO | WO/01/37721 | 5/2001 |

OTHER PUBLICATIONS

Celli, et al., Bacterial avoidance of phagocytosis, Trends Microbiol., 10:232-237,2002.

Bayer, et al., Regulation of virulence determinants in vitro and in vivo in *Staphylococcus aureus*, FEMS Immunol. Med. Microsc., 40:1-9, 2004.

Chopra, et al., Antibiotic resistance in Staphylococcus aureus: concerns, causes and cures, Expert Review of Anti-infective Therapy, pp. 1:45-55, 2003.

Daniel, et al., Clusters of sedimenting high-Reynolds-number particles, Journal of Fluid Mechanics, 625:371-385, 2009.

Denardo,et al.,Thermal dosimetry predictive of efficacy of 111 In-ChL6 nanoparticle AMF-induced thermoablative therapy for human breast cancer in mice,J.Nuc.Med.,48(3):437,2007.

Patel, et al.,Characterization of a humanized monoclonal antibody recognizing clumping factor A expressed by *Staphylococcus aureus*, Infection and immunity, 73:5229-5232, 2005.

Driscoll, et al., Magnetic targeting of microspheres in blood flow, Microvascular research, 27(3):353-369, 1984.

Ellis et al., Eradication of methicillin-resistant *Staphylococcus aureus* from pressure sores using warming therapy, Surgical infections, pp. 4(1):53-55, 2003.

Nair et al.,Selective lethal photosensitization of methicillin-resistant *Staphylococcus aureus* using an IgG-tin (IV) chlorin e6 conjugate, J. Antimicrobial Chem, 50(6):8, 2002.

Nair, et al., Antibody-Directed Photodynamic Therapy of MethicillinResistant *Staphylococcus aureus*, Microbial Drug Resistance, 2004,92-97, 10.

Horwith, et al., Development of StaphVAX, a polysaccharide conjugate vaccine against *Staphylococcus aureus* infection: from the lab bench to phase . . . , Vaccine,2004, 880-887,22.

Fortin-Ripoche, et al., Magnetic Targeting of Magnetoliposomes to Solid Tumors with MR Imaging Monitoring in Mice: Feasibility, Radiology, 2006,415,239.

Foster, Immune evasion by staphylococci, Nature Reviews Microbiology, 2005, 948-959, 3.

Jordan, et al., Post-mortem studies in glioblastoma patients treated with thermotherapy using magnetic nanoparticles, Elsevier Journal on Biomaterial, 2008.

(56) References Cited

OTHER PUBLICATIONS

Francis, et al., Targeted photodynamic therapy of established soft-tissue infections in mice, Photochemical & Photobiological Sciences, 2004,451-458, 3.
Gemmel, et al., Glycopeptide resistance in *Staphylococcus aureus*: is it a real threat?, Journal of Infection and Chemotherapy, 2004, 69-75, 10.
Ginovart, et al., Individual based simulations of bacterial growth on agar plates, Physica A: Statistical Mechanics and its Applications, 2002, 604-618, 305.
Ginovart, et al., Simulation modelling of bacterial growth in yoghurt, International journal of food microbiology, 2002, 415-425, 73.
Gupta, et al., Minireview magnetically controlled targeted microcarrier systems, Life sciences, 1989,175-186, 44.
A. Halbreich et al., Biomedical applications of maghemite ferrofluid, Biochimie, 1998, 379-390, 80.
Hergt,et al., Maghemite nanoparticles with very high AC-losses for application in RF-magnetic hyperthermia, Journal of Magnetism and Magnetic Materials,2004,345-357, 270.
Hiraoka, et al., Development of RF and microwave heating equipment and clinical applications to cancer treatment in Japan, Microwave Theory and Techniques, 2000,1789-1799, 48.
Hornemann,et al., Biopolymer and water dynamics in microbial bio Im extracellular polymeric substance. Biomacromolecules, 2008,2322, 9.
Ohwada, et al., Fibrinolysis by urokinase endowed with magnetic property, Biochemical and biophysical research communications, 1987, 392-396, 148.
Kotsuka, et al., Development of ferrite core applicator system for deep-induction hyperthermia, IEEE Microwave Theory and Techniques,2002,1803-1810, 44.
Kotsuka, et al., New wireless thermometer for RF and microwave thermal therapy using an MMIC in an Si BJT VCO type, IEEE Microwave Theory and Techniques,1999,2630-2635,47.
Krawczyk, et al., Nonlinear development of bacterial colony modeled with cellular automata and agent objects, Int. Journal of Modern Physics,2003,1385-1404, 14.
Kreft, et al., "Bacsim, a simulator for individual-based modeling of bacterial colony growth". Microbiology, 1998,3275-3287, 144.
Lee, et al., Artificially engineered magnetic nanoparticles for ultra-sensitive molecular imaging, Nature Medicine, 2006,95-99, 13.
Lesieur, et al.,Evidence of surfactant-induced formation of transient pores in lipid bilayers by using magnetic-fluid-loaded liposomes, J. Amer. Chem.,2003,5266-5267, 125.
Lubbe, et al., Clinical applications of magnetic drug targeting. Journal of Surgical Research, 2001,200-206, 95.
Detlef et. al,Novel Magnetic Micro-and Nanoparticles for Biomedical Separation and As Means for a New Approach to AIDS Therapy, Magnetic and Electrical Sep. 2000,141-159,10.
Novick, et al., Autoinduction and signal transduction in the regulation of staphylococcal virulence, Molecular microbiology, 2003,1429-1449,48.
Patti, et al., A humanized monoclonal antibody targeting *Staphylococcus aureus*, Vaccine, 2004, S39-S43, 22.
Nesin, et al., Staphylococcal vaccines and immunotherapy: to dream the impossible dream?, Current opinion in pharmacology, 2006, 473-479, 6.
Ramanathan,et al.,An efficient direct simulation Monte Carlo method for low Mach number noncontinuum gas flows based on the Bhat . . . , Physics of Fluids, 2009, 21.
Rooijakkerset, et al., Staphylococcal innate immune evasion, Trends in microbiology, 2005, 596-601,13.
Rudge, et al., Adsorption and desorption of chemotherapeutic drugs from a magnetically targeted carrier (MTC). Journal of Controlled Release, 2001, 335-340, 74.
Schmidt, et al., The kanzius machine: A new cancer treatment idea from an unexpected source, JNCI Journal of the National Cancer Institute, 2008, 985, 100.
Senyei, et al., Biophysical drug targeting: Magnetically responsive albumin microspheres, Methods in Enzymology, 1985, 56-67, 112.
Black, et al., Use of a *Staphylococcus aureus* conjugate vaccine in patients receiving hemodialysis, New England Journal of Medicine, 2002, 491-496, 346.
Bayer, et al.,Human immunoglobulin g recognizing brinogen-binding surface proteins is protective against both *Staphylococcus aureus* and . . . , Antimicrob.Agents, 2006,511-518,50.
Johannsen, et al., Magnetic nanoparticle hyperthermia for prostate cancer,International Journal of Hyperthermia, 2010, 790-795,26.
Widdler, et al., Magnetic microspheres: synthesis of a novel parenteral drug carrier, Journal of Pharmaceutical Sciences, 1979, 79-82, 68.
Yoshimoto, et al., Magnetic urokinase: targeting of urokinase to fibrin clot, Biochem. and Biophys. Research Commun, 1988, 739-743, 152.
Zharov, et al., Photothermal nanotherapeutics and nanodiagnostics for selective killing of bacteria targeted with gold nanoparticles, Biopsy. Journal, 2006, 619-627, 90.
Peasley, et al., Destruction of human immunodeficiency-infected cells by ferrofluid particles manipulated by an external magnetic field . . . , Med. Hypoth., 1996, 5-12, 46.
Torchilin, et al., Magnetic Sephadex as a carrier for enzyme immobilization and drug targeting, Journal of Biomedical Materials Research, 1985, 461-466,19.
Richman, et al., Systemic radiotherapy in metastatic breast cancer using 90Y-linked monoclonal MUC-1 antibodies, Crit. Rev. in Oncol. Hemat. 2001, 25-35, 38, Ireland.
Kobayashi, et al., Targeting hyperthermia for renal cell carcinoma using human MN antigenspecific magnetoliposomes, Japanese Journal of Cancer Research, 2001, 1138-1146, 92.
Young, et al., A pulsed power supply system for producing high intensity magnetic and electric fields for medical applications, IEEE Pulsed Power Conference, 2001, 322.
Tucker, et al., Defining the heating characteristics of ferromagnetic implants using calorimetry, J. of Biomedical Materials Research, 2000, 791-798, 53.
Takegami, et al., New ferromagnetic bone cement for local hyperthermia, J. Biomedical Materials Research, 1998, 210-214, 43.
Paulus, et al., Corrosion analysis of NiCu and PdCo thermal seed alloys used as interstitial hyperthermia implants, 1997, 1609-1614, 18.
Petrarca, et al., Isolation of MUC1-primed B lymphocytes from tumour-draining lymph nodes by immunomagnetic beads, Cancer Immunology Immunotherapy, 1999, 272-277, 47.
Jordan, et al., Magnetic fluid hyperthermia (MFH): Cancer treatment with AC magnetic field induced excitation of biocompatib . . . , J. Magnet. and Magnet. Mater,1999,413-419,201.
Jordan, et al., Inductive heating of ferrimagnetic particles and magnetic fluids: physical evaluation of their potential for hyperthermia, J. Hyperthermia,1993, 51-68,25.
Cham, et al.,Synthesis and evaluation of colloidal magnetic iron oxides for the site-specific radiofrequency-induced hyperthermia of cancer,J. Magnetism,1993,374-378,122.
Brusentsov, et al.,Evaluation of ferromagnetic fluids and suspensions for thesite-specific radiofrequency-induced hyperthermia . . . , Magnetism & Mag. Mater.,2001,113-117, 225.
Jones, et al.,Experimental examination of a targeted hyperthermia system using inductively heated ferromagnetic microsph . . . , Physics in Medicine and Biology,2001,385-398,146.
Jones, et al., Evaluation of ferromagnetic materials for low-frequency hysteresis heating of tumours, Physics in Medicine and Biology, 1992, 293-299, 37.
Hiergeist, et al.,Application of magnetite ferrofluids for hyperthermia, J. Magnetism and Magnetic Materials, 1999, 420-422, 201.
Shinkai, et al., Intracellular hyperthermia for cancer using magnetite cationic liposomes: in vitro study, Cancer Science, 1996, 1179-1183, 87.
McDevitt, et al., Tumor therapy with targeted atomic nanogenerators, Science 2001, 1537-1550, 294.
Hergt, et al., Physical limits of hyperthermia using magnetite fine particles IEEE Trans. On Mag., 1998, 3745-3754, 34.

(56) References Cited

OTHER PUBLICATIONS

Bacri, et al., Use of Magnetic Nanoparticles for Thermolysis of Cells in a Ferrofluid, Scientific & Clinical Applications of Magnetic Carriers, 1997, 607-618, Plenum Press, NY.

Chan, et al., Physical Chemistry and In Vivo Tissue Heating Properties of Colloidal . . . , Scientific and Clinical Appl. of Magnet Carriers, 1997, 607-618, Plenum Press, NY.

Doertbudak, et al., Nd: YAG laser irradiation of infected root canals in combination with microbiological examinations, Journal of ADA, 1997,:1525-1530, 128.

Ferrer, Nd-YAG capsulotomy and intravitreal antibiotics as treatment of chronic endophthalmitis, Archivos de la Sociedad Espaiola de Ottalmolom 2000, 109-116, 75.

Ginovart, et al., Indisim, an individual-based discrete simulation model to study bacterial cultures, Journal of Theoretical biology, 2002- 305-319, 214.

Gordon, et al., Intracellular hyperthermia a biophysical approach to cancer treatment via intracellular temperature and biophysical alterations, Med. Hypoth., 1979, 83-102, 5.

Graef, et al., Materials for low Curie temperature induction heating of tumors (Hyperthermia), Ph.D. Dissertation, 1991, University of Arizona.

Hermanson, et al., "Bioconjugate Techniques", Microparticles and Nanoparticles, Academic Press, 2008.

Jordan, et al., Cellular uptake of magnetic fluid particles and their effects on human adenoarcinoma cells exposed to AC magnetic . . . , Int. J. Hyperthermia, 1996, 705-722, 12.

Jordan, et al., Magnetic Fluid Hyperthermia (MFH), Scientific and Clinical Applications of Magnetic Carriers, 1997, 569-595, USA.

Kotsuka, et al., Development of small and high efficiency implant for deep local hyperthermia, Japanese Journal of Hyperthermic Oncology, 2003, 11-22, 19.

Kotsuka, et al., Ferrite Applications to RF/Microwave Devices-New Frontiers beyond ferrite studies, IEIC Technical Report, 2006, 61-68, 106.

Kotsuka, et al., RF/Microwave Interaction with Biological Tissues, Wiley Series in Microwave and Optical Engineering, 2006.

Mitsumori, et al., Development of intra-arterial hyperthermia using a dextran-magnetite complex, Int. J. Hyperthermia, 1994, 785-793, 10.

Mitsumori, et al., Targeted hyperthermia using dextran magnetite complex: A new treatment modality for liver tumors: Is post . . . , Hepato-gastroenterology, 1996, 1431-1437, 43.

Shinkai, et al., Antibody-conjugated magnetoliposomes for targeting cancer cells and their application in hyperthermia, Biotechnol Appl Biochem, 1995, 125-137, 21.

Susuki, et al, Studies on liposomal ferromagnetic particles and a technique of high frequency inductive heating . . . , J. Soc. Cancer Ther., 1990, 2649-2658, 25.

Susuki, et al., Preparation and characteristics of magnetite-labelled antibody with the use of poly(ethylene glycol) derivatives, Biotechnol Appl. Biochem., 1995, 335-345, 21.

* cited by examiner

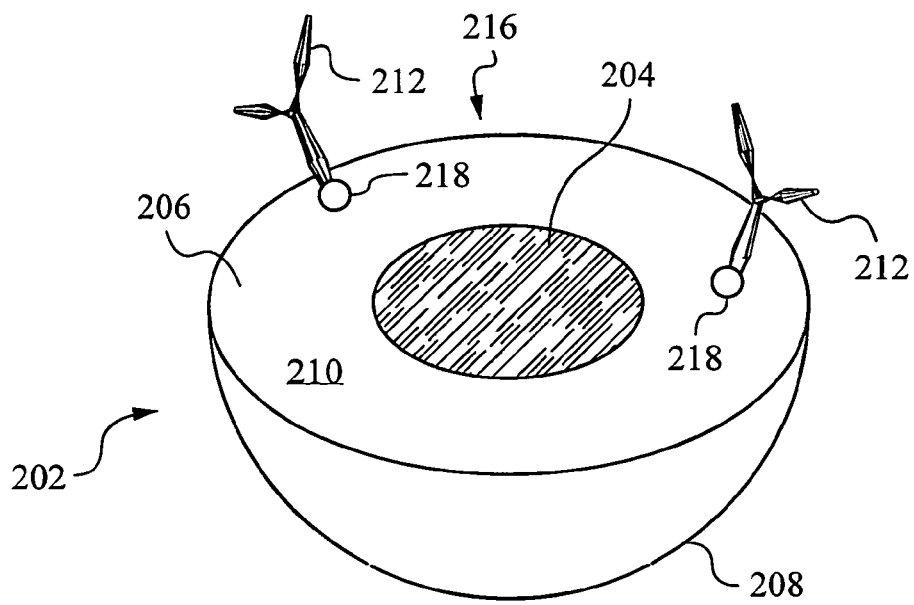
*Fig. 4*
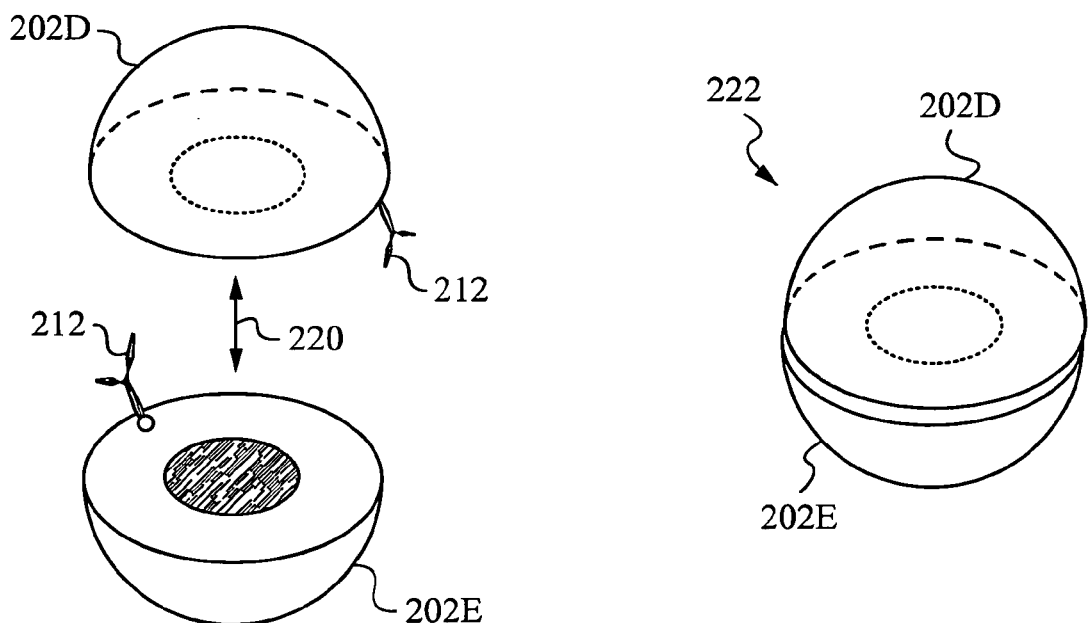
*Fig. 5A*
*Fig. 5B*

NANOPARTICLE-SIZED MAGNETIC ABSORPTION ENHANCERS HAVING THREE-DIMENSIONAL GEOMETRIES ADAPTED FOR IMPROVED DIAGNOSTICS AND HYPERTHERMIC TREATMENT

RELATED APPLICATIONS

This application claims priority from U.S. provisional patent application 61/256,986 filed on 31 Oct. 2009 and incorporated herein by reference.

FIELD OF THE INVENTION

This invention relates generally to apparatus and methods for diagnostics and hyperthermic treatments employing nanoparticle-sized magnetic absorption enhancers that attach to pathogen targets to be diagnosed or treated, and more specifically to three-dimensional geometries of such magnetic absorption enhancers that improve diagnostics and hyperthermic treatments.

BACKGROUND ART

General Review of Infectious Diseases and Development of Pathogen Resistance to Current Treatments The development of new strains of pathogenic microorganisms resistant to antimicrobial agents has become a serious risk to public health (G. C. Gemmel, "Glycopeptide resistance in *staphylococcus aureus*: is it a real threat?"; J. Infec. Chemother., pp. 10:69-75, 2004, I. Chopra, "*Staphylococcus aureus*: concerns, causes, and cures", Expert Rev. Anti Infect. Ther. pp. 1:45-55, 2003). This increasing incidence of resistant pathogens presents a serious treat to both military personnel and civilians alike. Patients suffering from resistant infections often experience increased duration and severity of infection and rate of morbidity.

Antimicrobial resistance is a biological phenomenon where bacteria multiply in the presence of an antibiotic given at a higher than therapeutic dose (WHO Global Strategy for Containment of Antimicrobial Resistance, 2001). Resistance can be described for an entire species of bacteria or it may emerge in specific strains of susceptible species. There are three stages to the development of resistance: proaction, acquired response, and selection.

This resistance results from an interplay of genetics and phenotypic expression. Genetic resistance may be acquired through genetic mutation and then propagated through a colony of pathogen cells through DNA transfer. Phenotypic expression can result in the inactivation of the drug (penicillin, chloramphenicaol), expulsion of the drug from the bacteria (tetracycline), substitution for a blocked target molecule (sulfonamide, trimethoprin), and altered affinity for the drug (quinolones and beta-lactams).

The biochemical mechanisms of resistance vary. Low-affinity PBP5 by *E. faecium* results in resistance to penicillin-based antibiotics, ampicillin, and carbapenems. Production of pbp 2a by staphylococci results in resistance to all penicillin-based antibiotics, inhibitor combinations, cephalosporins, and carbapenems. Production of ESBLs by Gram-negative results in resistance to all penicillin-based antibiotics, cephalosporins, and aztreonam. Mutations in parC and gyrA in pneumoncocci results in diminished susceptibility to all fluoroquinolones.

Examples of resistant organisms include Methicillin-resistant *Staphylococcus aureus* (MRSA), vancomycin-resistant enterococci (VRE), multiple-drug-resistant Gram-negative bacilli, penicillin-resistant *Streptococcus pneumoniae*, penicillin, tetracycline, and quinolone-resistant *Neisseria gonorrhoeae*, and multi-resistant *Shigella, Salmonella,* and *Campylobacter* species. In fact, Vancomycin-resistant enterococi (VRE), which emerged in the late 1980s, are now endemic in many hospitals with a prevalence of more than 25% reported for intensive care units in the USA in 2000 (National Nosocomial Infections Surveillance System report, 2001) VRE infections include urinary tract infections, bacteraemia, edocarditis, and wound infections.

Patients colonized with MRSA more frequently develop systemic infections, including bacteremia, poststernotomy media-stinitis, and surgical site infections. Bacteremia caused by MRSA has been associated with significantly higher mortality rates (29%-36%) than MRSSA (12-23%). The occurrence of MRSA in surgical site infections has a significant impact on clinical and economic outcomes, notably an increase in post-operative mortality. Mortality during the 90-day postoperative period was significantly higher in patients with surgical site infections due to MRSA as compared to patients with MSSA. Hospital costs were significantly higher for patients with surgical site infections due to MRSA as compared with MSSA ($p<0.001$). (Reed, S. D., Friedman, J. Y., Engemann, J. J., Griffiths, R. I., Anstrom, K. J., Kaye, K. S.)

Multi-drug resistant MRSA is now reported in a variety of settings in the United States, including communities and hospitals. In 2000 the National Nosocomial Infections Surveillance system reported that more than 50% of *Staphylococcus aureus* isolates collected from intensive care units were resistant to methicillin (MRSA). 120,000 people were infected with MRSA in 2005, causing 19,000 deaths. The cost to just treat MRSA infections in the United States can be conservatively estimated at 5 billion dollars annually. The annual cost of treating *Staphylococcus Aureus*, which is resistant to multiple drugs, can be estimated 1.5 billion dollars. There have been reports of an association between MRSA infections and major hospital care disruptions when cohort isolation and unit closure must be undertaken to control infection outbreaks. The threat of antimicrobial resistance is also related to bioterrorism.

Of particular concern is an increasing incidence of Vancomycin resistance, which has direct consequences on patient mortality (MRSA Initiative, Dept. of Veterans Affairs, 2007, Sharon S. Rotun et al. 1999). Vancomycin, has now become a commonly used therapy for MRSA, but recent studies show development of resistance to Vancomycin (Vancomycin-intermediate *Staphylococcus aureus* (VISA)). Isolates for MRSA that had intermediate resistance to vancomycin were first discovered in 1996 in Japan (CDC, MMWR Morb Mortal Mkly Rep 1997; 46; 624-6, Hiramatsu et al. 1997, Tenover et al. 2001).

It has further been shown that resistance to some of the newest classes of antimicrobials is developing at an alarming rate. There are a number of reasons for the escalating resistance trend.

First, the increased incidence of resistance is an inevitable response to the increased use of antibiotics. This trend is commonly associated with overuse of antimicrobials in intensive care units, overuse of new drugs as result of drug promotions, and prophylaxis. As a population of pathogen cells is stressed in response to an antimicrobial agent, resistance evolves via natural selection. Once a genetic change permits the survival of a given pathogen cell, this genetic information can then be propagated among pathogen cells by plasmid exchange. This is complicated by the fact that resistance to a given antibiotic can result in partial resistance to other antibiotics within the same class.

Second, clinicians may inappropriately prescribe an antibiotic that is not effective at eradicating a given infection. This increases the probability of resistance by suppressing but not eradicating the bacterial infection. Further, antibiotic treatment is completely ineffective if the invading organism is viral, protozoan, or fungal and only risks the potential that a subclinical bacterial infection develops resistance to that antibiotic. This is the result of the fact that clinicians will sometimes prescribe broad-spectrum antibiotics for patients presenting with symptoms of infection without the prior confirmation of a lab test. The tendency to treat with antimicrobials independent of laboratory results is due, in part, to the fact that it may take hours to days to obtain lab results, during which a patient's health may rapidly decline. This commonly occurs in intensive care centers, where physicians will not want to risk delaying treatment to wait for laboratory testing. In addition, because reliability of laboratory immunoassays varies among patients, giving both false-positives and false-negatives, some physicians question the laboratory results and rely instead upon symptoms to determine the course of treatment.

Third, under-treating either with a dose that is too low or for a duration that is too short or as a result of counterfeit medications can promote resistance. Other factors that may contribute to inadequate antimicrobial treatment include use of broad-spectrum antibiotics, prolonged hospitalization and prolonged mechanical ventilation. It is very important that the right antibiotic be used at the outset to reduce the probability of resistance developing.

Fourth, non-medical use of antimicrobials as a result of animal husbandry, aquaculture, and horticulture can promote the development of resistance.

Prior Art Diagnostic and Treatment Options in View of Resistant Pathogens

In order to address this growing resistance trend requires the development of new diagnostics and therapeutics. First, there is a need for rapid, reliable diagnostic methods to determine the presence and severity of infection and reduce the misuse of antibiotics. Second, there is a need for rapid antimicrobial treatments that do not contribute to the escalating resistance trend by selecting for the emergence of resistant pathogens.

Certain pathogens do not exhibit resistance, but instead exhibit persistence. These pathogens are still susceptible to antimicrobials, but are either able to evade them by sequestering themselves in regions of the body away from the reach of the agent or else by entering a dormant state which renders the organism no longer susceptible to antimicrobials.

These typically anaerobic pathogens prefer to reside in hypoxic regions of the body, away from the oxygen-rich bloodstream. Hidden deep within tissues, such pathogens evade the host immune system and any antimicrobial agent introduced into the bloodstream. Once hidden from the immune system, such pathogens are able to enter a dormant state, where antimicrobial agents have no effect until they revert to the active state. This behavior leads to a persistent infection, where antimicrobials are only able to prevent a further escalation of disease, but are unable to ultimately eradicate the pathogen. Certain disseminated infections have therefore been shown unresponsive to antimicrobial therapy. Such infections include *Borrelia Burgdorferi*, which may be able to sequester in collagen fibers, leading to persistent illness. To address this persistence problem, new technologies may be required.

One of the most dangerous aspects of the current problem is that, while the situation is worsening, little industrial research is being done to develop new methods for combating the problem of antibiotic resistance and evasion. This is a direct consequence of the recent glut of patent expirations and the flood of generics on the market. Of the 370 antibacterials currently in development, 60% are in pre-clinical stages, and many show substantial similarity to classes of antibacterial agents currently in use against which resistance is already present. This suggests that these new antimicrobial compounds will be unlikely to overcome the growing resistance trend. Therefore, as the need is growing for new anti-infectives, many pharmaceutical companies have reduced their efforts to develop them. Thus, there is a deep-felt need to develop new technologies to combat the growing resistance trend.

Alternative Diagnostic and Treatment Options Including Hyperthermia

In the field of cancer research, RF ablation technology has been explored since the early 1920's. Until recently, treatment typically involved the exposure of the host to electromagnetic (EM) radiation in the RF frequency spectrum through either the insertion of an RF ablation electrode catheter into the tumor or through the exposure of a tumor to RF radiation from an external RF field generator. However, these technologies were limited in several ways that prevented them from being more widely applied for other medical treatments, including infectious disease treatment.

Early RF ablation therapies were limited in their ability to target specific regions of the body with precision, either resulting in insufficient destruction of cancer cells or the destruction of healthy cells (J. Cardinal, E. Chory, J. Klune, I. Icili, J. Kanzius and D. Geller, "158. Non-invasive radiowave ablation of cancer targeted by gold nanoparticles", Journal of Surgical Research, Vol. 144, No. 2, pp. 247, 2008). Further, heating would occur slowly, requiring long treatment times. Second, early prior art RF ablation therapies were unable to simultaneously target many discrete regions of the body with precision. Third, these RF ablation therapies were not easy to administer. In the case of the catheter, a needle had to be surgically inserted, while the RF field generator required several hours to cause sufficient heating.

More recently, nano-structures have been introduced to improve the previous RF ablation techniques. In particular, these nano-structures, e.g., conductive and/or magnetic beads as taught by Rioux et al. in U.S. Pat. Nos. 6,961,620 and 7,174,217 can act as absorption enhancers, absorbing EM radiation and causing localized heating. When injected into tumor tissue, such particles cause additional heating, decreasing the duration of therapy and reducing the potential for the destruction of healthy human cells. Careful placement of such nano-structures in the host enables simultaneous heating of multiple discrete regions of the body. Additional information about magnetic nanoparticles, such as their composition and preparation, can be found in U.S. Pat. No. 6,767,635 to Bahr et al.

In other applications, nano-therapeutics are used to cause either physical or chemical damage to a target pathogen (R. P. Novick, "Autoinduction and signal transduction in the regulation of staphylococcal virulence", Mol. Microbiol., pp. 48:1429-1449, 2003; M. L. Embleton, S. P. Nair, B. D. Cookson and M. Wilson, "Selective lethal photosensitization of methicillin-resistant *Staphylococcus aureus* using an IgG-tin (IV) chlorine 6 conjugate", J. Antimicrob. Chemother. (2002), 50(6), pp. 857-864). Each of these methodologies has various limitations. In general, they all suffer from limited applicability and potentially serious side effects that prevent widespread use. These include photodynamic therapy (PDT) (F. Gad, T. Zahra, T. Hasan, and M. R. Hamblin, "Targeted photodynamic therapy of established soft-tissue infections in mice", Proc. SPIE 5315, 65 (2004), M. L. Embleton, S. P. Nair, B D. Cookson, and M. Wilson, Selective lethal photosensitization of methicillin-resistant *Staphylococcus aureus* using an IgG-tin (IV) chlorine 6 conjugate", J. Antimicrob. Chemother. (2002) 50(6): 857-864), the use of chemical agents bound to monoclonal antibody targeting proteins, and photothermal nanotherapeutics, e.g., as taught by West et al. in U.S. Pat. No. 6,530,944.

The use of RF EM fields and non-toxic nano-materials bound to a monoclonal antibody or other targeting ligand overcomes many of the above-mentioned limitations. First, RF magnetic fields at less than 2 MHz have a skin depth of over 100 centimeters, which allows heating to penetrate deeply into tissues. Second, the use of non-toxic, paramagnetic nano-materials eliminates risk associated with damaging healthy cells, as is the case in chemical treatments. Third, the treatment is due to thermal destruction of the target pathogen and does not rely upon the presence of oxygen in the environment, as is the case with the photodynamic therapies. Fourth, the use of magnetic nano-materials allows the particles to be selectively moved through the host to target regions of the body with limited blood flow. Teachings on guiding nanoparticles with magnetic fields are contained, e.g., in U.S. Pat. No. 7,189,198 to Harburn et al and U.S. Pat. No. 7,723,311 to Seeney et al.

The application of magnetic nano-particles and RF magnetic fields for inducing hyperthermia have been previously explored for treating various cancers with varying degrees of success (W. Daum, G. DeNardo, D. Ellis-Busby, A. Foreman, D. U. Gwost, E. S. Handy, R. Ivkov, et al., "Therapy via targeted delivery of nanoscale particles using 16 antibodies", February 2003. U.S. patent application Ser. No. 10/360,578 A. Jordan, R. Scholz, K. Maier-Hauff, F. K. H. van Landeghem, N. Waldoefner, U. Teichgraeber, J. Pinker-nelle, H. Bruhn, F. Neumann, B. Thiesen, et al. "The effect of thermotherapy using magnetic nanoparticles on rat malignant glioma" Journal of Neuro-oncology, 78(1):7-14, 2006). However, thermoablative therapy to treat infectious diseases differs from treatment of cancer in five distinct ways.

First, all cancer cells may perish at <43° C., while destruction of a prokaryotic bacterial cell may necessitate a temperature rise that exceeds 60° C. and/or requires a faster thermal transient. To achieve higher temperatures and do so safely presents new challenges in magnetic field generator design and nanoparticle design. In particular, >1 kW/g of heating within the nanoparticle may be required to achieve sufficient heating, while the field generator must limit the Specific Absorption Rate (SAR) to reduce nonspecific tissue heating. Therefore, magnetic field coupling must be increased to increase inductive heating efficiency without significantly increasing the SAR.

Second, thermoablative therapy for cancer targets solid tumors, where the area selected for heating is known and stationary. This is not possible in the case of infectious disease treatment, where the infection or the pathogen targets must first be localized, and where their location may change.

Third, in solid tumors thermoablative tissue destruction is mostly limited to tumor periphery. Targeting individual pathogen cells distributed among both healthy and unhealthy tissues presents further risk of thermoablative destruction of healthy tissue. Some prior art references teach the use of appropriate magnetic field gradients to control temperature effects and limit heating of healthy tissue. Xiang et al. provide corresponding teaching in U.S. Pat. Appl. 2005/0118102. Other prior art references, such as U.S. Pat. No. 6,997,863 to Handy et al., suggest a need for good targeting and short treatment duration such that the heat is concentrated on the pathogen target.

Fourth, nanoparticle concentration in wounds may be lower than that in tumors, possibly resulting in less heating. Thus, higher power density within the nanoparticles is required to obtain necessary heating. This necessitates higher frequency AMFs. Yet, collateral healthy tissue damage must still be taken into account.

Fifth, while electromagnetic/thermal models have been built to model nanoparticle hyperthermia in solid tumors, no such model has ever been developed to model the application of this technology to treat colonies of pathogen cells. Therefore, the prior art does not contain teachings about appropriate parameter selection for performing in vivo thermoablation of a given pathogen target. Indeed, the only related use of thermoablative technology to treat infections was performed by Muller-Schulte et al. at Institut fur Anorganische Chemie and was focused upon the treatment of HIV (Detlef Miller-Schulte, "Novel magnetic micro- and nanoparticles for biomedical separation and as a means for a new approach to AIDS therapy", Magnetic and Electrical Separation, 10:141-159, 2000). However, research to date has focused upon in vitro analysis of biochemical functionality.

The above-cited U.S. Pat. No. 6,997,863 to Handy et al., as well as the related references including: U.S. Pat. No. 7,074,175, US, WO/2005/0271745, US WO/2006/0142749, and US WO/2006/0246143 do disclose therapeutic methods for the treatment of disease material involving administration of thermotherapeutic magnetic compositions. However, these references largely focus upon treatment of a variety of cancers, and the thermotherapeutic treatment of cancer differs from the thermotherapeutic treatment of infectious diseases in several ways as previously described herein. Therefore, the technology disclosed in U.S. Pat. No. 6,997,863 and related patents is not well-suited to diagnose and treat infectious diseases that are highly mobile and located in various environments, where high temperature is required but collateral damage to healthy tissue needs to be maintained as low as possible.

Recently, Kanzius et al. have taught to combine RF induced hyperthermia and nanoparticles for ablation of cancer cells in U.S. Pat. Nos. 7,510,555; 7,627,381 and in related references USWO/2007/0250139, US WO/2006/0190063, US WO/2005/0251234, US WO/2005/0273143, US WO/2005/0251233. The Kanzius references disclose the use of an RF treatment system and device for inducing hyperthermia in cancer cells. The '234 application discloses injecting into the body of a patient tumor antibodies containing RF absorbing nanoparticles that target the cancer cells. Once the antibodies have reached their target, the RF treatment device is used to induce hyperthermia in those cells by heating the nanoparticles, which in turn heats the cancers cells and either damages or kills them.

Although most applications focus upon the use of hyperthermia and nanoparticles to treat various forms of cancer, Kanzius mentions that the antibodies can be directed against any biologically active molecule (e.g. bacterial, fungal, viral, and parasitic). However, the applications do not teach how to apply the technology to treat non-stationary, pathogenic targets, such as bacterial, and parasitic infections. Such targets demonstrate unique mechanisms that render them resistant to therapeutic mechanisms described in the Kanzius references.

In particular, the pathogenic targets have varying temperature sensitivities. Generally, cancer cells will perish at temperatures exceeding 45° C., but certain bacteria exhibit widely differing thermal sensitivities. For example, a log-6 order destruction of Methicillin Resistant *Staphylcoccocus Aureus* may occur after several seconds of exposure to 55° C., and that represents a 18° C. temperature transient. Some targets may exhibit even higher resistance, requiring exposure to 60° C. or more. And yet, such high temperature transients have to be achieved without provoking substantial collateral damage in surrounding healthy cells. Moreover, as the pathogen targets can be non-stationary (highly mobile), reaching and treating them has to be efficient.

Another set of challenges has to do with eddy currents that produce heating of tissue near the surface of a patient's skin. Most technologies described in the Kanzius references make use of electric field components to induce dielectric heating of the pathogen targets. Such dielectric heating disproportionately heats fat tissue, resulting in non-uniform heating that poses potential risk to the patient of overheating or burning. Further, field strength beneath fat tissue is significantly attenuated due to absorption of electromagnetic radiation in the fat tissue. This may prevent sufficient heating of particles beneath fat tissue without overheating the surrounding fat tissue.

Some prior art references suggest that issues of better heating and targeting of pathogen targets may be addressed by better design of the nanoparticles. For example, U.S. Pat. No. 6,767,635 to Bahr et al. teaches nanoparticle aggregation and binding of the magnetic nanoparticles with the aid of linkers. U.S. Pat. No. 7,781,228 to Menon et al. discloses the use of agglomerations of nanoparticles to better control temperature and to ascertain the presence of target analytes under in-vitro conditions. Finally, U.S. Pat. Appl. 2004/0229295 Marchitto et al. teaches the use of 2 spherical nanoparticles to enhance the magnitude of interaction between the target and the EM energy.

Unfortunately, the prior art does not provide nanoparticles that are suitable for hyperthermic diagnostics and treatment of highly mobile pathogen targets requiring high temperature transients while ensuring low collateral damage to healthy tissue. Specifically the prior art does not provide nanoparticles that use the magnetic portion of the EM radiation, i.e., nanoparticle-sized magnetic absorption enhancers, and are suitable for in-vivo applications.

OBJECTS AND ADVANTAGES OF THE INVENTION

In view of the shortcomings of the prior art, it is an object of the invention to provide nanoparticle-sized magnetic absorption enhancers (MAEs) that use appropriate geometries to exhibit a controlled magnetic and mechanical response to a magnetic field. Specifically, the nanoparticle-sized MAEs in accordance with the invention are intended to overcome the prior art limitations with magnetic material that is embedded in a coating in a manner that permits application of high temperature transients while limiting collateral damage to healthy tissue.

It is a further object of the invention to ensure that the nanoparticle-sized MAEs cooperate in a manner that further improves their ability to induce large thermal transients while limiting collateral damage by reducing the specific absorption rate (SAR) of thermal energy by healthy cells. Indeed, the MAEs of the instant invention are to safely enable thermal transients reaching 60° C. and higher, including regimes in which vapor bubbles are formed.

A still further object of the invention is to provide MAEs that are not only safe while generating hyperthermia, but also enable tracking of pathogen targets in a host for diagnostics and other purposes.

These and many other objects and advantages of the invention will become apparent from the ensuing description.

SUMMARY OF THE INVENTION

The objects and advantages of the invention are secured by a nanoparticle-sized magnetic absorption enhancer (MAE), which exhibits a controlled response to a magnetic field. The MAE is made of a magnetic material chosen to have a certain inductive thermal response to the magnetic field and being embedded in a coating that conform to a particular shape. The shape is selected to produce a controlled mechanical response of the entire MAE to the magnetic field. A targeting moiety for specifically binding the MAE to a pathogen target is also provided. The inductive thermal response and the controlled mechanical response together constitute the controlled response according to the invention. It is important that the total controlled response be well behaved when the magnetic field is present or applied, and absent or turned off.

In a preferred embodiment, the MAE is bound to at least one other MAE according to the invention by a flexible linker. Such linker can be attached to the coating that embeds the magnetic material. The linker molecules or compounds, including hydrophobic molecule chains, are preferably bound to the surface of the coatings belonging to two or more MAEs.

There are several appropriate overall shapes for the MAE. Note that each particular MAE's geometry is imposed by the three-dimensional shape of its coating. Now, in accordance with the instant invention, that shape is a hemisphere, a dome or a shell, as opposed to a sphere.

In fact, it is important that the shape of one MAE be complementary to another MAE in the sense that their controlled mechanical response is an interaction between them. Preferably, the interaction results in the formation of a sphere, a spherical shell or a generally spherical dimer. Specifically, as the magnetic response of the magnetic material is an inductive thermal response, which produces thermal energy, it is important that free MAEs (ones that have not bound to a pathogen target) interact to form a sphere, a spherical shell or a generally spherical dimer in order to contain the inductive thermal response. In other words, the sphere, spherical shell or generally spherical dimer formed by an interaction of the MAEs insulates the surroundings from the thermal energy generated by the magnetic response.

Furthermore, the magnetic material may be embedded in the coating as a single part, or it may be distributed in a number of magnetic crystals. Preferably, when the magnetic material is distributed in a number of magnetic crystals, each of those is small enough to behave as a single magnetic domain. In that same or another embodiment, the shape of the MAE is a shell and the controlled mechanical response is a pinching of the shell to contain the thermal energy due to the inductive thermal response of the magnetic material.

The targeting moiety is either attached to the coating of the MAE or else directly to the magnetic material. In the latter case, it is advantageous to provide a passage for the targeting moiety through the coating. The attachment of the targeting moiety is chosen based on the shape of the MAE. In particular, when the shape is a hemisphere the targeting moiety is attached to the face of the hemisphere; when the shape is a shell then the targeting moiety is attached to its inner face; and when the shape is a dome the targeting moiety is attached to its inner portion.

In general, attachment of the targeting moiety is accomplished with the aid of a bond. Suitable bonds rely on bonding mechanisms such as passive absorption, covalent coupling, hydrogen bonding, secondary or tertiary amine linkage, amide linkage, Schiff base linkage, isourea linkage, thiourea linkage, carbamate linkage, ether linkages, thioether linkages, strept(avidin)-biotin interactions, hydrazone linkages and SPDP crosslinker coupling.

The MAEs have to be biocompatible, since they may be administered to a host and be employed for diagnostics and hyperthermia treatment in-vivo. Therefore, the coating should be made of a suitable biocompatible material. Advantageous choices of biocompatible material include $SiO_2$, dextran, gold, silver and polyethylene glycol. In general, however, the material can be any one or a combination of materials selected from the group of biodegradable polymers, modified dextran coatings, cross-linked dextran coatings, polylactide/polyglycolide copolymers, poly(orthoesters), poly(anhydrides), microemulsions, liposomes, and thermally sensitive lyposomes (LTSLs, HTSLs).

The MAEs of invention are used in an apparatus for inducing transient hyperthermia in a pathogen target. The apparatus has an arrangement, typically consisting of magnetic coils, for generating the magnetic field to which the magnetic material of the MAE has an inductive thermal response. In a preferred embodiment, the magnetic coils are NMR coils including coils that generate an alternating magnetic field. The alternating magnetic field causes a certain amount of inductive heating of the magnetic material, which produces thermal energy. In some cases, the alternating magnetic field may be supplemented by a static magnetic field.

Meanwhile, the controlled mechanical response of the MAE is a change in the shape of the MAE. For example, the change in shape is a bending of the MAE when the magnetic field is being generated. In the same or other embodiments, the controlled mechanical response can include an interaction of the MAE with at least one other MAE according to the invention to form a geometrical arrangement for containing the inductive thermal response, or, more precisely, the thermal energy produced by the inductive thermal response.

The invention further extends to a method for inducing transient hyperthermia in a pathogen target. The method includes the steps of generating a magnetic field and providing a nanoparticle-sized MAE. The MAE exhibits a controlled response to the magnetic field that includes an inductive thermal response by the magnetic material and a controlled mechanical response dependent on the shape imposed on the MAE by the coating in which the magnetic material is embedded. The MAE, and, in practice, a number of such MAEs, are delivered to a region in which the pathogen target resides. Since the MAEs are provided with targeting moieties for specific binding with the pathogen target, a number of them undergo such binding. Meanwhile, some MAEs remain unbound or free.

The magnetic field that is applied includes an alternating magnetic field for directly producing the inductive thermal response in the magnetic material of the MAE. In addition, a static magnetic field can be provided. The static field can be tuned in direction and magnitude to control the activity of the MAE.

In a preferred embodiment, the static magnetic field is provided and the magnetic material is further selected to exhibit magnetism upon the application of the static magnetic field. In particular, the magnetic material exhibits a magnetic dipole-dipole coupling response once the static magnetic field is applied. This magnetic dipole-dipole coupling response between various regions of the magnetic material, or even separate magnetic crystals of said magnetic material, affects the controlled mechanical response such that it includes a change in the shape of the MAE. This change can include bending of the MAE. In an advantageous application of the method, the shape is a shell and the bending results in a pinching or closing of the shell, thereby containing the inductive thermal response of the magnetic material.

Of course, the MAEs of invention as well as the apparatus and method can be embodied in many different ways. A detailed description of the preferred embodiments of the invention presented below in reference to the appended drawing figures will elucidate these embodiments and extensions thereof.

BRIEF DESCRIPTION OF THE DRAWING FIGURES

FIG. 1 (Prior Art) is a three-dimensional schematic view of the principles of inducing hyperthermia with the aid on nanoparticles containing a magnetic material.

FIGS. 2A-B (Prior Art) are schematic diagrams illustrating the mechanics behind inductive thermal response of the magnetic material, specifically a ferromagnetic material of the nanoparticles of FIG. 1.

FIG. 4 is a three-dimensional diagram of an MAE in accordance with the invention.

FIGS. 5A-B are three-dimensional views illustrating a suitable mechanical response of MAEs with complementary shapes in accordance with the invention.

FIGS. 6A-F are three dimensional views illustrating various MAE structures and a preferred linking mechanism according to the invention.

Figure 7:
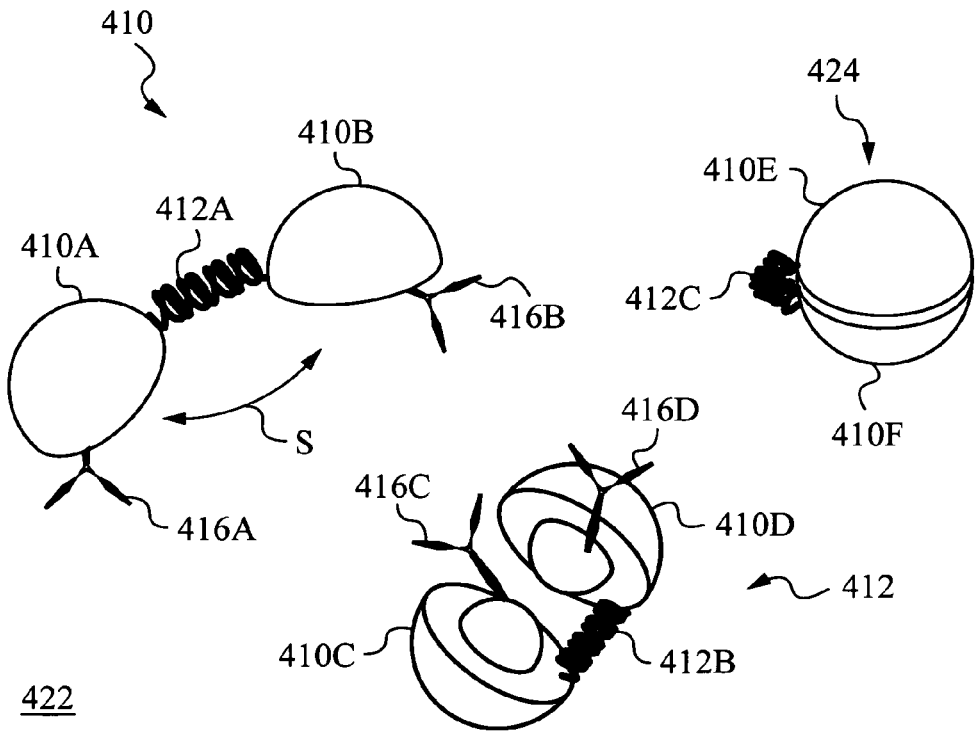
Figure 7:
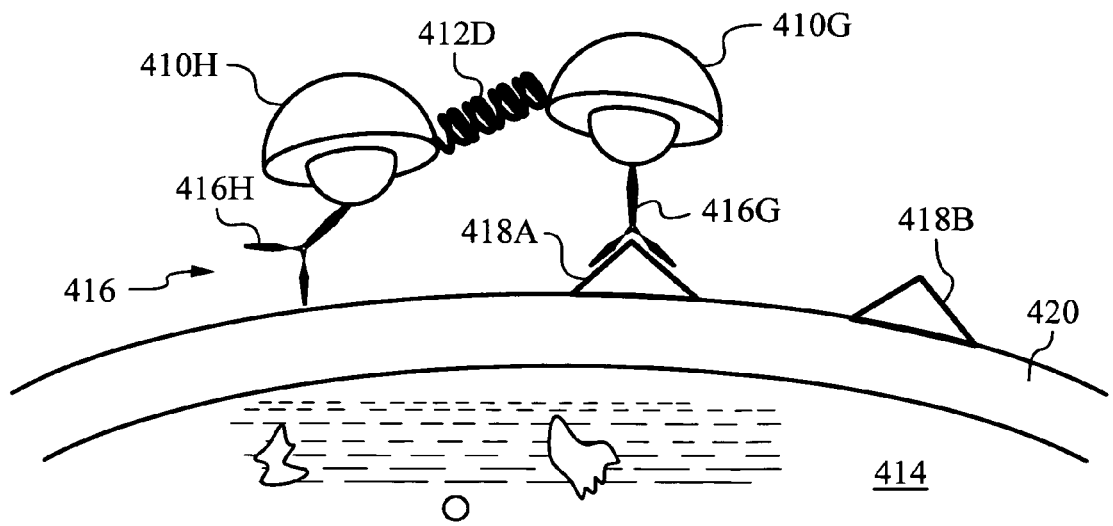

FIG. 7 is a diagram illustrating the application of linked MAEs and the advantageous mechanical response and inductive thermal response obtained thereby.

Figure 8:
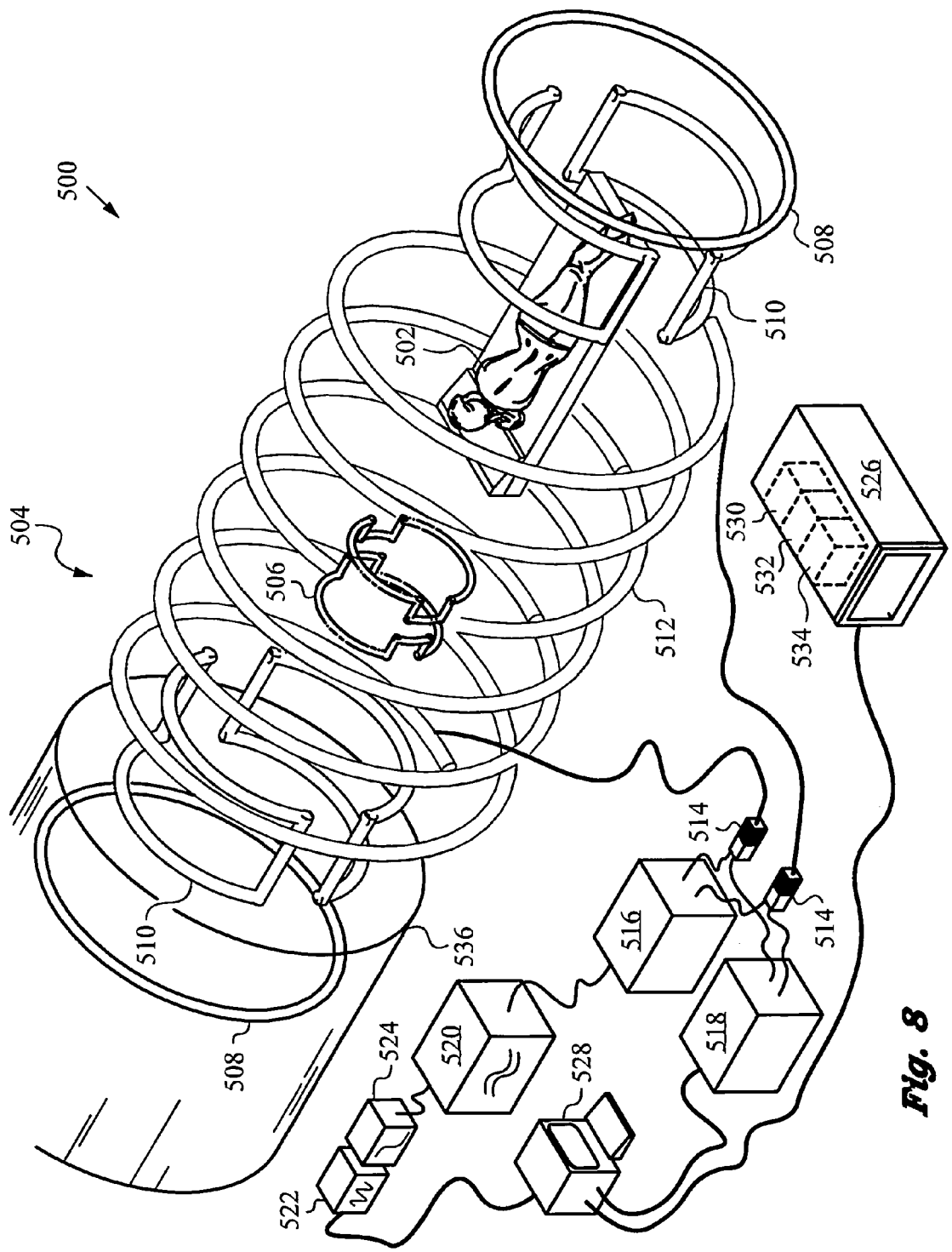

FIG. 8 is a three-dimensional, exploded schematic view of a preferred apparatus for diagnostics and hyperthermic treatment in accordance with the invention.

Figure 9:
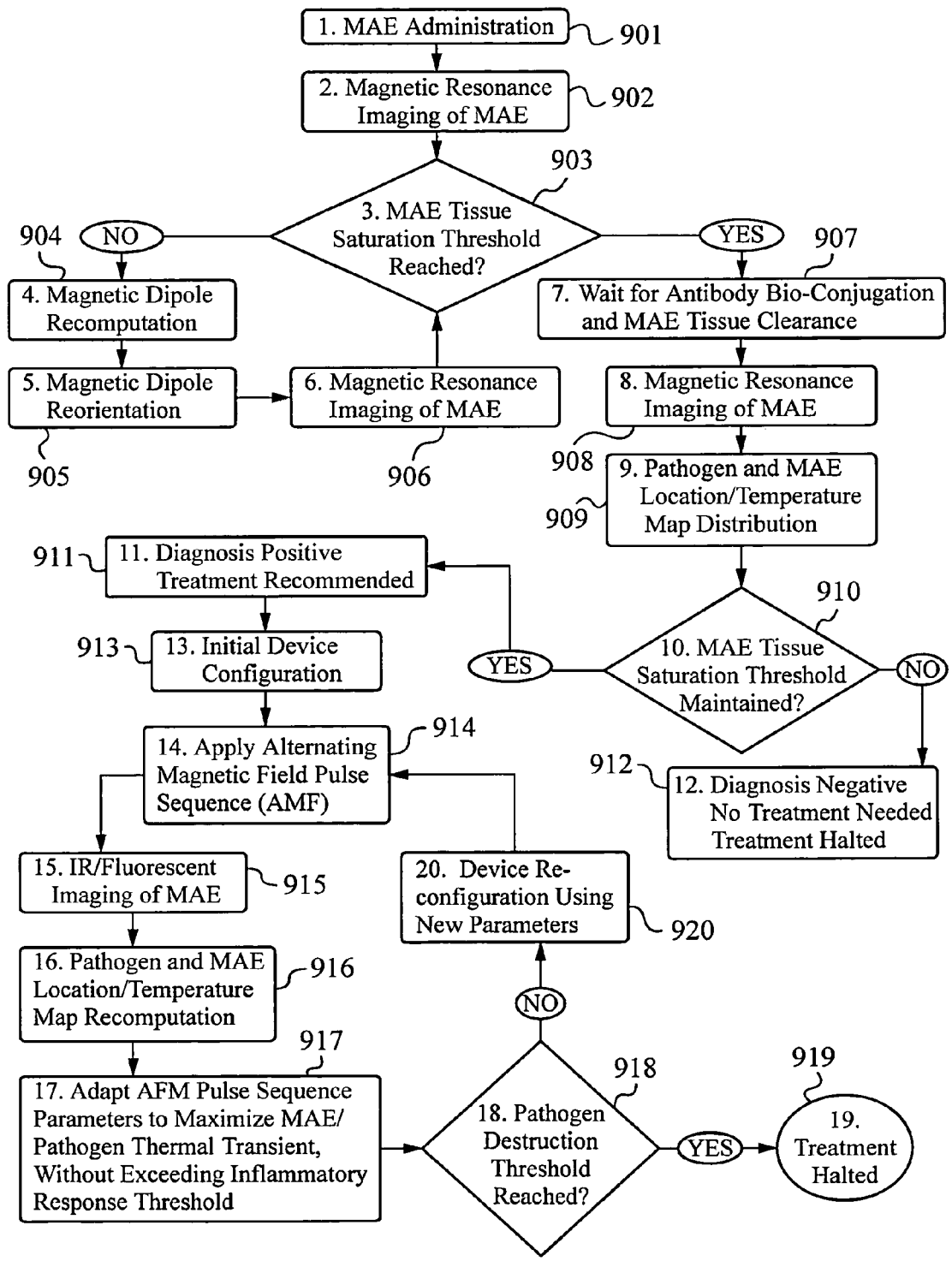

FIG. 9 is a block diagram illustrating the steps of the method of invention.

Figure 10:
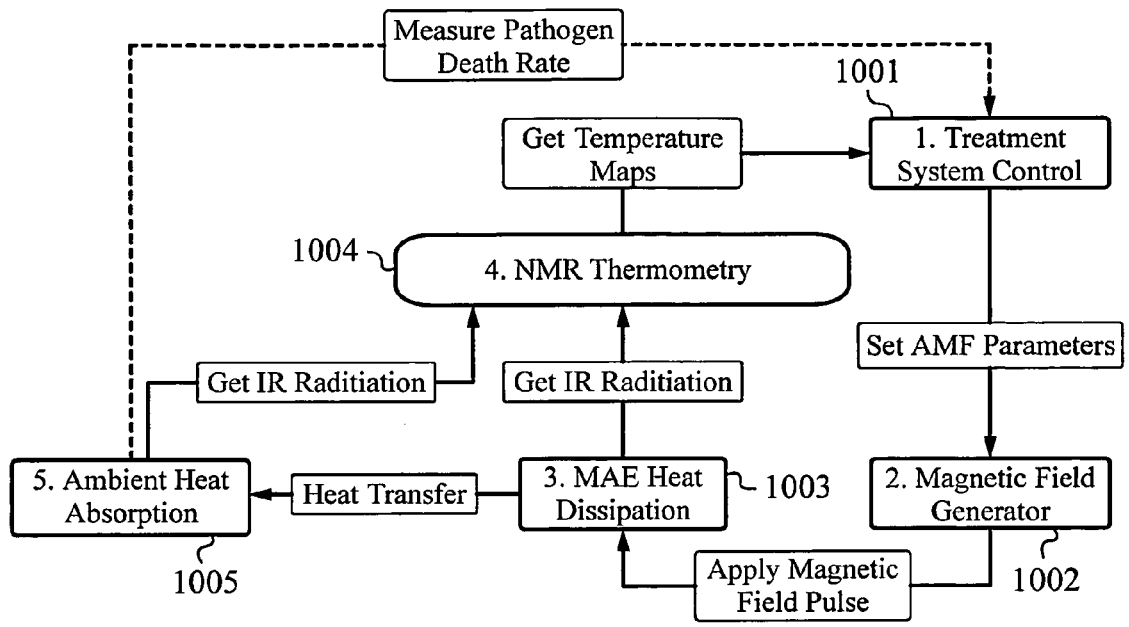

FIG. 10 is a block diagram illustrating the overall operation of a control system for supervising an apparatus according to the invention in carrying out a method of the instant invention.

Figure 11A:
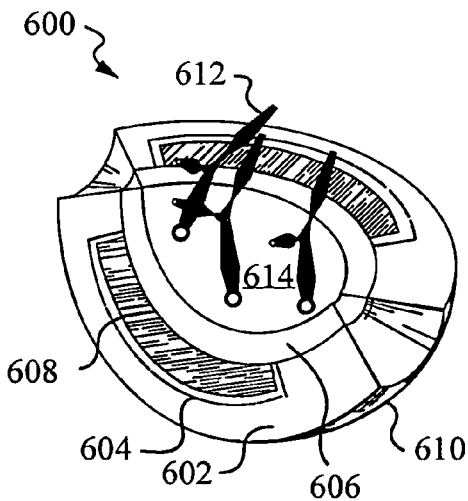
Figure 11B:
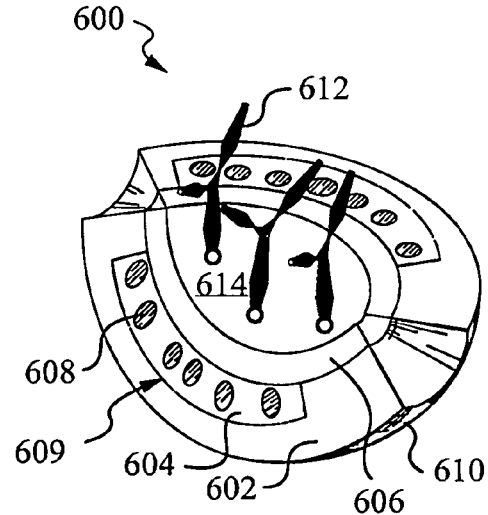

FIGS. 11A-B are three-dimensional views of an MAE that is shell shape and undergoes a controlled mechanical response that includes bending and/or pinching.

Figure 12A:
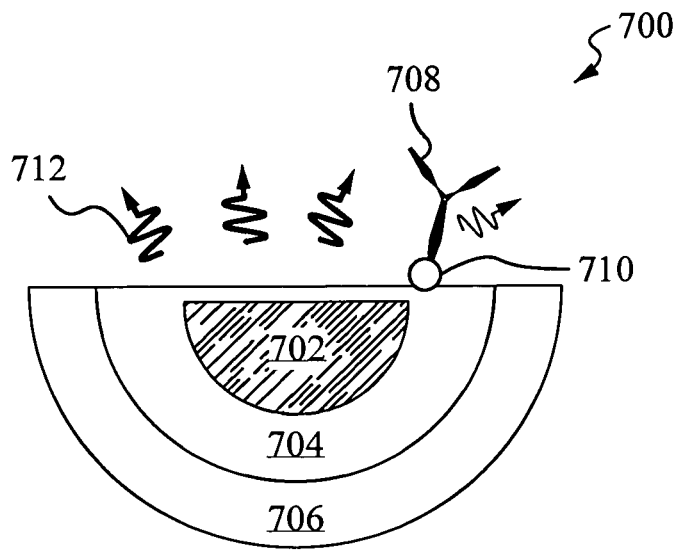
Figure 12B:
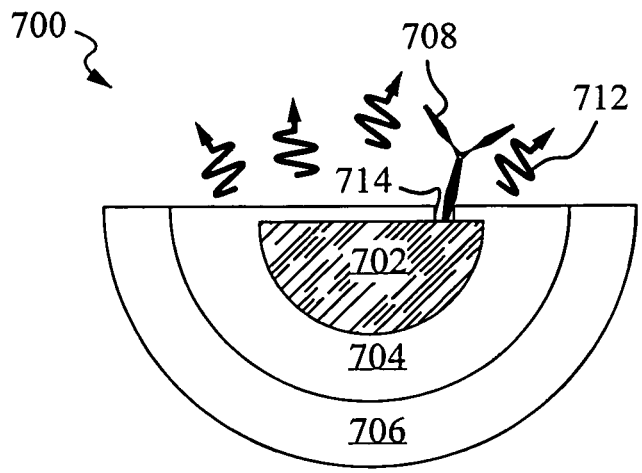

FIGS. 12A-B are cross-sectional views illustrating the attachment of targeting moieties to a coating and directly to the magnetic material of an MAE.

Figure 13:
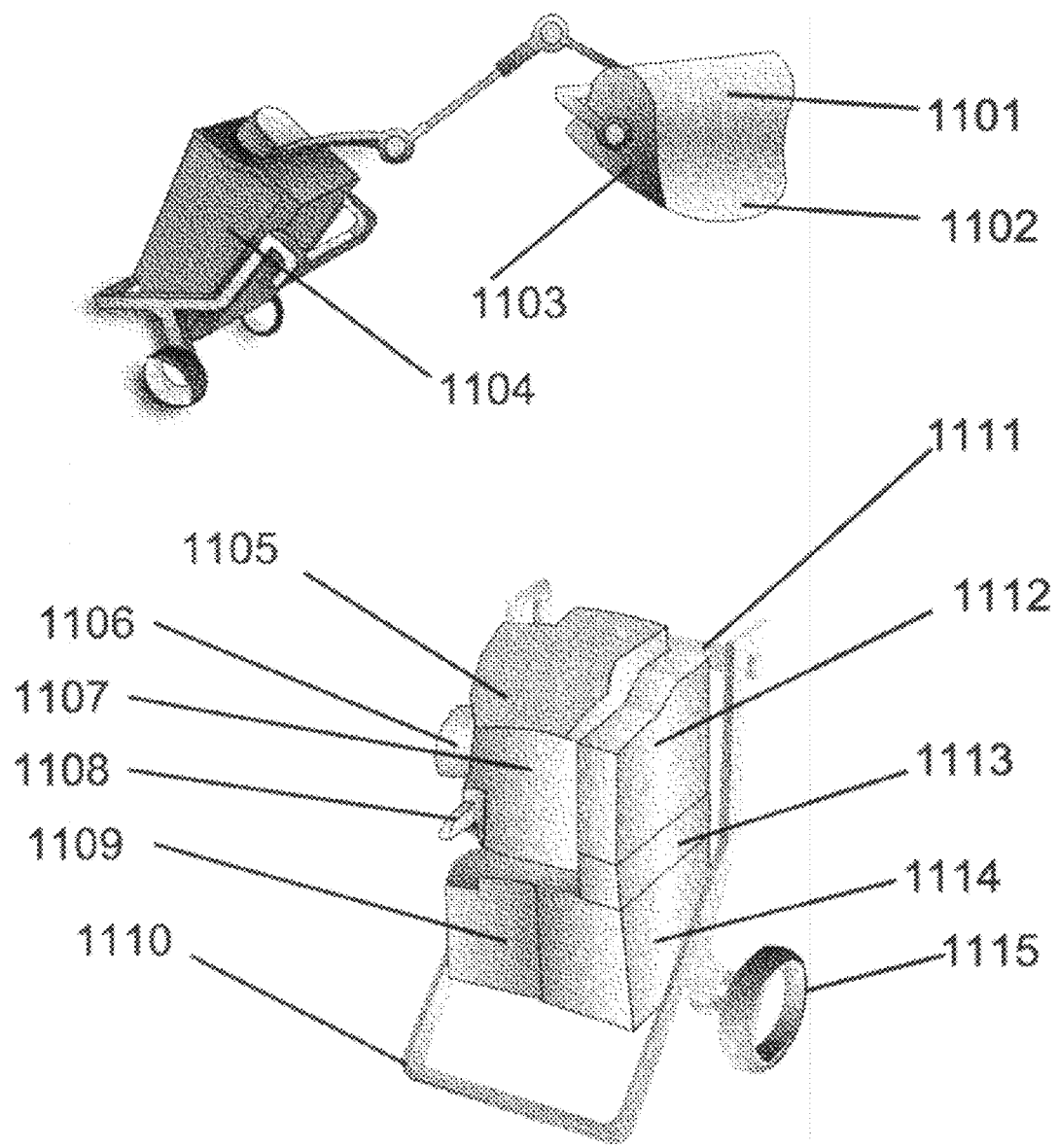

FIG. 13 illustrates a portable version of an apparatus according to the invention.

Figure 14:
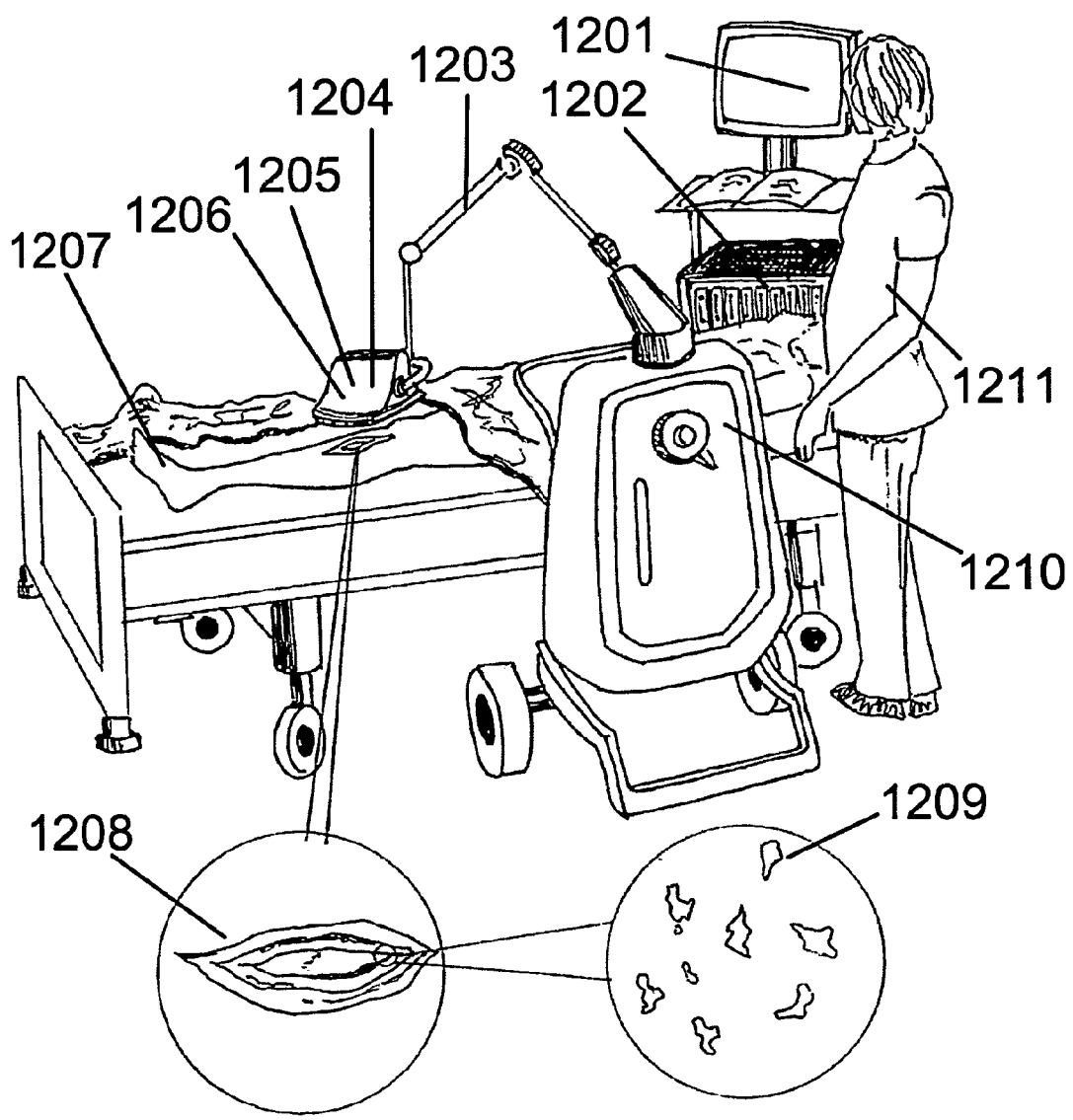

FIG. 14 depicts an apparatus of the invention adapted for treating wounds infected with a pathogen target.

DETAILED DESCRIPTION

Prior Art Principles of Inducing Hyperthermia

Figure 1:
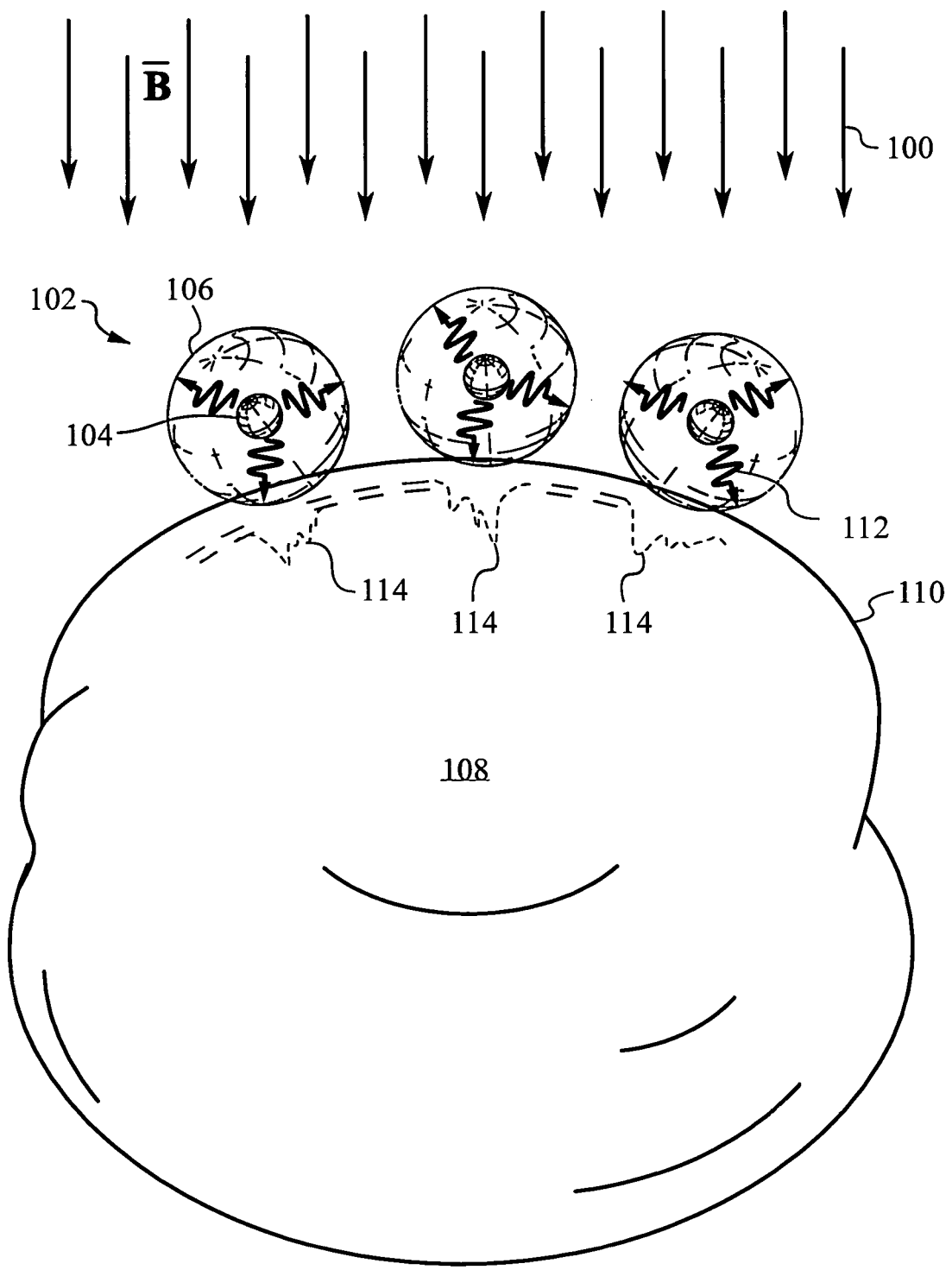

The best way of explaining the invention is by initially referring to the three-dimensional schematic view of FIG. 1, which explains the prior art principles behind inducing hyperthermia using an alternating magnetic field 100 (AMF) with a frequency in the radio-frequency (RF) range. A number of nanoparticles 102 containing a magnetic material 104 at their cores are provided. Nanoparticles 102 have a mechanism, not shown, that binds their outer coatings 106 to a pathogen target 108. In this case, pathogen target 108 is a cell, e.g., a cancer cell, and outer coatings 106 are bound to a cell wall 110 of target 108.

A typical magnetic material 104 is $Fe_2O_3$, $Fe_3O_4$ or Co. In accordance with known principles of electro-magnetism, AMF 100 is applied to nanoparticles 102 bound to cell wall 110. AMF 100 provokes an inductive thermal response in magnetic material 104. This response produces thermal energy 112. Thermal energy 112 thus generated is sufficient to cause ruptures 114 or other damage to cell wall 110 of target 108. The actual transfer of thermal energy 112 includes many typical thermal mechanisms such as conduction, convection and/or radiation. The transfer in typical prior art applications may take on the order of minutes or tens of minutes. Furthermore, typical temperatures reached at cell wall 110 in prior art applications are about of 46.5° C., or sufficient to destroy cell 108 provided it is a typical eukaryotic cell.

Figure 2A:
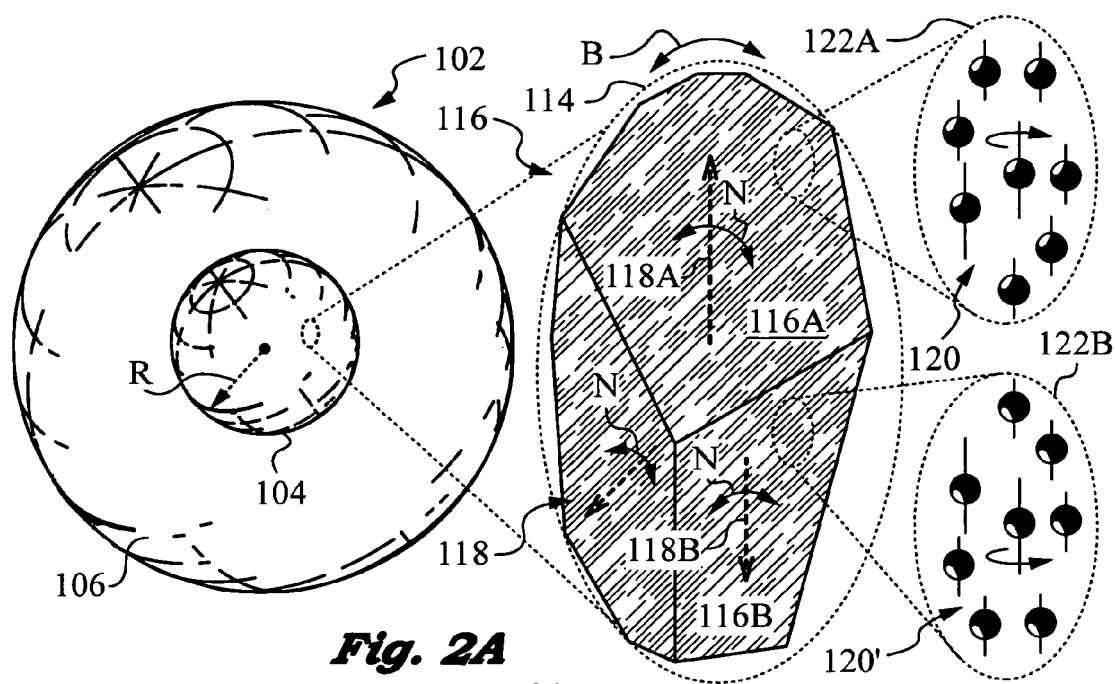
Figure 2B:
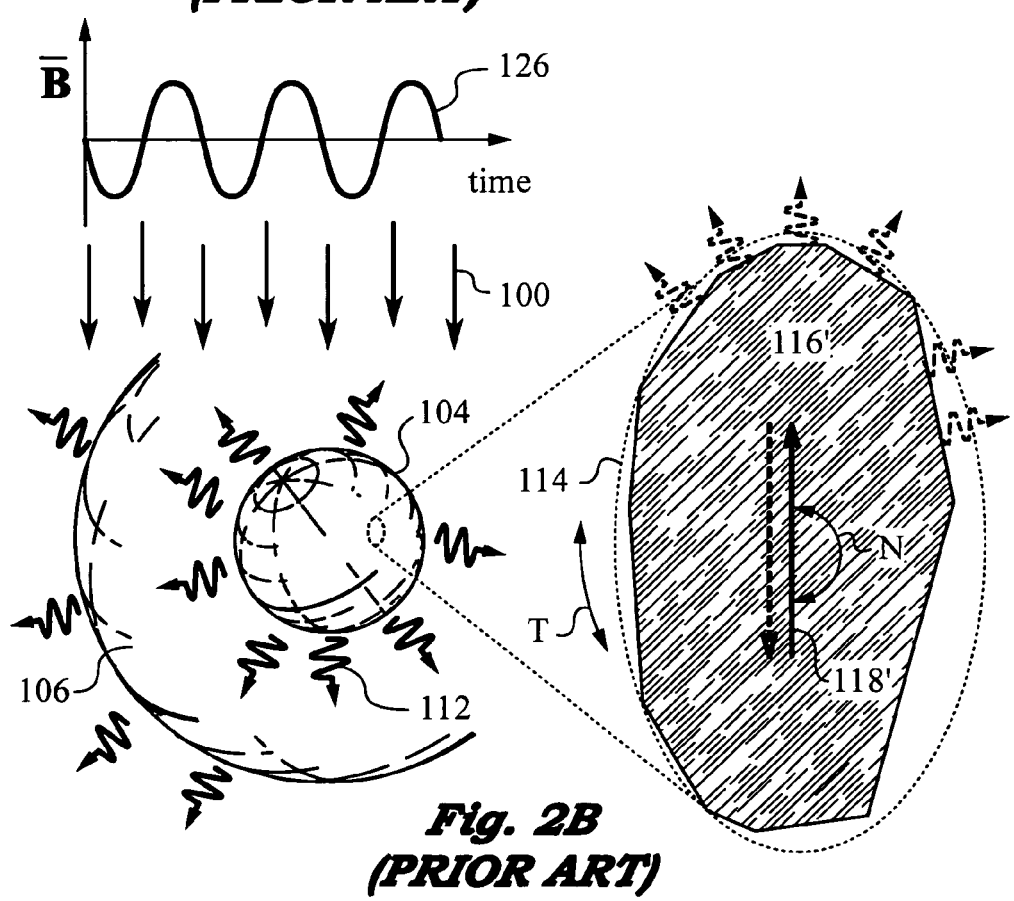

The inductive thermal response of magnetic material 104 is explained by schematic views presented in FIGS. 2A-B. FIG. 2A illustrates nanoparticle 102 when AMF 100 is absent or off. At this time, magnetic material 104, in this case a ferromagnetic material, is shown in detail in a first close-up 114. Specifically, material 104 has a number of permanent magnetic domains 116 each with a different overall dipole moment 118. Only three domains 116 are illustrated and only domains 116A, 116B are explicitly labeled along with their dipole moments 118A, 118B for reasons of clarity.

Dipole moment 118A is due to the alignment of individual magnetic dipoles 120 in domain 116A as indicated in close-up 122A of a portion of domain 116A. Similarly, dipole moment 118B is due to the alignment of magnetic dipoles 120' in domain 116B as indicated in close-up 122B. Note that moment 118A is exactly opposite to moment 118B. This is because dipoles 120 are due to right-handed bound charge motion while dipoles 120' are due to left-handed bound charge motion (also called bound current by those skilled in the art).

The reasons for ferromagnetic material 104 forming magnetic domains 116 are well understood and have to do with individual magnetic dipoles 120, 120' of material 104 attempting to stay in a low energy state or equilibrium state. However, as energy from the environment impinges on material 104 it perturbs the established dipole moments 118 and disrupts the lowest energy state. In other words, when energy is delivered to material 104 moments 118 tend to change.

Although complex in general, for the present purposes there are two mechanisms or modes that reorient moments 118 as energy increases. These mechanisms are known as Neel and Brownian relaxation, and they involve reorientation of moments 118 and particle rotational motion, respectively. These modes are a function of random thermal energy in the particle's surroundings that rotates the entire magnetic particle, and energy delivered by a magnetic field to which the particle is exposed. These two modes are indicated by corresponding circular arrows. Arrows N show possible reorientation of dipole moments 118. Arrow B shows particle rotation.

Of course, dipoles 120, 120' themselves produce magnetic fields. Therefore, there is a certain amount of magnetic dipole-dipole interaction tending to align adjacent dipoles even in the absence of any applied magnetic field. Also, dipoles 120, 120' generate random thermal energy causing the particle to rotate and interact with the environment, notably coating 106 and other surrounding materials.

FIG. 2B illustrates what happens when AMF 100 is turned on at an RF frequency 126. When AMF 100 is sufficiently strong, individual magnetic dipoles will tend to align with AMF 100. Thus, material 104 will tend to establish a single magnetic domain 116' with a total dipole moment 118' that flips at RF frequency 126 in an attempt to stay aligned with AMF 100. This flipping corresponds the first mode, namely Neel relaxation through reorientation of magnetic moment. It is shown by arrow N. In the case where magnetic moment direction is strongly coupled with the particle itself, due in part to a large value of magnetic anisotropy, and particle movement is possible due to a low viscosity of the surrounding medium, Brownian relaxation through particle rotation can occur in response to the magnetic field of AMF 100 as well. Brownian relaxation in the present case is indicated by arrow T. Of course, random thermal energy is also active, but no longer indicated in FIG. 2B. Therefore, the overall flipping of dipole moments and corresponding domains 116 as well as the particle's rotational motion is quite chaotic and not easy to represent in a simple drawing figure.

This overall domain flipping and rotational motion is the inductive thermal response of material 104 and is defined in terms of the two modes separately. The rotational motion of the particle is called Brownian mode heating. The reorientations of magnetic dipoles 120 forced by AMF 100, is called Neel mode heating. It is the joint contribution of both these modes that results in the inductive thermal effect or heating that hyperthermic solutions deploy for pathogen destruction.

Each mode has a characteristic relaxation time, namely a Brownian relaxation time $\tau_B$ and a Neel relaxation time $\tau_N$. The effective relaxation time $\tau_{eff}$ of magnetic material 104 is related to Brownian and Neel relaxation times $\tau_B$, $\tau_N$ by their parallel contribution as follows:

$$\frac{1}{\tau_{eff}} = \frac{1}{\tau_B} + \frac{1}{\tau_N}.$$

Now, since the inverse of effective relaxation time $\tau_{eff}$, or $1/\tau_{eff}$, is expressed per unit time it can be compared to frequency 126 of AMF 100. It is known that maximum inductive thermal response or maximum thermal energy 112 will be generated by material 104 due to both modes when material 104 is in a blocked state relative to frequency 126 of AMF 100, requiring that AMF 100 substantially exceed this inverse of effective relaxation time $\tau_{eff}$, or frequency $126 \gg 1/\tau_{eff}$.

Unfortunately, in the prior art solutions, thermal energy 112 is radiated in all directions. This causes collateral damage to healthy tissue, as already discussed in the background section. Prior art nanoparticles and frequencies of applied AMF have to be kept in a range to ensure slow heating and low emission of low thermal energy 112. For example, temperatures are maintained at about 46.5° C., or just sufficient to destroy mostly stationary eukaryotic cells such as cancer cells.

In addition, the radiation of thermal energy 112 in all directions results in attenuation of the maximum particle temperature rise that can be achieved. This is due to rapid rates of convective and conductive cooling of the particle, which in turn is an inevitable consequence of increased particle surface area through with convective and conductive cooling occurs. This limitation becomes increasingly apparent as particle size shrinks due to a reduction in the ratio of particle volume to surface area. Often, this inability to generate a sufficient maximum temperature rise necessitates that toxic concentrations of particles are used.

Present Improvements in Diagnostics and Hyperthermic Treatment

In contrast with the prior art, nanoparticle-sized magnetic absorption enhancers (MAEs) according to the present invention exhibit a controlled response to the magnetic field that permits safe application of much higher temperature transients and provides numerous other advantages. Before discussing the embodiments of invention, we will first define the terms as used in the present detailed description.

DEFINITIONS

The term "thermotherapy," as used herein, refers to the use of heat as a physical mechanism in the diagnosis and treatment of a given condition.

The term "condition", as used herein, refers to an illness, disease, or other medical problem.

The term "AMF" is an abbreviation for "alternating magnetic field". As used herein, an alternating magnetic field is defined as a magnetic field that changes its direction vector periodically. The rate of change of the direction vector corresponds to any periodically changing waveform, which may include, without limitation, a sinusoid, square, sawtooth, triangle, trapezoidal, or similar waveform. In addition the AMF may include, without limitation, the superposition of multiple periodic signals, a DC component of the signal, a variable frequency, a variable signal amplitude, a variable duty cycle, and a variable phase. The frequency of the AMF is preferably in the range of 1 khz to 100 Mhz. More preferably the frequency is between 20 kHz and 10 Mhz. More preferably still, the frequency is between 50 kHz and 2 Mhz. It is understood that in order to generate a magnetic field, an electro-magnetic field is created, or which a magnetic field is one part and an electric field is the other part.

The term "nanoparticle-sized", as used herein, refers to a particle of less than 1 µm. The shape of the particle may be, without limitation, hemisphere, shell (bowl-shaped), dome.

The term "coating", as used herein, refers to a material or combination of materials that are used to coat or embed the magnetic material of a nanoparticle-sized MAE. Such coatings are used to facilitate in-vivo transportation of the magnetic material. Some exemplary coatings include polyethylene glycol (PEG), $SiO_2$, dextran, silver and gold.

The terms "ligand", "targeting moiety", "functional group", "functional moiety", and "functional ligand", as used herein, refer to one or more molecules or compounds which are bound to a nanoparticle-sized MAE and which specifically bind to an antigen or other substance. These include substances such as antibodies, oligonucleotides, biotin, streptavidin, protein A, amines, carboxylates, and the like. Exemplary ligands are disclosed in Table 1.

The term "disease material", as used herein, refers to cells of pathogen-borne diseases. These include bacterial, viral, parasitic, and fungal cells. Exemplary disease materials are disclosed in Table 1.

The terms "functional group", "functional moiety", and "functional ligand" refer to specific groups of atoms within molecules that are responsible for the characteristic chemical reactions of those molecules.

The term "target", as used herein, refers to a substance which preferentially bind to a target. Exemplary targets include disease materials for which deactivation, disruption or description is desired. Exemplary targeting moieties and targets are disclosed in Table 1.

The term "marker", as used herein, refers to an antigen or other substance to which the targeting moiety preferentially binds. Exemplary markers are disclosed in Table 1.

The term "magnetic", as used herein, refers to a material that exhibits, depending upon its environment, one or more of diamagnetism, paramagnetism, ferromagnetism, antiferromagnetism, ferrimagnetism, and superparamagnetism. The material may be, without limitation, any magnetic material including nickel, iron, cobalt, gadolinium and their alloys. Exemplary magnetic materials include Fe (iron), $Fe_2O_3$ (maghemite), and $Fe_3O_4$ (magnetite).

The term "MAE" is an abbreviation for "magnetic absorption enhancer". As used herein, an MAE refers to a nanoparticle-sized entity that contains one or more magnetic materials, which may be embedded in one or more coatings and is bound to a targeting moiety.

The term "duty cycle", as used herein, refers to the fraction of time that the magnetic field is active in the period of the signal waveform to the period time of that signal waveform. The duty cycle may be continuously varied, resulting in a pulse-width modulated signal.

The term "diamagnetic", as used herein, refers to materials that have all paired electrons and thus have no net magnetic moment when not placed in the presence of an external magnetic field. When placed in a magnetic field, such materials will produce a magnetic field that opposes the externally applied field.

The term "magnetic", as used herein, refers to materials that have some unpaired electrons and thus have a magnetic moment that aligns with an externally applied magnetic field; the electrons align with the applied field.

The term "paramagnetic", as used herein, refers to materials with weak susceptibility to external magnetic fields and do not retain their magnetic properties when an external magnetic field is removed.

The term "ferromagnetic", as used herein, refers to materials that are highly susceptible to external magnetic fields and retain their magnetic properties when an external magnetic field is removed. These materials have permanent magnetic domains that are amplified in the presence of an external magnetic field as the external field aligns the magnetic moments of neighboring domains.

The term "superparamagnetic", as used herein, refers to particles roughly less than 300 nm that exhibit strong paramagnetic properties in the presence of an external magnetic field, but have to permanent magnetism in the absence of an external magnetic field.

The term "AC" and "ac", as used herein, refer to alternating current.

The term "DC" and "dc", as used herein, refer to direct current.

The term "chimeric", as used herein, refers to chimeric proteins in which at least the amino-terminal and carboxy-terminal regions are derived from different original polypeptides.

The term "specific binding", as used herein, refers to non-covalent interactions including, but not limited to those formed between antigens and their associated antibodies, bioreceptors and their associated ligands, anvidin-biotin interactions, hybridization between complementary nuclein acids and other related pairings. Further, specific binding refers to the situation in which one moiety recognizes and adheres to a particular second moiety, but does not substantially recognize or adhere to other moieties in the environment. Binding of two or more entities may be considered specific if the equilibrium dissociation constant is small under conditions employed.

The term "immunoglobins" and "antibodies", as used herein, refer to a polypeptide or group of polypeptides which are comprised of at least one binding domain. These can include recombinant proteins comprised a binding domain (including single-chain antibodies), as well as fragments, including Fab, Fab', F(ab)2, and F(ab')2 fragments. Any immunoglobin may be natural, partly synthetically derived or wholly synthetically derived. All derivate immunoglobins thereof, which maintain specific binding affinity are also included within this term. In addition, the term describes any protein having a binding domain that is homologous or largely homologous to an immunolgobin binding domain. An antibody may be monoclonal or polyclonal. An antibody may be a member of any immunoglobin class, including any human class (IgG, IgM, IgA, IgD, and IgE).

The term "antibody fragment," as used herein, refers to any derivative of an antibody that is less than full length and retains at least some portion of the full-length antibody's specific binding affinity. Such fragments include, but are not limited to, Fab, Fab', F(ab')2, scFv, Fv, dsFv diabody, and Fd fragments. Production of an antibody fragment may occur by multiple means familiar to those knowledgeable in the art. Mechanisms include fragmentation of an intact antibody through enzyme or chemical reactions or recombinant production through genetic encoding of a partial antibody sequence. Other mechanisms include synthetic antibody fragment or partial synthetic antibody fragment production. An antibody fragment may consist of either single chain or multi-chain linkages.

The term "mAb" is an abbreviation for "monoclonal antibody". As used herein, a monoclonal antibody refers to immunoglobulins of a particular type bind which all bind to the same antigen.

The term "polyclonal", as used herein, refers to a mixture of immunoglobulin molecules secreted against a specific antigen, each recognizing a different epitope.

The term "interacts", as used herein, refers to non-covalent associations between a targeting moiety and a specific target. Noncovalent interactions include, but are not limited to, hydrogen binding, Van der Walls interactions, hydrophobic interactions and the like.

The term "hyperthermia", as used herein, refers to the heating of a target at sufficient temperatures to cause the deactivation, destruction, or suppression of that target. The specific temperature rise necessary for this to occur will depend upon the many factors including, but not limited to, the specific target.

The term "transient", as used herein, refers to the change in a physical system that occurs over a short period of time. A thermal transient that causes a temperature change over a short period of time (dT/dt) is an exemplary transient.

The term "preparation", as used herein, refers to a material composition with suitable medium for delivery to a host. An exemplary preparation is a preparation of nanoparticle-sized MAEs.

The term "biocompatible", as used here, refers to materials that do not exhibit any significant toxic effect upon host cells. Such materials may be deemed biocompatible if their introduction to host cells results in minimal cell death and does not substantially induce unwanted adverse effects in-vivo.

The term "biodegradable", as used herein, refers to materials, compounds, or complexes that can be broken down by cellular host cells into sub-components that do not exhibit any significant toxic effect on the host cells.

The terms "host", "subject", "individual", and "patient", as used herein, generally refer to any recipient of a diagnostic method, a prognostic method, or a therapeutic method to be provided according to the instant invention. An exemplary host would refer to an animal or plant that is infected by an infectious agent. This host may be, without limitation, humans and non-human primates such as chimpanzees and other apes and monkey species, farm animals such as cattle, sheep, pigs, goats and horses, domestic animals such as dogs and cats, laboratory animals including rodents such as mice, rats, rabbits and guinea pigs, and the like.

The terms "treatment" and "treating," as used herein, refer to providing a prophylactic or therapeutic pharmacologic or physiologic effect from the disclosed technology. In the case of prophylactic treatment, there is an intention to prevent a disease or symptom of disease from developing in a subject who may be predisposed to the disease, but has not yet been diagnosed as having it. In the case of a therapeutic effect, the treatment may inhibit the disease, i.e., arrest its development, or it may relieve the disease, i.e., cause a regression of disease. Such treatment includes treatment of any host where exemplary hosts include mammals, and particularly humans.

The term "cytokine", as used herein, refers to a protein secreted by immune cells or other cells for the purpose of an immune response. Cytokines include interleukins.

The term "chemotherapeutic agent", as used herein, refers to a substance that is chemically derived and relies upon its chemical activity to treat disease. An antibiotic is an exemplary chemotherapeutic agent.

The reference to the "size" of a nanoparticle is in reference to the length of the largest straight dimension of the nanoparticle. The size of a spherical nanoparticle is its diameter.

The terms "infectious disease" and "infection," as used herein, refer to a pathological or non-pathological state resulting from the invasion of the body by pathogenic or non-pathogenic microorganism. Exemplary infectious agents are disclosed in Table 1.

The term "infectious agent," as used herein, refers to a pathogenic or non-pathogenic microorganism. Exemplary infectious agents are disclosed in Table 1.

The phrase, "agent to be delivered" or "active ingredient", refers to any substance that can be delivered to a tissue, cell, or subcellular location. The agent may be, but is not limited to, a biologically active agent that has activity in a biological system and/or organism. For example, if a substance delivered to a given organism has some biological effect on that organism, it is considered to be a biologically active agent.

The term "amino acid," as used herein, refers to any compound or substance that can be incorporated into a polypeptide chain. This includes, but is not limited to, an amino acid with general structure $H_2N—C(H)(R)—COOH$.

The term "animal", as used herein, refers to any member of the animal kingdom. This includes, in some embodiments, humans of any stage of development or non-human animals. Such non-human animals include mammals (e.g., a rodent, a mouse, a rat, a rabbit, a monkey, a dog, a cat, a sheep, cattle, a primate, and a pig). Other non-human primates include, but are not limited to, birds, reptiles, amphibians, fish, insects, and/or worms. Any animal may be transgenic, genetically-engineered or a clone.

The term "in-vitro" as used herein, refers to events that occur in an artificial environment, e.g., in a test tube, reaction vessel, cell culture etc., rather than within an organism.

The term "in-vivo," as used herein, refers to events that occur within an organism, e.g., in a human or non-human animal.

The term "protein," as used herein, refers to a polypeptide (string of two or more amino acids links to one another by peptide bonds). Such amino acids may be natural, synthetic or combinations thereof. Proteins may include non-amino acid moieties including glycoproteins, proteoglycans, and proteins that may have been processed or modified. A protein may be a complete polypeptide chain or portion thereof or a multi-peptide chain. Such polypeptides may contain L-amino acids, D-amino acids, or both and may contain a range of amino acid modifications or analogs known in the art. Such modifications include, but are not limited to, terminal acetylation, amidation etc.

The term "excipient," as used herein, refers to an inactive substance used as a carrier for the active ingredients of a medication. This carrier may be necessary due to the fact that the "active" ingredient may not be readily absorbed or easily administered to a patient. The use of an excipient may further be to stabilize the active ingredient to ensure its continued biological activity and improve its shelf-life. To allow for convenient and accurate dosage, excipients may also be used to bulk up formulations that contain very potent active ingredients.

DESCRIPTION OF THE EMBODIMENTS

According to the invention, a nanoparticle-sized magnetic absorption enhancer (MAE) is designed to exhibit a controlled response to a magnetic field. The main aspects of the invention and its preferred embodiment will be explained in relation to FIG. 3, which illustrates an embodiment in which nanoparticle-sized MAEs 202 according to the invention are deployed in an apparatus 200 for inducing transient hyperthermia. The details of the structure of MAE 202 will be explained in reference to the three-dimensional diagram of FIG. 4.

We refer first to MAE 202 as shown in FIG. 4. MAE 202 has a magnetic material 204 chosen to have an inductive thermal response to a magnetic field, and specifically an alternating magnetic field. Suitable magnetic materials 204 have already been listed above. In the present case, material 204 is $Fe_2O_3$.

Material 204 is embedded in a coating 206 as a single part or as one piece. Coating 206 itself is designed to conform to a particular shape 208. Thus, the three-dimensional shape of coating 206 imposes the overall geometry or shape 208 on MAE 202. According to the invention, shape 208 is a hemisphere, a shell or a dome. In this embodiment, shape 208 is a hemisphere.

A person skilled in the art will recognize that many techniques are available for producing hemispherical shapes of nano-scale. Any of these may be employed in achieving shape 208. Some exemplary teachings are contained in the following references: H. Krishna, C. Miller, L. Longstreth-Spoor, Z. Nussinov, A. K. Gangopadhyay, and R. Kalyanaraman, "Unusual size-dependent magnetization in near hemispherical Co nanomagnets on $SiO_2$ from fast pulsed laser processing", J. Appl. Phys. 103, 073902 (2008); Y. Lu, G. L. Liu, J. Kim, Y. X. Mejia, and L. P. Lee, "Nanophotonic Crescent Moon Structures with Sharp Edge for Ultrasensitive Biomolecular Detection by Local Electromagnetic Field Enhancement Effect," *Nano Lett., Vol.* 5, No. 1. (2005), pp. 119-124; S. Yun, B. Sohn, J. Jung, W. Zin, J. Lee, O. Song, "Tunable Magnetic Arrangement of Iron Oxide Nanoparticles in Situ Synthesized on the Solid Substrate from Diblock Copolymer Micelles", Langmuir. 2005 Jul. 5; 21(14):6548-52; H. Krishna, C. Favazza, A. K. Gangopadhyay, and R. Kalyanaraman, "Functional Nanostructures through Nanosecond Laser Dewetting of Thin Metal Films", JOM, Volume 60, Issue 9, pp. 37-42.

Because MAE 202 has to be biocompatible, coating 206 is made of a suitable biocompatible material 210. Advantageous choices of material 210 include $SiO_2$, dextran, gold, silver and polyethylene glycol. In general, however, material 210 can be any one or a combination of materials selected from the group of biodegradable polymers, modified dextran coatings, cross-linked dextran coatings, polylactide/polyglycolide copolymers, poly(orthoesters), poly(anhydrides), microemulsions, liposomes, and thermally sensitive lyposomes (LTSLs, HTSLs). In the present embodiment, material 210 is dextran.

Figure 3:
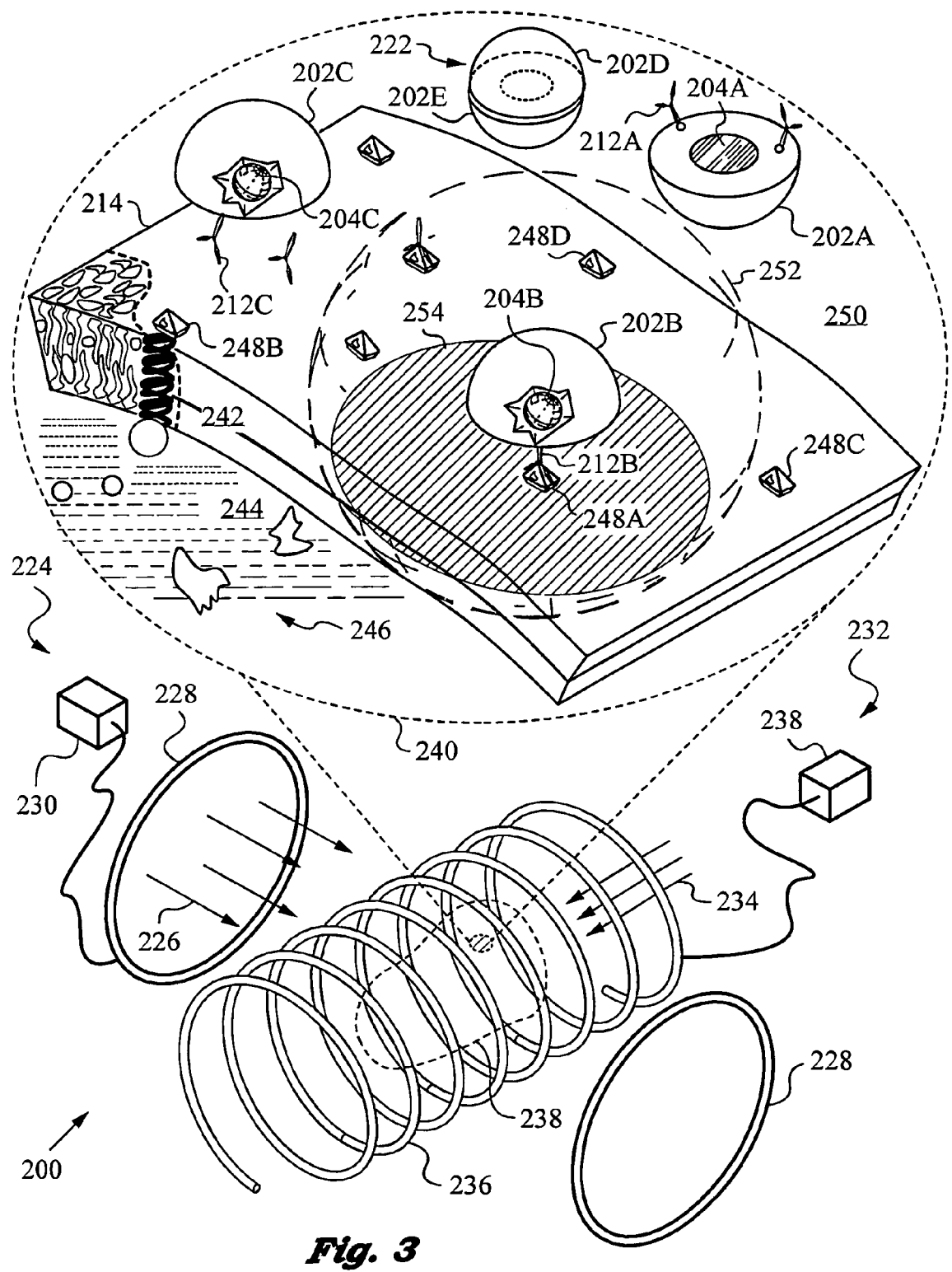
FIG. 3 is a three-dimensional schematic view illustrating the deployment of MAEs in accordance with the invention.

A targeting moiety 212 for specifically binding MAE 202 to a pathogen target 214, see FIG. 3, is provided on a face 216 of hemisphere 208. In fact, two targeting moieties 212 are provided on face 216. It is understood by those skilled in the art, that a single targeting moiety 212 may be sufficient. In other cases, it may be possible to accommodate two or more targeting moieties 212 on face 216. Furthermore, the use of multiple targeting moieties 212 on a single MAE 202 may be desirable to increase affinity of MAE 202 for pathogen target 214.

Targeting moieties 212 are selected for their ability to selectively bind MAE 202 to pathogen target 214. Thus, in general, moieties 212 will be antibodies or other entities that can recognize and selectively bind to pathogen target 214, such as peptides, aptamers and the like. In the present invention, preferred targeting moieties 212 are selected from the group consisting of CCR5, TNX-355, KD-247, PRO140, PRO542, HGS004, HGS101, Bavituximab, Ostavir, mAb F598, tefibazumab, Pagibaximab, Veronate, Aurograb, 0657nl (V710), AP4-24 H11, TI-57, Rituximab, TI-23, HCMV37, CR3014, CR3022, AB68, AB65, HuMax-HepCl, ligands targeting intracellular and extracellular components of *Staphylococcus* spp. known to cause Staphylococcal infection, *Babesia* spp. known to cause babesiosis, *Ehrlichia* spp. known to cause ehrlichiosis, *Anaplasma* spp. known to cause anaplasmosis, *Bartonella* spp. known to cause Bartonellosis, and *Borrelia* spp. known to cause Lyme Disease including *Borrelia burgdorferi, Borrelia afzelii, Borrelia garinii* and *Borrelia valaisiana*.

In the present embodiment, both targeting moieties 212 are attached to coating 206 of MAE 202. In general, attachment of targeting moiety 212 is accomplished with the aid of a bond 218. Bond 218 depends on the type of targeting moiety 212 being used, as will be appreciated by those skilled in the art. Thus, in general, bond 218 relies on bonding mechanisms such as passive absorption, covalent coupling, hydrogen bonding, secondary or tertiary amine linkage, amide linkage, Schiff base linkage, isourea linkage, thiourea linkage, carbamate linkage, ether linkages, thioether linkages, strept(avidin)-biotin interactions, hydrazone linkages, SPDP crosslinker coupling.

According to the invention, shape 208 is selected to produce a controlled mechanical response of MAE 202 to the magnetic field. It is both the inductive thermal response of material 204 and the controlled mechanical response of entire MAE 202 that constitute the controlled response according to the invention. The total controlled response must be well behaved when the magnetic field is present or applied, and absent or turned off.

In fact, it is important that shape 208 of one MAE 202 be complementary to that of another MAE 202 in the sense that their controlled mechanical response is an interaction between them. By virtue of their shape 208, hemispherical MAEs 202 have this property.

FIG. 5A is a three-dimensional view illustrating the first stage of the intended mechanical response of two MAEs 202D, 202E having complementary hemispherical shapes. When not bound to pathogen target 214, MAEs 202D, 202E are free to move. In this free state, they will tend to polarize and self-align, as indicated by arrow 220, in a static external magnetic field, thereby executing the first step of the controlled mechanical response.

It should be noted, that spontaneous self-organization of ferromagnetic nanoparticles behind the self-alignment of MAEs 202D, 202E can be explained by two forces. First, Van der Walls interactions induce spherical aggregation of particles in the absence of an externally applied magnetic field. Such aggregation is a function of particle distance and particle coating thickness with apparent interparticle attraction energy at distances proportional to metal core size (Université Pierre et Marie Curie, Laboratoire des Matériaux Mesoscopiques et Nanométriques, U.M.R. 7070, BP 52, 4 place Jussieu, 75005 Paris, France). This places obvious restrictions upon the maximum particle coating thicknesses. Second, dipole-dipole interactions induce particle self-organization with apparent interparticle attraction energy at distances proportional to metal core size in the presence of an applied magnetic field with field strength preferably between 1 mT and 10 T and more preferably between 10 mT and 5 T and more preferably still between 50 mT and 3 T (Iakovenko S A, Trifonov A S, Giersig M, Mamedov A, Nagesha D K, Hanin V V, Soldatov E C, Kotov N A, "One and two-dimensional arrays of magnetic nanoparticles by the Langmuir-Blodgett technique", Adv Materials, 1999: 11(5):388-392; Petit, C., Taleb, A. and Pileni, M. P., "Self-organization of Magnetic Nano-sized Cobalt Particles", Adv. Mater. 10, 259-261, 1998).

FIG. 5B illustrates the second step of the mechanical response between MAEs 202D, 202E. At this point, static magnetic field is applied. In response, MAEs 202D, 202E interact and their interaction results in the formation of a sphere 222. Once sphere 222 forms, targeting moieties 212 may stick out or be trapped between MAEs 202D, 202E.

The advantage of sphere 222 formed of complementary hemispheres 208 in this manner, is that it insulates the surroundings from the thermal energy generated by inductive thermal response that is generated when an alternating magnetic field is applied to MAEs 202D, 202E. The great value of this advantage of the invention will become apparent by examining the apparatus 200 employing MAEs 202 whose shape 208 is hemispherical, and the operation of apparatus 200.

Referring back to FIG. 3, we see that apparatus 200 for inducing transient hyperthermia in pathogen target 214 has an arrangement 224 for generating an alternating magnetic field (AMF) 226. In this embodiment, arrangement 224 is constituted by a set of magnetic coils 228 and a corresponding control mechanism 230. An additional arrangement 232 for generating a static magnetic field 234 is also provided. Arrangement 232 is constituted by a set of magnetic coils 236 and its corresponding control mechanism 238. Note that the relative orientation of magnetic coils 226, 234 is orthogonal in this embodiment. This, however, is not required and other orientations are permissible, as will be clear to those skilled in the art.

Magnetic coils 228 and 236 are centered about a three-dimensional region 238 generally indicated by a dashed line. Region 238 is the location of a host or subject, not shown, that contains pathogen targets 214 to be diagnosed and/or treated by hyperthermia. A close-up 240 of a small portion of region 238 indicates illustrates a cell wall 242 of just one pathogen target 214 for easier visualization and explanation.

Pathogen target 214 is in fact a prokaryotic cell, which requires a temperature in excess of 55° C. for durations of up to 10 seconds to ensure destruction or rupturing of its cell wall 242. In other words, since the host homeostatic temperature is about 37° C. a temperature transient of more than 18° C. for up to 10 seconds has to be applied to cell wall 242. The inner region of cell 214 contains a cytoplasm 244 with intracellular constituents 246 such as proteins, macromolecules and small molecules.

MAEs 202, and specifically MAEs 202A-E are shown in the extracellular matrix (ECM) 250 of the host. (Methods for administering preparations of MAEs 202 and guiding them in the host to region 238 where pathogen cells 214 reside, whether in perfused or ischemic regions are discussed below.) At the time shown in FIG. 3, targeting moiety 212B or antibody of MAE 202B has bound with pathogen target 214. In particular, antibody 212B has undergone specific binding with an antigen 248A in cell wall 242. Meanwhile, MAEs 202A, 202C are still floating freely with their antibodies 212A, 212C unbound. MAEs 202D, 202E have executed the desired mechanical response by interacting and forming sphere 222, which shields their magnetic material 204 from the surrounding space.

In this state, apparatus 200 could turn on alternating magnetic field 226 to cause material 204 in all MAEs 202 to exhibit their inductive thermal response and generate thermal energy. It is preferable, however, to first turn on static magnetic field 234 to cause the desired mechanical response between unbound MAEs 202A, 202C such that the interaction between their complementary shapes also forms a sphere. That is because in the free and unbound state, thermal energy generated by MAEs 202A, 202C would be emitted predominantly from their open faces and cause collateral damage to healthy tissue in ECM 250 of the host.

Once all unbound MAEs 202 have undergone the desired mechanical response and formed spheres, their configuration is safe to the host. That is because in the spherical configuration most thermal energy generated by magnetic material 204 will be contained within the spheres. In other words, the spheres formed of complementary hemispherical shapes will act to contain most of the inductive thermal response produced when AMF 226 is applied.

Coils 228 apply AMF 226 under the direction of control mechanism 230. AMF 226 provokes the second portion of the controlled response of MAEs 202, namely the inductive thermal response. In accordance with the physical mechanisms explained above, AMF 226 results in generation of thermal energy due to Brownian and Neel mode heating. Preferably, the frequency f of AMF 226 is set by mechanism 230 to be above the inverse of the effective relaxation time $\tau_{eff}$, or $f > 1/\tau_{eff}$.

In fact, it is generally preferable for f to be significantly higher than $1/\tau_{eff}$. That is because maximum heating occurs when f of AMF 226 is substantially higher than the inverse of the effective MAE 202 relaxation time $\tau_{eff}$. More precisely, when frequency f of AMF 226 is substantially higher than the inverse of the effective relaxation time $\tau_{eff}$, magnetic material 204 of MAE 202 is in a "blocked" state.

In this "blocked" state a substantial amount of thermal energy is generated by magnetic material 204. In contrast, when frequency f of AMF 226 is substantially less than the inverse of MAE 226 effective relaxation time $\tau_{eff}$, magnetic material 204 is considered "unblocked" and rotates freely with negligible thermal energy dissipation into the environment.

Referring back to FIG. 3, it is clear that because of shielding or confinement of thermal energy by unbound MAEs 202D, 202E that form sphere 222, it is possible and indeed advantageous to set a high rate of inductive thermal response by magnetic material 204 in the "blocked" state. Unlike unbound MAEs 202D, 202E that will not emit much thermal energy, MAE 202B will emit considerable thermal energy from its magnetic material 204B (partially shown) predominantly in the direction of pathogen cell 214 to which it is bound by its targeting moiety or antibody 212B at antigen 248A. In fact, within a thermal length describing a spherical region or "blast area" 252 around MAE 202B, a zone 254 of cell wall 242 oriented generally parallel to the face of MAE 202B and intersecting spherical region 252 will receive a very substantial amount of thermal energy. Thus, cell wall 242 can be ruptured or destroyed, hence also destroying pathogen cell 214.

As noted above, since pathogen cell 214 is a prokaryote, tuning and applying of AMF 226 by coils 228 to yield a transient of 18° C. for a duration of up to 10 sec in zone 254 is preferred to destroy cell 214. Of course, as also noted above, it is preferable to wait with the administration of AMF 226 until MAEs 202A and 202C have also undergone the controlled mechanical response and formed a sphere to contain the thermal energy generated by their magnetic material 204A, 204C.

It is the hemispherical shape 208 of MAE 202 and the placement of antibodies 212 on its face that permits to direct the thermal energy primarily at pathogen target 214. Of course, the hemisphere is not the only shape that coating 206 may enforce on MAE 202 and accomplish this advantageous result. FIGS. 6A-E illustrate a few alternative embodiments for MAEs that will also permit to obtain the desired mechanical response. Namely, to confine the thermal energy when joined together and delivering it predominantly to the pathogen target when bound to it.

Figure 6A:
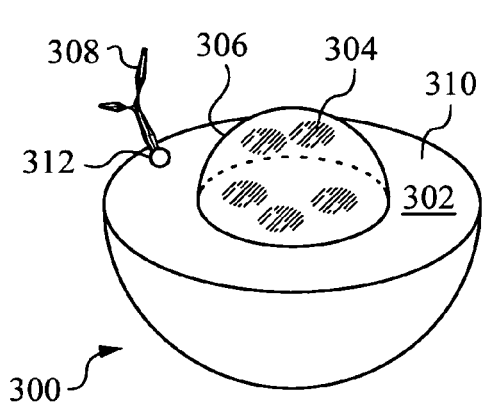

FIG. 6A shows an MAE 300 with a coating 302 that embeds a magnetic material 304 and conforms to the shape of a dome 306. A targeting moiety 308 is attached to a flat flange 310 of dome-shaped MAE 300 by a bond 312. It should be noted that material 304 may be exposed or under a thin layer of coating 302. Further, several methods exist for achieving proper attachment of targeting moiety 308 to flat flange 310 of asymmetric MAE 300. Indeed, applying these methods, most of which were specifically designed for working with asymmetric nanoparticles, will frequently be required for MAEs of the invention. That is because MAE shapes taught in the present invention are asymmetric; namely hemisphere, shell and dome. A person skilled in the art will find appropriate methods disclosed in WO/2005/049195 by Etienne Duguet et al., entitled "Unsymmetrical Inorganic Particles, and Method for Producing the Same". Additional teaching is found in U.S. Published Patent Application 2009/0280188 to C. A. Mirkin et al., entitled "Asymmetric Functionalized Nanoparticles and Methods of Use".

Figure 6B:
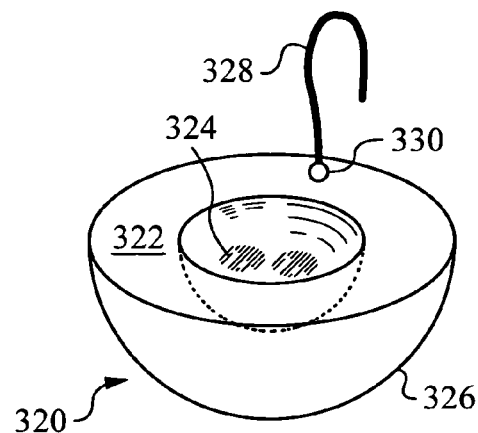

FIG. 6B illustrates an MAE 320 whose coating 322 embeds a magnetic material 324 and conforms to the shape of a bowl or shell 326. A targeting moiety 328, this time in the form of an aptamer, is attached near the opening of shell 326 by a bond 330. Once again, material 324 may be embedded deep within coating 322 or may be exposed inside the "bowl" of MAE 320. It should be noted, that the exemplary shapes of dome and shell are complementary in the sense that together they can form spheres or nearly spherical forms. However, individually, their shapes are non-spherical.

Figure 6C:
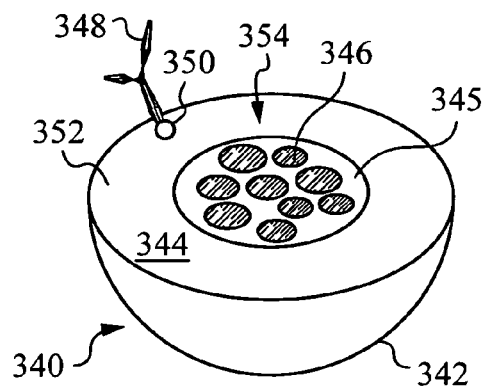

Another MAE 340 whose shape 342 is hemispherical is illustrated in FIG. 6C. MAE 340 has an external coating 344 that embeds a core coating 345. In this embodiment, coating 344 is made of dextran or polyethylene glycol (PEG). Coating 344 surrounds a core coating 345 that embeds a magnetic material 346. Coating 345 in this embodiment is made of $SiO_2$. In this configuration, coating 344 isolates core coating 345 from external molecules, tissues, or other biological entities present in the host or patient. A targeting moiety 348 is attached via bond 350 to face 352 of MAE 340.

Magnetic material 346 is embedded in core coating 345 but not in a single part as in the above embodiments. Instead, material 346 is distributed in a number of individual magnetic crystals 354. Preferably, each magnetic crystal 354 is small enough to behave as a single magnetic domain. The use of multiple magnetic crystals 354 increases the aggregate anisotropy of material 346 of MAE 340. This, in turn, decreases the Neel relaxation time from approximately $10^{-9}$ sec down to $10^{-6}$ sec. Such decrease is advantageous for the purposes of the present invention. It leads to a blocked particle starting with low AMF frequencies and thus generates a greater number of Neel mode power losses.

Figure 6D:
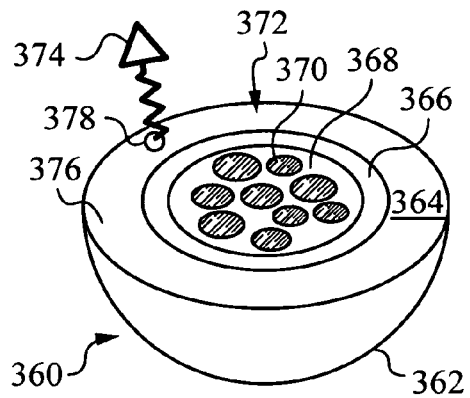

FIG. 6D shows another MAE 360, whose shape 362 is hemispherical. MAE 360 has an external coating 364 or particle coating, an intermediate coating 366, and a core coating 368. Magnetic material 370 is embedded in core coating 368. As in the previous embodiment, material 370 is distributed in a number of individual magnetic crystals 372. Therefore, material 370 is designed to provide sufficient structure to hold the matrix of crystals 372. An advantageous materials choice for material 370 is PEG or dextran.

The use of intermediate coating 366 may be to provide extra thermal insulation of core 368 in which material 370 is embedded. Such insulation from external environment can aid in increasing the rate of heating, i.e., it can be used to increase the rate of inductive thermal response and hence the rate of generation of thermal energy. This allows one to achieve a higher maximum temperature. Optionally, intermediate coating 366 may be used for the purpose of increasing the thermal capacitance of MAE 360 to increase the resistance-capacitance (RC) time constant and to thus modify the rate of heating. A good choice for the material of coating 366 is $SiO_2$.

A targeting moiety 374 is bound to face 376 of MAE 360. In this embodiment, targeting moiety 374 is a peptide. Peptide 374 is attached to face 376 by a corresponding bond 378.

Figure 6E:
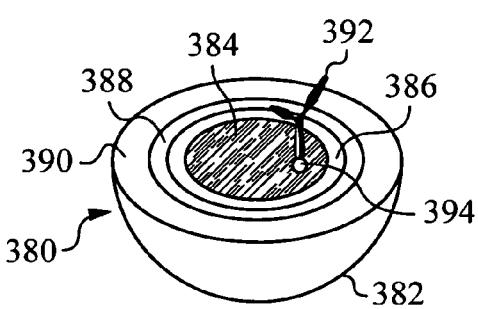

FIG. 6E depicts an MAE 380 whose shape 382 is hemispheric. MAE 380 has a magnetic material 384 embedded in a core coating 386 in a single piece. MAE 380 also has an intermediate coating 388, that may be used for the same purposes as in MAE 360; namely for improved thermal properties. External coating 390 encapsulates MAE 380.

In this embodiment, a targeting moiety 392 is attached by a bond 394 directly to magnetic material 384. Moiety 392 is an antibody. Attachment of antibody 392 directly to material 384 will improve delivery of thermal energy to pathogen target when antibody 392 is bound to its corresponding antigen on the pathogen target.

Clearly, a person skilled in the art will appreciate that the above exemplary embodiments merely outline some structural possibilities.

Additional coatings can be used to further tune the thermal properties of any of the above-described MAEs.

Figure 6F:
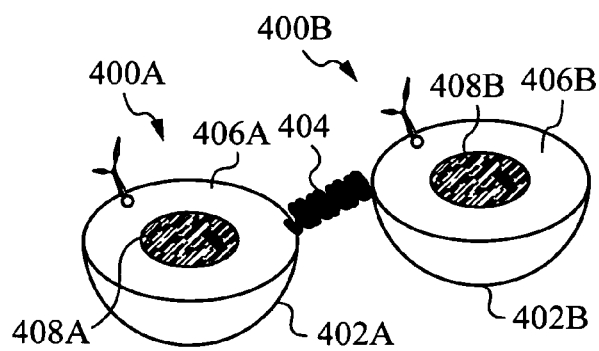

Irrespective of shape and structure selected for an MAE, FIG. 6F illustrates a manner of controlling the distance between MAEs to achieve the most advantageous results in accordance with the invention. Specifically, FIG. 6F illustrates linking of two MAEs 400A, 400B that both have hemispherical shapes 402A, 402B by a flexible linker 404. Linker 404 is attached to coatings 406A, 406B, that embed magnetic materials 408A, 408B, respectively. The molecules or compounds constituting linker 404 can include hydrophobic molecule chains.

Linking is preferred because it increases the desired mechanical response between MAEs 400A, 400B. Because of linker 404, maximum inter-particle distances between MAEs 400A, 400B is controlled such that interparticle attraction energy from a combination of Van der Walls interactions and dipole-dipole interactions is sufficient to induce MAE aggregation. Obviously, interparticle attraction energy from dipole-dipole interactions dominate over the comparably weak Van der Walls interactions.

Further, the presence of linker 404 promotes spontaneous particle self-assembly into long bands or particle clusters. Such self-assembly facilitates greater particle heating when MAEs 400A, 400B are bound to a pathogen target. At the same time, it helps to contain thermal energy produced by free MAEs that formed spheres via the desired mechanical response described above.

FIG. 7 presents a diagram illustrating the preferred embodiment in which MAEs 410 that are linked by flexible linkers 412 are employed against a pathogen target 414. FIG. 7 shows specific MAEs 410A, 410B, 410C, 410E, 410F, 410G and 410H linked in pairs by corresponding flexible linkers 412A, 412B, 412C and 412D. All MAEs 410 are dome shaped and have targeting moieties 416 in the form of antibodies. FIG. 7 shows specific antibodies 416A, 416B, 416C, 416E, 416F, 416G and 416H attached to their respective MAEs 410A, 410B, 410C, 410E, 410F, 410G and 410H. All antibodies 416 are attached at open faces of MAEs 410 in accordance with any of the above-mentioned methods for attaching them to asymmetric nanoparticles. More specifically, antibodies 416 are attached directly to magnetic material of MAEs 410. Furthermore, antibodies 416 are selected for specifically binding to antigens 418 present in a cell wall 420 of pathogen target 414. Only two particular antigens 418A and 418B among the many antigens 418 that are found in cell wall 420 are shown in FIG. 7 for reasons of clarity.

Once MAEs 410 find themselves in a region 422 where pathogen target 414 resides, some will bind to pathogen target 414. In the present case, MAE 410G is bound to pathogen target 414. The actual bond is formed between its antibody 416G and antigen 418A of pathogen target 414. By virtue of being yoked or bound to MAE 410G by linker 412D, MAE 410H is also properly positioned to deliver thermal energy to pathogen target 414.

In the meantime, other MAEs 410 are not bound to pathogen target 414. Normally, such unbound MAEs present a threat to surrounding host tissue. That is because when AMF is applied they will likely emit thermal energy not aimed at pathogen target 414 but rather at healthy tissue in region 422. However, because of their dome shape and due to linkers 412, MAEs in accordance with the invention avoid such collateral damage.

In particular, MAEs 410A, 410B are already undergoing a desired mechanical response of self-orienting as indicated by arrow S. MAEs 410C, 410D have progressed further along in this desired mechanical response and aligned. MAEs 410E, 410F have completed the mechanical response and formed a spherical shape 424. In this case, spherical shape 424 is a spherical dimer composed of MAEs 410E, 410F yoked by linker 412C. That is because MAEs 410E, 410F are dome shaped and cannot close completely to form a sphere.

As explained above, this spherical configuration of complementary MAE shapes will help to contain the thermal energy when AFM is applied and their magnetic material produces the inductive thermal response. Note that in embodiments where the MAEs are shaped as shells or bowls, the formation of spherical shapes during their interaction is possible, just as in the case of hemispherical MAEs.

In addition, a static magnetic field can be provided. The static field can be tuned in direction and magnitude to control the activity of the MAE and further promote the desired mechanical response of unbound MEAs 410 to interact and form spherical dimers. A suitable arrangement of coils for applying AFM and the static magnetic field is shown in the embodiment of FIG. 3.

A preferred apparatus 500 for inducing transient hyperthermia in pathogen targets using any of the above-described MAEs, is shown in FIG. 8 in an exploded three-dimensional schematic view. In fact, apparatus 500 takes advantage of the magnetic coils in an NMR machine (also known as Magnetic Resonance Imaging or MRI device), i.e., NMR coils including the coils that generate an alternating magnetic field. Thus, FIG. 8 shows an integrated treatment and diagnosis system 500 that integrates NMR (MRI) for diagnosis with RF hyperthermia for treatment.

A patient, 502 is placed in the center of apparatus 500. Entire patient 502 may be placed in device 500 or a subset of patient 502. The portion of apparatus 500 where patient 502 is placed has a generally circular cross-section like a tube, donut, or the like.

Apparatus 500 has an arrangement 504 for producing magnetic fields. Arrangement 504 is made of a several solenoids that fit within one another. In particular, a first solenoid 506 is used as a transmit-receive coil for the purpose of either emitting RF magnetic pulses or receiving magnetic pulses for performing an NMR scan. Optionally, first solenoid 506 may be specifically used for the purpose of receiving an RF magnetic pulse and a second solenoid is used for transmitting RF magnetic pulses. Following these are two or optionally three solenoids 508 and 510 used as gradient coils for transmitting gradient pulse sequences (Gx;Gy;Gz) for the purpose of performing and NMR scan.

Following these solenoids is the main resistive or superconducting electromagnet 512 for delivering either a static magnetic field ($B_o$) for performing an NMR scan or an AMF for the purpose of performing RF hyperthermia treatment in accordance with the invention. Optionally, an NMR scan may occur using an AMF field and hyperthermia may occur using the static field as well.

In this embodiment, device 500 may transition rapidly from NMR scanning to hyperthermia treatment. In the hyperthermia treatment mode, switches 514 electrically connecting AMF matching network 516 to magnet coil 512 and disconnect MRI DC power supply 518 from magnet coil 512. AMF power supply 520 generates an AC waveform using a waveform generator 522 and bandpass, or lowpass or highpass filter 524. The AC waveform passes through AMF matching network 516. Matching network 526 is designed to match the input impedance of electromagnet 512 with the output of the AMF power supply 520.

AMF power supply 520 is designed similar to inducting heating devices designed by Ameritherm, MSI Automation, Huettinger Electronics or related companies. Specifically, high-power semiconductor-based MOSFET devices are used to deliver high currents with moderately high voltages to electromagnet 512. In this way, AMF power supply 520 may be viewed as an AC current source. The currents delivered during operation will be between 100 A and 100 kA, and more preferably between 300 A and 5 kA, and more preferably still between 1 kA and 2 kA. A high-Q tank resonance LC circuit is created with resonant frequency $\frac{1}{2}\sqrt{LC}$ where L refers to the inductance of coil 512 and C refers to the fixed or optionally variable capacitance of AMF matching network 516.

In hyperthermia mode, gradient coils 508, 510, and RF coil 506 will be electrically disconnected from NMR console 526. This is ensured by a control mechanism 528, in this case a computer system connected to MRI DC power supply 518, waveform generator 522 and NMR console 526. Also, all coils should preferably be fluid cooled to prevent undesirable self-heating of the coils.

As shown in this embodiment, MRI DC power supply 518 and AFM matching network 516 may both be connected to electromagnet 512. A common ground is shared, which may optionally be a floating ground, between MRI DC power supply 518, AMF power supply 520 and AMF matching network 516 to ensure device circuit interoperability and electrical safety. A DC current can be applied to electromagnet 512 at the same time that AMF power supply 520 applies an AMF.

The purpose of simultaneously applying a DC and AC current to electromagnet 512 may be to utilize magnetic field gradients to selectively excite subsets of magnetic particles, i.e., MAEs, present in patient 502. Specifically, it has been shown that the energy barrier to nanoparticle rotation can be advantageously modified by applying a static magnetic field to the nanoparticle-sized MAEs.

Utilizing gradient coils 508 and 510, the strength of the static magnetic field generated by electromagnet 512 may be either attenuated or amplified in target region of patient 502. Similar to the techniques used for MRI scanning, in which the proton precession rate is a function of the Larmor frequency, the energy barrier to nanoparticle relaxation may be a function of the strength of the static magnetic field of electromagnet 512 and the gradient pulse sequences (Gx;Gy;Gz) emitted by gradient coils 508 and 510. Utilizing the simultaneous delivery of both AMF and static fields generated by electromagnet 512, one may selectively induce hyperthermia in a subset of nanoparticles in patient 502. In doing this, mode gradient coils 508, 510 and first solenoid 506 will not be electrically isolated from NMR console 526 and therefore signal amplification or attenuation may be necessary to dissipate eddy currents that form in such coils during hyperthermia treatment.

In NMR imaging mode, switches 514 electrically disconnect AMF power supply 520 and AMF matching network 516 from electromagnet 512, and connect MRI DC power supply 518 to electromagnet 512. In this mode, electromagnet 512 is subject to a DC current that passes through it and creates a static magnetic field $B_o$. Gradient coils 508, 510 and first solenoid 506 are then used to create MR pulse sequences for the purpose of performing MR imaging. Such MR imaging may be used for biosensing or MR thermometry. NMR console 526 makes use of a gradient system 530, digital transmitter system 532, and digital receiver subsystem 534 for the purpose of performing MR scans. The requisite connection and switching of systems 530, 532 and subsystem 534 is not explicitly shown, but is well known to those skilled in the art.

Computer system 528 and NMR console 526, together forming a control system, are used to optimize treatment to ensure safety and efficacy. Specifically, this control system is used to ensure that magnetic nanoparticles present in the host, i.e., patient 502, reach temperature transients and durations in accordance with the invention to induce death in the pathogen target. Further, the control system may measure the temperature of tissue of patient 502 to ensure that tissue temperature remains at safe levels. In addition NMR console 526 may be used to monitor the formation of eddy currents or other undesirable effects in patient 502. Computer system 528 has ultimate control over the entire system, including the system mode (hyperthermia/NMR).

Finally, entire apparatus 500 has a magnetic shielding 536. Shielding 536, of which only the leftmost portion is shown in this exploded view for reasons of clarity, prevents undesirable electrical emissions from radiating from integrated hyperthermia/diagnosis apparatus 500, and more precisely from arrangement 504 of coils that generate strong magnetic fields.

The invention is not limited to any specific apparatus. In fact, it further extends to a method for inducing transient hyperthermia in a pathogen target. The method includes the steps of generating a magnetic field and providing nanoparticle-sized MAEs. As described above, the MAEs exhibit a controlled response to the magnetic field that includes an inductive thermal response by the magnetic material and a controlled mechanical response dependent on the shape imposed on the MAE by the coating in which the magnetic material is embedded. The MAEs, are delivered to a region in which the pathogen target resides. Since the MAEs are provided with targeting moieties for specific binding with the pathogen target, a number of them undergo such binding. Meanwhile, some MAEs remain unbound or free.

The antimicrobial thermal treatment method involves magnetic nanoparticle RF ablation technology to destroy a pathogen target. There are two components of the treatment. The first component involves a suspension of magnetic nanoparticles, i.e., MAEs as described above, attached to targeting moieties specific for a pathogen target that are injected into the patient. The second component consists of an external apparatus, similar to a Magnetic Resonance Imaging device (MRI) of which two embodiments are described above. The apparatus delivers a high-intensity AMF to the magnetic nanoparticles or MAEs. Following exposure to the magnetic field, the nanoparticles rapidly increase in temperature, destroying the pathogen target to which they are attached.

To ensure adequate and safe heating requires that both the thermal and inflammatory response to the treatment applicator be monitored. Optimization and adaptation of the field generator parameters occur dynamically in response to nanoparticle heating. In addition, the present technology allows for selective targeting of regions of the body by "dragging" the magnetic particles or MAEs to regions of the body where the infection resides. This allows infections to be treated in hypoxic regions of the body with limited blood flow where anaerobic infections prefer to reside.

The fact that properly sized iron-oxide nanoparticles are rapidly taken up by the reticular endothelial system (RES) means that the particles and attached targeting moieties will be pulled into endothelial cells. Given the fact that various pathogens, including *Plasmodium* spp., *M. fermentans*, and *M. pneumoniae* hide within the endothelial cells to evade the host immune system, this provides a new way to treat these intra-cellular infections.

In addition, the technology is pathogen specific, reducing the risk of resistance with prophylactic treatment. Also, this technology is not likely to cause the destruction of beneficial bacteria.

Despite the fact that inductive heating may effectively heat deep regions of the body, unlike dielectric heating modalities, induction heating may cause electric "eddy" currents that may form on the surface of the skin of the host. As a result, "hot spots" may arise near the surface of the skin, burning the host. The intensity of such eddy currents will increase with the square of the radius of the radiated tissue. This restriction limits the total volume of tissue that can be practically targeted for treatment. It is due to this eddy current formation that it has thus been previously experimentally determined that the safe limit for magnetic field exposure of a 30 cm loop for 1 hour is $F \cdot H < 4.85 \times 10^8 (A/m \cdot s)$.

To overcome problems with eddy current formation, several modifications of the treatment are proposed. First, in certain embodiments, many small, discrete regions of the body will be targeted. Second, in certain embodiments, higher intensity magnetic fields may be applied if done over short periods of time—a "pulsed" treatment approach. Third, in certain embodiments, an auxiliary electrode or "eddy-current absorber" is placed on the surface of the host's body. Such eddy-current absorbers can help to effectively dissipate any eddy currents that may form.

In addition, magnetic nanoparticles or MAEs may have several limitations in vivo. First, globular filtration will clear <40 kDa (10 nm) particles while for larger particles reticular endothelial system (RES) uptake will occur. Second, eventually magnetic particles will be incorporated into the iron stores in the body in the form of hemoglobin and ferritin, which suggests the possibility of iron overdosing. Third, the iron content of the iron stores (like ferritin proteins) suggest the possibility that such proteins may experience joule heating along with the similarly sized magnetic nanoparticles. Fourth, it has been theoretically shown that the ambient temperature in isolated cells may not be capable of being adequately heated even with high magnetic field intensity and high particle density due to the high cell surface area to volume ratio. Sixth, although safe parenteral dosing has been shown at 2.6 mg/kg and 10 mg/kg, higher dosing has been recommended for adequate heating. Seventh, it has been shown that paramagnetic particles can accumulate in potentially hazardous "clusters". Each of these problems will be separately addressed.

First, in certain embodiments, in order for nanoparticle preparations to be permitted adequate time to reach a given pathogen in vivo, smaller particles, coated in various hydrophilic coatings and conjugated to monoclonal antibodies, are primarily chosen to avoid RES uptake. These various hydrophilic coatings including, but not limited to, PEG (polyethylene glycol), dextran or modified dextran coatings, avoid particle opsonization, slow macrophage uptake, and slow monocyte uptake. The conjugated targeting moiety (i.e. monoclonal antibody) forms a bond to a target epitope, preventing the attached nanoparticle from being removed.

Second, in certain embodiments, to avoid the potential of iron toxicity, targeting moieties (i.e. monoclonal antibodies) may be used to reduce dosing to safe levels as the use of, for example, antibody conjugates cause nanoparticles to accumulate on the OSP of the target pathogen over time. However, in hosts with hemochromatosis, where iron clearance is reduced, further delays in dosing schedules may be required.

Third, iron stores have no apparent paramagnetic properties and do not experience a hyperthermia phenomenon. Such experimental observations have been widely described in the literature.

Fourth, in certain embodiments, although it may not be possible to cause the ambient temperature of an entire target cell to sufficiently increase, it may be possible to increase the temperature of the outer cell wall using the "pulsed" delivery of a higher intensity, higher frequency magnetic field. In certain embodiments, a pulsed therapy with high intensity field strength and vapor bubble formation may be exploited for improved heating.

Fifth, in certain embodiments, reduced doses of MAEs may be adequate given the advent of monoclonal antibody conjugates or other targeting moieties. Previous studies have determined dosing requirements based upon the assumption that nanoparticles would be continuously removed from the blood stream. However, the antibody conjugates or other targeting moieties will remain bound to the target pathogen cells for long periods of time, during which the body is given a chance to clear unbound iron particles from the blood. Once iron levels have returned to safe levels, further parenteral dosing (or through other modes of administration) may be possible, causing nanoparticles bound to the epitope of pathogen cells to accumulate over time.

Sixth, in certain embodiments, to eliminate the potential for potentially harmful "cluster" formation, nanoparticle preparations are used, which do not exhibit magnetic dipoles in the absence of an externally applied magnetic field. Further, a "pulsed" treatment may reduce the time allowed for cluster formation to occur while the magnetic field is active.

Provided these limitations can be overcome, in certain embodiments it remains necessary that the transient temperature rise be sufficient to destroy the target pathogen. Limited data exists to show the relationship between the transient temperature of the outer surface protein of a target pathogen to the probability that a pathogen is destroyed. However, data has been published that shows a log-6 order destruction of MRSA occurs within several seconds at 55° C., which equates to an 18° C. transient increase in temperature.

Neutrophils function as the special forces of the immune system in that they are the first to arrive to injured tissue and are endowed with an impressive biochemical armamentarium to battle infection. A fine balance exists between their antibacterial and wound healing responses that is likened to a double-edged sword. At the initial phase of infection, efficient and rapid PMN recruitment to the site of infection is essential for successful bacteriocidal function. However, too much neutrophil recruitment and prolonged survival (e.g. delayed apoptosis) can result in delayed wound healing and an impaired endothelial barrier to leakage of plasma proteins. Neutrophils release pro-inflammatory cytokines and super oxide, which can serve to scavenge nitric oxide (NO) and promote tissue damage. As cellular sources of NO are important for successful wound repair, acute wounds that become infected can rapidly transform into chronic, non-healing wounds in the presence of persistent infection. While conventional treatments have relied on antibiotics for neutralizing chronic and systemic infections after they are detected, the innovation here is to direct therapy designed to rapidly mobilize the innate immune response locally within the wound in order to control bacterial burden associated with blast and burn wounds early and accelerate the natural healing process. With baseline parameters established in terms of increase number and activation state within wounds, the targeted application of anti-inflammatories within the wound at the right time and duration will provide novel insights into the most pertinent players in the balance between wound resolution and fulminate infection.

The ability for a magnetic nanoparticle to act as an MRI contrast agent is both a function of the particles small volume and its magnetic material. When the volume of a ferromagnetic particle decreases past a certain threshold, ambient thermal energy becomes sufficient to flip the electron spin direction of the particle in the absence of an externally applied magnetic field. Consequently, in the absence of an externally applied magnetic field, the particles magnetic dipole becomes randomized over a short period of time. In the presence of a magnetic field, a magnetic nanoparticles will align with the applied field. This phenomenon is known as superparamagnetism. Such magnetic nanoparticles are typically made of $Fe_2O_3$ (maghemite), $Fe_3O_4$ (magnetite), $MnFe_2O_4$, FePt, FeCo, Co or monocrystalline iron oxide.

In view of the above, it is important that the method of invention be implemented after reviewing these issues. The condition of the host, the type of pathogen target, the location and mobility of the target and other relevant parameters mentioned above should be taken into consideration when administering hyperthermia.

FIG. 9 is a block diagram that illustrates a methodology of an embodiment of the present invention. FIG. 9 illustrates the methodology for both diagnostic and treatment an infection using an embodiment of the present invention that makes use of an integrated NMR and RF hyperthermia device, analogous to the one described in FIG. 8, and MAEs whose pathogen target is a specific infection.

In step 901 MAEs are administered to a patient using any of the modes of administration described herein. In step 902 an MRI scan is performed using an integrated NMR/hyperthermia device. A computer algorithm measures the concentration of MAEs in tissue to determine if a sufficient number of MAEs have reached the infection site to allow a decision step 903. If an insufficient number of MAEs have reached the target site, a magnetic dipole will be computed to force or distribute MAEs to the infection site in step 904. The computer algorithm then directs the electromagnet and associated gradient coils to reorient a magnetic dipole to direct MAEs to the proper location in step 905.

Following a period of time, another MRI scan is performed in step 906 to determine if a sufficient number of MAEs are present for treatment. If an adequate number of MAEs are present at the target site, a period of time is allowed to elapse to permit bioconjugation and MAE tissue clearance of unbound MAEs during step 907. The amount of time allowed to elapse will vary from several minutes to days or weeks depending upon the site targeted for treatment.

Following this period of time, an MRI scan is performed in step 908. Then, in step 909 the location of pathogen targets and MAEs, as well as their temperatures are determined using MR thermometry and other thermal measurement methods (thermal camera etc). In step 910, the number and physical properties of the MAEs (bound/unbound) is determined and a decision is rendered. If a sufficient number of MAEs are not present, the algorithm proceeds to step 912. In this step diagnosis is deemed negative and treatment is halted. If a sufficient number of bound MAEs are present the algorithm proceeds to step 911. In this step diagnosis is considered positive a treatment is recommended.

Step 913 describes a startup sequence to initially configure the NMR/hyperthermia device for hyperthermia treatment. An AMF is applied to generate heating in sites where infection has been detected in step 914. Step 915 describes the use of NMR thermometry, and/or other thermal measurement methods (ie. IR cameras, thermoptic temperature probes etc) for the purpose of measuring the nanoparticle temperature. Based upon this new data, pathogen and MAE locations are determined again in step 916.

In step 917 the new location and temperature data is used to modify AMF pulse sequences and ensure maximum pathogen destruction without causing damage to patient cells through inflammatory response or steered thermal immunomodulation. Based upon thermal data, it is determined if pathogen threshold has been reached in step 918. If threshold has been reached (pathogen cell load sufficiently reduced), treatment is halted 919. Otherwise device parameters are recomputed in step 920 and another AMF pulse sequence is applied by returning to step 914.

FIG. 10 illustrates the overall operation of a control system of the present invention as may be implemented on a computer (e.g., a computer system as shown in apparatus 500 of FIG. 8). Control system 1001 will initially set AMF parameters for magnetic field generator 1002. Generator 1002 will apply magnetic field pulses that were programmed by control system 1001. This will induce MAE heat dissipation 1003 by the inductive thermal response, as discussed above.

NMR thermometry 1004 may be used for the purpose of measuring the MAE and/or surrounding tissue temperature of the region targeted for treatment. Heat absorbed by MAEs 1005 can also be measured by NMR thermometry 1004. In addition, heat absorbed by MAEs 1005 may be measured through other mechanisms including infrared cameras, optical probes, thermocouples, and the like. Control system 1001 will use inputs to modify AMF parameters to ensure pathogen destruction and treatment safety.

The MAEs of invention can also take on some still different shapes and exhibit controlled mechanical responses that enable them to contain the thermal energy due to the inductive thermal response of their magnetic material. FIGS. 11A-B illustrate an MAE 600 with several coatings 602, 604, 606. Of those, coating 604 embeds a magnetic material 608. In FIG. 11A material 608 is deposited in one piece, while in FIG. 11B it is deposited in the form of magnetic crystals 609.

In the both embodiments, coatings 602, 604, 606 confer on MAE 600 the shape of a shell 610. Targeting moieties 612 are attached to an inner face 614 of shell 610. In particular, their bonds keep them attached on the most inner coating 606. Thus, when during diagnosis or treatment targeting moieties 612 bond to antigens associated with the pathogen target, shell 610 will face the pathogen cell wall with its concave inner face. Such geometrical arrangement improves the delivery of thermal energy and keeps it directed predominantly toward the pathogen target.

Meanwhile, when MAE 600 is free or unbound, the controlled mechanical response of MAE 600 is a pinching of shell 610 inward. In other words, shell 610 will have a tendency to close, and thus help contain thermal energy and avoid collateral thermal damage to healthy tissue.

The advantageous pinching process can be aided, especially in the embodiment of MAE 600 in FIG. 11B, by choosing appropriate magnetic material 608 of crystals 609. For example, material 608 can be chosen to exhibit no magnetic effects when no static magnetic field is applied. Once the static magnetic field is applied, crystals 609 will exhibit magnetism. In this state, they will exhibit magnetic dipole-dipole coupling response to the external field. Thus, the magnetic dipole-dipole coupling between various regions of magnetic material 608, and preferably magnetic crystals 609 of magnetic material 608, will affect the controlled mechanical response such that in changes the shape of MAE 610. Specifically, this change will involve bending of MAE 610. When properly applied, this bending results in a pinching or closing of shell 610, thereby containing the inductive thermal response of magnetic material 608.

FIGS. 12A-B are cross-sectional views illustrating the attachment of targeting moieties to a coating and directly to the magnetic material of an MAE. Specifically, both drawings illustrate an MAE 700 that is hemispherical and whose magnetic material 702 is embedded in a core coating 704. MAE 700 also has an external coating 706. Together, coatings 704, 706 help to impose the hemispherical shape on MAE 700.

In the embodiment of FIG. 12A, a targeting moiety 708 in the form of an antibody is attached to core coating 704 with the aid of bond 710. In this situation, when material 702 produces thermal energy 712 during its inductive thermal response to an AMF, energy 712 tends to pass well through the thin layer of core coating 704. However, energy 712 does not tend to be conducted as well along the structure of targeting moiety 708.

The conduction of thermal energy 712 via targeting moiety 708 is improved in the embodiment of FIG. 12B. Here, targeting moiety 708 is attached directly to magnetic material 702. To this end, a passage 714 for targeting moiety 708 is provided through coating 702 to make direct contact with material 702. Of course, the attachment mechanism will have to be adapted, depending on the material. For example, sulphur bonds may be employed to bond targeting moiety 708 to the metal surface.

FIG. 13 illustrates an embodiment of another apparatus according to the present invention. A portable field generator 1104 is attached through an arm to treatment applicator 1103. Contained within treatment applicator 1103 is an induction heating coil 1101, flux concentrator 1102 that directs and concentrates the lines of magnetic flux to a region in front of applicator 1103. Coil 1101 may be designed with one or more turns in the form of a "pancake coil" or coils intended for heating of surfaces (i.e. surface hardening).

Inside field generator 1104 is a water tank 1107, which may be filled using a nozzle 1108. A refrigeration unit 1109 may be used for the purpose of cooling water in water tank 1107. A fluid pump 1114 may be used for the purpose of recirculating water through the inductive heating coil present in treatment applicator 1103.

Applicator 1103 contains and electrical transformer for the purpose of increasing or decreasing the voltage to be compatible with field generator 1104.

A power supply 1112 delivers power to applicator 1103 through circuit interconnects within the treatment arm. Unit 1105 contains computer electronics to support device operations. Unit 1106 contains a heat exchanger a fan to expel heat from the refrigeration unit. Not shown are electrical connections to a power outlet or digital interconnects between the portable field generator and computer console (not shown).

FIG. 14 illustrates an apparatus of the present invention for treating infected wounds. A patient 1207 is placed on a bed or table. The bed or table should not contain any substantial quantity of metal. Patient 1207 will not have any metal implants or other devices in the vicinity of the field generator applicator 1206.

A medical operator 1211 will move arm 1203 to orient applicator 1206 over a wound 1208 infected with pathogen 1209. The applicator 1206 should be very close to the surface of wound 1208, but may not come in direct contact with it. Operator 1211 will then interact with a computer 1202 via a console and a display 1201.

A preparation of MAEs is delivered to wound 1208 environment using one or more modes of administration as described herein. Following a period of time where the MAEs have been absorbed into wound 1208, operator 1211 interacts with computer 1202 to instruct that portable field generator 1210 be enabled. Following a period of time, operator 1211 will interact with computer 1202 to deactivate field generator 1210. Multiple treatments may be necessary for the complete eradication of pathogen cells 1209.

Applicator 1206 contains a capacitor bank 1205, which may be modified depending upon the region of body targeted for treatment. Unit 1204 is a thermal imaging camera, which interacts with field generator 1210 and, in turn, with computer 1202 for the purpose of optimizing treatment to ensure safety and efficacy.

Nanoparticle Synthesis

Nanoparticle Synthesis Mechanisms

Recent advances have led to the development of functional superparamagnetic nanoparticles that are covalently linked to biological molecules such as peptides, proteins, and nucleic acids. The magnetic nanoparticles used herein are preferably nontoxic, small enough to not generate an immune response, chemically stable, soluble in water, stable in solution, nontoxic, optionally biodegradable, and coated in such a way to delay RES uptake.

Previously commercially available nanoparticles include those used for various applications including cell sorting, magnetic resonance imaging and the like (Whitesides et. al., 1983; Sun et. al., 1983; Shafi et. al., 2001; Park et. al., 2000; Suslick et. al., 1996; Josephson et. al., 2001; de la Fuente et. al., 2001; Barrientos et. al., 2002; Hernaiz et. al, 2002). Nanoparticle preparations may also be obtained from Advanced Magnetic Pharmaceutical, Micromod Gmbh., Ocean Nanotech, Turbobeads, and others. Such nanoparticle preparations and tools for studying them have been previously disclosed (US WO/2003005029; US WO/20020068187; U.S. Pat. No. 6,254,662; U.S. Pat. No. 6,514,481; US WO/2002098364; US WO/200119405; US WO/2002073444; US WO/20020933140; U.S. Pat. No. 6,531,304; US WO/200232404; US WO/2006023712).

Methods of synthesizing nanoparticles preparations have included vapor deposition, mechanogrinding, microemulsion, sol-gel processes, and coprecipitation of ferrous and ferric salts. In addition, monodisperse MNP preparations can be produced using a non-hydrolytic synthetic approach using thermolysis. In particular, maghemite can be made using iron petacarbonyl as a molecular precursor in the presence of oleic acid. Uniform MNPs can be made in a range of 5-30 nm in diameter using this approach. Further, different chemical compositions, including iron, cobalt, magnetite, iron-platinum alloy and others, can be produced. Various shaped particles can also be produced. These include spheres, rods, cubes, and domes/shells. Internal structures can be created that permits the creation of a particle with a central core with one material, like iron, and surrounding shell of a different material, like magnetite.

Hydrophobic nanoparticles must be made water-soluble in order to deliver them to a host.

The first method is to replace the hydrophobic monolayer on the surface of the nanoparticles with hydrophilic ligands. One example is the creation of a cross-linked dextran coating, which coats the nanoparticles. These crosslinked iron oxide (CLIO) particles will have coatings with thicknesses that are typically 20 nm or more.

The second method is to retain the hydrophobic monolayer on the surface of the nanoparticles, and bind amphiphilic polymers to the outer surface of the particle. First, the surface of the nanoparticles is modified using various polymers, including octylamine-modified polyacrylic acid, PEG-derivatized phospholipids, block copolymers, and amphiphilic polyanhydrides. Second, amphiphilic polymers are applied to surface-modified nanoparticles. The amphiphilic polymer has both a hydrophobic region (made of hydrocarbons) that interacts with the alkyl chains of the ligands on the modified-nanoparticles surface and also a hydrophilic region (such as polyethylene glycol or multiple carboxylate groups) that faces outwards, away from the nanoparticles that renders the particle water-soluble.

This second method is the better method for various reasons. First, the surface coatings are smaller (2-5 nm) versus 20 nm or more for CLIOs. The smaller particles will permit higher iron mass to volume ratio, improving the rate of heating. Second, the biocompatibility of the nanoparticles made using the second method can be further improved by using biodegradable amphiphilic polymers to improve the safety profile of the particles. Specifically, every component of the modified nanoparticles, including the core material (iron oxide) particle surface ligands (oleic acid), and polymer coating (polyalkylacrylic acid and pluronic polymers) are biocompatible.

Once a hydrophilic particle is developed, the particle is then modified to resist uptake by the reticular endothelial system (RES). To do so, the outer hydrophilic coating of the particle is PEG-ylated by being bound with polyethylene glycol. PEG further improves biocompatibility and reduces non-specific binding of the particle.

Once a hydrophilic polymer-coated nanoparticle is developed that can resist RES uptake, binding the particle to a targeting moiety creates the binding specificity or targeting ability. This targeting moiety can include bioaffinity ligands such as monoclonal antibodies, peptides, oligonucleotides or small-molecule inhibitors. Further, multiple bioaffinity ligands can be conjugated to a single polymer-coated nanoparticle rendering a multivalent presentation of affinity tags and multifunctionality.

It is now apparent that magnetic nanoparticles are more effective T2 contrast agents than disperse iron solutions with the same iron concentration. This is due to the fact that magnetic nanoparticles are apparently better at dephasing the electron spin of water molecules surrounding the magnetic nanoparticles.

Bioconjugate Techniques (Germanson G, 2008), discloses various methodologies to synthesize various liposome preparations, including those containing metal cores (gold, silver, iron) and silica ($SiO_2$) shells. Except insofar as any synthesis methodology is incompatible with the coating of a nanoparticle shell with any liposome coating, enclosed herein, Bioconjugate Techniques (Germanson G, 2008) are contemplated for use with MAEs within the scope of this invention.

Conjugation Mechanisms

Ligand Conjugation Mechanisms

Multiple conjugation mechanisms may be used to bind the nanoparticle to a targeting moiety for the purpose of constructing a Magnetic Absorption Enhancer (MAE). The binding of the nanoparticle to the targeting moiety can occur extracorporally (outside the patient) or intracorporally (inside the host).

In general, the methodology to conjugate a nanoparticle to an affinity ligand includes activation, coupling, and washing. The coupling of the nanoparticles typically occurs through covalent coupling. Common functional groups or reactive groups on the particle surface used to bind to affinity ligands may include carboxylate, aldehyde, alphatic amine, hydroxyl, hydrazide, aromatic amine, thiol, epoxide, amide, chloromethyl, and may be tosyl-activated.

Particles with carboxylate groups on the outer surface can be bound to amine-containing affinity ligands using a number of strategies. The most common strategy for activation and coupling is a carbodiimide-mediated process using EDC (1-ethyl-3-(3-dimethylaminopropyl)carbodiimide). The coupling can either occur in a single step or in a two step process that makes use of N-hydroxysuccinimide (NHS) or sulfo-NHS. In this reaction, nanoparticles with carboxylate surface groups are activated using EDC to create an intermediate. This intermediate is an ester that can directly react with the amine of an affinity ligand. Alternatively, a higher yield reaction can occur through the addition of NHS or sulfo-NHS to EDC. NHS or sulfo-NHS react with the intermediate ester that was generated through the reaction of the surface carboxylate of the nanoparticle and EDC to generate a second intermediate NHS ester or sulfo-NHS ester, which then reacts with the amine of an affinity ligand.

This second method results in higher yields for two reasons. First, NHS ester or sulfo-NHS ester are more stable in solution than the intermediate using EDC alone, which increases yield. Second, the generation of an NHS or sulfo-NHS ester removes excess EDC before the addition of the affinity ligand, which prevents protein polymerization due to the presence of excess EDC.

Other methodologies to bind nanoparticles which amine functional surface groups include alkylation or acylation reactions, resulting in secondary or tertiary amine linkages or amide bonds. This occurs through addition or iodoacetyl-modified compounds, carboxylate-containing compounds with EDC, NHS ester activated compounds, oxidized glycoprotein or aldehyde-containing compounds with NaCNBH3, glytaraldehyde with NaCNBH3, or glutaraldehyde polymer.

Nanoparticles with amine functional surface groups can be bound to affinity ligands using N-succinimidyl 3-(2-pyridyldithio)propionate (SPDP) crosslinker coupling. The nanoparticle with amine surface groups is reacted with SPDP to form thiol-reactive pyridil disulfide groups. Then an affinity ligand with thiol group is added to form conjugation via disulfide bond, with pyridine 2-thione formed in an alternate reaction pathway.

Nanoparticles with amine functional surface groups can be bound to affinity ligands containing thiol groups by using heterobifunctional crosslinkers. A crosslinker that may be used is succinimidyl-4-(N-maleimidomethyl)cyclohexane-1-carboxylate (sulfo-SMCC). Another is using a NHS-$PEG_n$-maleimide reagent. In the latter case, a nanoparticle containing amine surface groups is reacted with NHS-$PEG_n$-Maleimide, creating thiol-reactive PEG-maleimides, which is then reacted with an affinity ligand containing thiol groups to form a thioether linkage between the nanoparticle and affinity ligand.

Nanoparticles with hydroxyl groups are coupled to affinity ligands using multiple methods. These may include addition of epichlorohydrin to form expoxides, addition of Divinyl sulfone to form vinyl sulfones, addition of cyanogen bromide (CNBr) to form cyanate esters, reaction with disuccinimidyl carbonate to form NHS-carbonates, reaction with carbonyldiimidazole (CDI) to form imidazole carbamates, reaction with 1,4-butanediol diglycidyl ether to form epoxides containing extended molecule arms, addition of Tresyl chloride to form tresylates, and addition of toxyl chloride to form tosylates. In each of these cases an affinity ligand with amine functional groups can be linked to the intermediate.

Nanoparticles with carboxylate surface groups or aldehyde groups can be reacted with EDC and carbohydrazide in excess to form hydrazide particles, which are then reacted with affinity ligands containing aldehydes and $NaCNBH_3$ to form a hydrazone bond. Nanoparticles with aldehyde groups can also be reacted with amine-containing affinity ligands to form a schiff base intermediate, which is then reacted with $NaCLBH_3$ to form a secondary amine linkage.

Nanoparticles with epoxide surface groups can be reacted with affinity ligands containing thiol, amine or hydroxide groups to form thioether bonds, secondary amine bonds, or ether bonds.

Nanoparticles with silica coatings can be reacted with 3-aminopropyltriethoxysilane (APTS) with $H_2O$ to form amine groups, which can then be can be bound to affinity ligands using N-succinimidyl 3-(2-pyridyldithio)propionate (SPDP) crosslinker coupling.

Particle washing can be done through centrifugation, gel filtration, size exclusion chromatography, membrane filtration, and/or tangential flow filtration. The decision about which method or combination of methods to use will largely be impacted based upon the size of the nanoparticle and ligand chosen for conjugation, the degree of hydrophilicity, and the surface charge of the nanoparticle. For example, if the nanoparticles are strongly hydrophilic, they will have a tendency to remain in solution, and if the particles have strong repulsive charge, they will resist a tendency to aggregate. If particles are strongly hydrophilic and have strong repulsive charge, centrifugation may be used to wash unbound ligand from nanoparticle conjugates following conjugation. These particles can typically be readily resuspended in solution following centrifugation using sonication by either using a sonic bath or sonic probe. However, centrifugation should not be used on particles that have a tendency to aggregate as they may become permanently aggregated and fall out of solution following centrifugation.

In addition, it is important to maintain proper solution characteristics to prevent nanoparticles from aggregating during the conjugation process. Typically this means maintaining proper pH, which maintains like charge repulsion among particles and prevents their aggregation and precipitation. For example, lowering the pH of a solution below the $pK_a$ of the particles on the outer surface of the particles (e.g. carboxyl group) either by impacting the buffer or salt composition of the suspension solution may result in protonation of these surface particles. The protonation may impact the negative charge on the particle (cause the charge to become more positive) and cause it to aggregate with another negatively charged particle forcing the particles out of solution.

Bioconjugate Techniques (Germanson G, 2008), in particular pages 582-626, discloses various methodologies to conjugate nanoparticle preparations, including metal (gold, silver, iron) and silica ($SiO_2$) to various ligands (glycoproteins, glycoprotein chains, antibodies, streptevidin, biotin). Except insofar as any conjugations technique is incompatible with the conjugation of a nanoparticle type, enclosed herein, to any ligand, enclosed herein, Bioconjugate Techniques (Germanson G, 2008) is contemplated to be proper to apply to any MAEs within the scope of this invention.

Nanoparticle Coating Synthesis

Nanoparticle Coating Mechanisms

Modification of the surface characteristics of the nanoparticle may be done through addition of polymers to the outer surface of the particle. This may be done to prevent RES uptake, prevent nonspecific interactions with other proteins or biomolecules, promote biocompatibility, promote hydrophilicity, and prevent particle aggregation. Examples of such coatings include poly(ethylene glycol) (PEG), poly(vinyl alcohol) (PVA), poly(acrylic acid), poly(methacrylic acid), poly(acrylamide), and poly(vinyl pyrrolidone). In addition, covalent attachment of hydrophilic spacer particles can modify the surface chemistry of an otherwise hydrophobic nanoparticle (ex made of $Fe_3O_4$) to become hydrophilic. A spacer which is commonly used is a poly(ethylene glycol) (PEG) chain which includes a hydrophobic linker that binds to the particle surface. The affinity ligands then bind to the end of the PEG chain, for example, through the use of a carboxylate group. It has been suggested that roughly 10% of the hydrophilic spacers end in a carboxylate group for attachment with affinity ligands, while the remaining 90% terminate in a PEG hydroxyl or PEG methyl ether group to maintain particle hydrophilicity.

Bioconjugate Techniques (Germanson G, 2008), discloses various methodologies to coat various nanoparticle preparations, including metal (gold, silver, iron) and silica ($SiO_2$). Except insofar as any coating methodology is incompatible with the coating of a nanoparticle type, enclosed herein, with any coating, enclosed herein, Bioconjugate Techniques (Germanson G, 2008) is contemplated to be applicable to any MAEs within the scope of this invention.

Delivery Mechanisms

Multiple administration mechanisms may be used to deliver the MAE to the infection site. This includes treatment within the patient or treatment outside of the patient.

In the case of treatment inside the patient, various delivery mechanisms for the MAEs may be employed. These methods include electroporation, microinjection, and the use of pharmaceutical compositions. Once delivered to the patient, dynamic or static application of magnetic fields may be used to assist in the delivery of MAEs to target regions of the body. Such regions could include, but are in no way limited to, extravascular spaces or ischemic regions with limited blood flow where an infection may reside.

In addition, the delivery of the magnetic nanoparticle and its targeting moiety may be separate. A target-specific ligand will be initially delivered to the patient. After a period of time is allowed to elapse when the target-specific ligand is permitted to bind to a target in vivo, a magnetic nanoparticle preparation is delivered to the patient. The nanoparticles of the preparation bind to the previously delivered target-specific ligand in vivo. An example of this is the use of a biotinylated ligand that is initially delivered to a patient, and then an avidin-bound magnetic nanoparticle that binds with the biotinylated ligand in vivo.

The separate delivery of the targeting moiety and the magnetic nanoparticle permits modification of dosing of one or the other. The intent of modifying such dosing may be, but is not limited to, increasing the safety of treatment by reducing levels of nanoparticle or targeting moiety to safe levels.

In addition, separate delivery of the targeting moiety and the magnetic nanoparticle permits the targeting ligand to foment an immune response and utilize immunotherapeutics prior to hyperthermia treatment. Other reasons for separate delivery could by to increase the effective sensitivity of the targeting moiety by increasing its concentration to improve hyperthermia efficacy by targeting a greater number of disease-material targets or to moderate hyperthermia treatment kill rate by reducing the binding sensitivity of the biotinylated ligand to the avidin-nanoparticle conjugate.

Electroporation is the use of an electric field to cells to enhance their uptake of various particles. This is well known to those expert in the art (Somiari et al., 2002, Mol. Ther. s:178; Nikoloff, A., Animal Cell Electroporation and Electrofusion Protocols, Methods in Molecular Biology, Vol. 48). Through a reversible disruption in the cellular membrane, foreign particles are allowed to enter the cell through the cell wall. Treatment parameters include electric field strength (V/m), duration, and number of field pulse(s). An exemplary embodiment of electroporation for the purpose of this invention is the use of electroporation to permit the passage of MAEs through the outer membrane of a target cell. This target cell could be a host cell to permit intracellular treatment of an infection or the target cell could be a pathogen cell in which the MAE targets an organelle of the pathogen. In addition, electroporation may be used to assist in the passage of MAEs through biofilms.

Microinjection is the delivery of a target entity physically to a host. Various automated microinjection apparatus have been separately disclosed (e.g. U.S. Pat. No. 5,976,826 and incorporated herein by reference). An exemplary embodiment of microinjection for the purpose of this invention is the use of microinjection to deliver the MAE to a target region of the host for treatment.

Pharmaceutically acceptable excipients include, but are not limited to, any solvents, dispersion media, diluents, other liquid vehicles, dispersion or suspension aids, surface active agents, isotonic agents, thickening or emulsifying agents, preservatives, solid binders, lubricants and the like as necessary for a particular dosage and formulation.

Pharmaceutically acceptable excipients include, but are not limited to, inert diluents, dispersing agents, granulating agents, surface active agents, surface active emulsifiers, disintegrating agents, binding agents, preservatives, buffering agents, lubricating agents, and lubricating oils. These excipients may include cocoa buffer, suppository waxes, coloring agents, coating agents, sweeteners (natural and synthetic), flavoring and perfuming agents.

Pharmaceutically acceptable diluents may include, but are not limited to, calcium carbonate, sodium carbonate, calcium phosphase, dicalcium phosphase, calcium solfate, calcium hydrogen phosphase, sodium phosphase lactose, sucrose, cellulose micro-crystalline cellulose, kaolin, mannitol, sorbitol, inositol, sodium chloride, dry starch, cornstarch, powdered sugar and combinations thereof.

Pharmaceutically acceptable granulating or dispersing agents may include, but are not limited to, potato starch, corn starch, tapioca starch, sodium starch glycolate, clays, alginic acid, guar gum, citrus pulp, agar, bentonite, cellulose and wood products, natural sponge, catin-exchange resins, calcium carbonate, sodium carbonate, crospovidone, sodium starch glycolate carboxymethyl cellulose, croscarmellose, methylcellulose, starch 1500, microcrystalline starch, water insoluble starch, calcium carboxymethyl cellulose, veegum, sodium lauryl sulfate, quaternary ammonium compounds and combinations thereof.

Pharmaceutically acceptable surface agents and emulsifiers may include, but are not limited to natural emulsifiers (acacia, agar, alginic acid, sodium alginate, tragacanth, chondrux, cholesterol, xanthan, pectin gelatin, egg yolk, casein, wool fat, wax, and lecithin), colloidal clays (bentonite, veegum, long chain amino acid derivatives, high molecular weight alcohols (stearyl alcohol, cetyl alcohol, oleylcocohol, triacetin monostearate, etylene glycol distearate, glyceryl monostearate, propylene glycol monostearate, and polyviny alcohol), carbomers (carboxy polymethylene, polyacrylic acid, acrylic acid polymer, and carboxyvinyl polymer), carrageenan, cellulosic derivatives (carboxymethyl-cellulose sodium, powdered cellulose, dydroxymethyl cellulose, hydroxypropyl celulose, hydroxypropyl cellulose, dydroxypropyl methylcellulose, methylcellulose), sorbitan fatty acid esters (polyoxyethylene sorbitan monolaurate, polyoxyethylene sorbitan, polyoxyethylenesorbitan monooleate, sorbitan monopalmitate, sorbitan monostearate, sorbitan tristearate, glyceryl monooleate, sorbitan monooleate), polyoxythylene esters (polyoxyethylene monostearate, polyoxyethylene hydrogenated castor oil, polyethoxylated castor oil, polyoxymethylene stearate, Solutol), sucrose fatty acid esters, polyethylene glycol fatty acid esters (Cremophor), polyoxyethylene ethers, (polyoxyethylene lauryl ether), poly (vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 1888, cetrimonium bromide, cetylpyridinium chloride, benzalkonium chloride, docusate sodium and combinations thereof.

Pharmaceutically acceptable binding agents may include, but are not limited to, starch (cornstarch and starch paste), gelatin, sugars (sucrose, glucose, dextrose, dextrin, molasses, lactose, lactitol, mannitol), natural and synthetic gums (acacia, sodium alginate, extract of Irish moss, panwar gum, ghatti gum, mucilage of isapol husks, carboxymethyl-cellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium alminum silicate, larch arbogalactan), alginates, polyethylene oxide, polyethylene glycol, inorganic calcium salts, silicic acid, polymethacrylates, waxes, water, alcohol and combinations thereof.

Pharmaceutically acceptable preservatives may include, but are not limited to, antioxidants (including, but not limited to, alpha tocopherol, ascorbic acid, acorbyl palmitate, cutylated hydroxyanisole, butylated hydroxytoluene, monothioglycerol, potassium metabisulfite, propionic acid propyl gallate, sodium ascorbate, sodium bisulfite, sodium metabisulfite, sodium sulfite, and combinations thereof), chelating agents (including, but not limited to, ethylenediaminetetraacetic acid (EDTA), citric acid monohydrate, disodium edatate, dipotassium edetate, edetic acid, fumaric acid, malic acid, phosphoric acid, sodium edetate, tartaric acid, trisodium edetate and combinations thereof), antimicrobial preservatives (including, but not limited to, benzalkonium chloride, benzethonium chloride, benzyl alcohol, cronopol, cetrimide, cetylpyridinium chloride, chlorhexidine, chlorobytanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, thimerosal and combinations thereof), antifungal preservatives (including, but not limited to, butyl paraben, methyl paraben, ethyl paraben, propyl paraben, benzoic acid, hydroxybenzoic acid, potassium benzoate, potassium sorbate, sodium benzoate, sodium propionate, sorbic acid, and combinations thereof), alcohol preservatives, acidic preservatives, and combinations thereof), alcohol preservatives (including, but not limited to, ethanol, polyethylene glycol, phenol, phenolic compounds, bispherol, chlorobutanol, hydroxybenzoate, phenylethyl alcohol, and combinations thereof), acidic preservatives (including, but not limited to, vitamin A, vitamin C, vitamin E, beta-carotene, citric acid, acetic acid, dehydroacetic acid, ascorbic acid, sorbic acid, phytic acid), and other preservatives (including, but not limited to, tocepherol, tocepherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenorip, methylparaben, Germall 115, Bermaben II, Neolone, Kathon, Euxyl and combinations thereof).

Pharmaceutically acceptable buffering agents may include, but are not limited to, citrate buffer solutions, acetate buffer solutions, phosphase buffer solutions, ammonium chloride, calcium carbonate, calcium chloride, calcium citrate, calcium glucionate, calcium gluceptate, calcium gluconate, D-gluconic acid, calcium glycerophosphate, calcium lactate, propanoic acid, calcium levulinate, pentanoic acid, dibasic calcium phosphase, phosphoric acid, tribasic calcium phosphase, calcium hydroxide phosphase, potassium acetate, potassium chloride, potassium gluconate, potassium mixtures, dibasic potassium phosphase, monobasic potassium phosphase, potassium phosphate mixtures, sodium acetate, sodium bicarbonate, sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol and combinations thereof.

Pharmaceutically acceptable lubricating agents may include, but are not limited to magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate and combinations thereof.

Pharmaceutically acceptable oils may include, but are not limited to, butylstearate, caprylic triglyceride, capric triglyceride, cyclomethicone, diethyl sebacate, dimethicone 360, isopropyl myristate, mineral oil, octyldodecanol, oleyl alcohol, silicone oil, almond, apricot kernel, avocado, babassu, bergamot, black current seed, borage, cade, mamomile, canolacaraway, carnuaba, castor, cinnamon, cocoa butter, coconut, cod liver, coffee, corn, cotton seed, emu, eucalyptus evening primrose, fish flaxseed, geraniol gourd, grape seed, hazel nut, hyssop, isopropyl myristate, jojoba, kukui nut, lavandin, lavender, lemon, litsea cubeba, macademic nut, mallow, mango seed, meadowfoam seed, mink, nutmeg, olive, orange, orange rought, palm, palm kernel, peach kernel, peanut, poppy seed, pumpkin seed, rapeseed, rice bran, rosemary, safflower, sandalwood, sasquana, savoury, sea buckthorn sesame, shea butter, silicone, soybean, sunflower, teatre, thistle, tsubaki, vetiver, walnut, wheat germ oils and combinations thereof.

Although the pharmaceutical compositions described herein are primarily for the purpose of human treatment, it will be appreciated by one who is skilled in the art, such as a Veterinary pharmacologist, that such compositions may be modified for the treatment of various non-human animals. Is it though the modification to formulations suitable for non-human animals that any host may be treated. Such hosts include, but are not limited to, humans, non-human primates, mammals, farm animals (cattle, pigs, horses, sheep), pets (cats, dogs, birds), poultry animals (chickens, ducks, geese, turkeys), and the like.

Pharmaceutical formulations described herein may be prepared by any who is skilled in the art of pharmacology. In general, any formulation may be derived by combining MAEs into association with an excipient and one or more accessory ingredients, and then, as necessary, formulating, packaging, shaping, or otherwise preparing a desired single-dose or multi-dose unit of drug for delivery. Such a dose is a discrete amount of the MAE composition that is added to excipients and accessory ingredients. The quantity of MAEs to be provided is dependent upon the specific host targeted for treatment. The composition may comprise between more than 0% and less than 100% (w/w) of the MAEs.

Using these preparations which include an active ingredient with optionally one or more excipients, one who is skilled in the art may prepare a pharmaceutical preparation intended for oral administration, parenteral administration, injectable administration, rectal administration, vaginal administration, topical administration, transdermal administration, pulmonary administration, intranasal administration, opthalmic administration, and otic (ear) administration. It may be necessary to delay or slow MAE absorption in the case of a preparation intended for any of these forms of administration. This may be accomplished by those knowledgeable in the art using multiple methodologies including, but not limited to, use of a material with poor water solubility (crystal or oil), using biodegradable matrices of the MAEs embedded in biodegradable polymers (polylactidepolyclycolide, polyethylene glycol, dextran, poly(orthoesters, poly(anhydrides), or using microemulsions and liposomes (including thermally sensitive lyposomes).

Preparations for oral administration may be in liquid or solid form.

Liquid preparations may include, but are not limited to pharmaceutically acceptable emulsions, microemulsions, solutions, suspensions, syrups, and elixirs. Such liquid forms may contain water or other solvents, solubilizing agents and emulsions (ethyl alcohol, isopropyl alcohol, ethyl carbonate, ethyl acetate, benzyl alcohol, benzyl benzoate, propylene glycol, 1,3-butylene glycol, dimethylformamide, oils (cottonseed oil, groundnut oil, corn oil, germ oil, olive oil, castor oil, sesame oil), glycerol, tetrahydrofurfuryl alcohol, polyethylene glycols and fatty acid esters or sorbitan and mixtures thereof, and adjuvants (wetting agents, emulsifying and suspending agents, sweetening, flavoring, perfuming agents).

Solid preparations may include, but are not limited to, capsules, tablets, pills, powders, and granules. Fillers may be used to bulk up the oral preparation and coatings and shells may be used, too. Acceptable excipients may include, but are not limited to, such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. acetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may further comprise buffering agents. Acceptable excipients to be used as fillers include, but are not limited to, lactose, milk sugar, high molecular weight polyethylene glycols, dextrates, dextrins, dextri-maltose, maltodextrin, pregelatinized starch, sodium starch glycolate, and the like. Such fillers can be derived from any starch source, including corn, potatoes, tapioca and wheat. Acceptable excipients for coatings and shells include, but are not limited to, any enteric coating (cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate, and stearic acid). Solid formulations may be designed to release part or all of the MAEs in a certain part of the intestinal tract. The release of the MAEs may optionally be in a delayed manner.

Liquid preparations intended for oral administration may include, but are not limited to, pharmaceutically acceptable emulsions, microemulsions, solutions, suspensions, syrups, and elixirs. Such liquid forms may contain water or other solvents, solubilizing agents and emulsions (ethyl alcohol, isopropyl alcohol, ethyl carbonate, ethyl acetate, benzyl alcohol, benzyl benzoate, propylene glycol, 1,3-butylene glycol, dimethylformamide, oils (cottonseed oil, groundnut oil, corn oil, germ oil, olive oil, castor oil, sesame oil), glycerol, tetrahydrofurfuryl alcohol, polyethylene glycols and fatty acid esters or sorbitan and mixtures thereof, and adjuvants (wetting agents, emulsifying and suspending agents, sweetening, flavoring, perfuming). For parenteral administration, liquid compositions may be mixed with solubilizing agents (Cremopho, alcohols, oils, modified oils, glycerls, polysorbates, cyclodextrine, polymers, and combinations thereof).

Preparations intended for parenteral administration may include, but are not limited to, pharmaceutically acceptable emulsions, microemulsions, solutions, suspensions, syrups, and elixirs. Such liquid forms may contain water or other solvents, solubilizing agents and emulsions (ethyl alcohol, isopropyl alcohol, ethyl carbonate, ethyl acetate, benzyl alcohol, benzyl benzoate, propylene glycol, 1,3-butylene glycol, dimethylformamide, oils (cottonseed oil, groundnut oil, corn oil, germ oil, olive oil, castor oil, sesame oil), glycerol, tetrahydrofurfuryl alcohol, polyethylene glycols and fatty acid esters or sorbitan and mixtures thereof, and adjuvants (wetting agents, emulsifying and suspending agents, sweetening, flavoring, perfuming). For parenteral administration, liquid compositions may be mixed with solubilizing agents (Cremopho, alcohols, oils, modified oils, glycerls, polysorbates, cyclodextrine, polymers and combinations thereof).

Preparations intended for injectable administration may include, but are not limited to, appropriate dispersing agents, wetting agents, and suspending agents. Such formulations may be sterilized, for example, by filtration through an appropriate filter or through the use of a sterilizing agent that may be dissolved or dispersed in a sterile injectable medium for use.

Preparations for rectal administration may include, but are not limited to, suppositories which can be prepared by mixing compositions with suitable non-irritating excipients such as cocoa butter, polyethylene glycol or a suppository wax which are solid at ambient temperature but liquid at body temperature.

Preparations intended for vaginal administration may include, but are not limited to, suppositories which can be prepared by mixing compositions with suitable non-irritating excipients such as cocoa butter, polyethylene glycol or a suppository wax which are solid at ambient temperature but liquid at body temperature.

Preparations intended for topical administration may include, but are not limited to ointments, pastes, salves, gels, powders, solutions, sprays, liniments, lotions, oil/water emulsions such as creams, and suspensions.

Preparations intended for transdermal administration may include, but are not limited to the use of transdermal patches. The rate of MAE delivery can may modified in the case of transdermal patches, for example, by modification of the patch membrane of gel excipient. Various mechanisms have been described elsewhere for intradermal delivery of pharmaceutical compositions, including needle-based devices (U.S. Pat. Nos. 4,886,499; 5,190,521; 5,328,483; 5,527,288; 4,270,537; 5,015,235; 5,141,496; and 5,417,662), liquid jet injectors (U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460), compressed air particle or powder guns, and conventional needles.

Preparations intended for pulmonary administration may be formulated as dry particles or liquid droplets. Dry particle formulations may include, but are not limited to, dry particles that comprise the MAEs that are added to a propellant (for example Dymel®134a/P and Dymel® 227ea/P) and optionally diluents and/or surfactants. The propellant/MAE preparation may then be inserted at variable pressures into a storage container. Liquid droplet formulations may include, but are not limited to, droplets of a solution that may be provided as an aqueous or dilute alcoholic solutions, which can be delivered using a nebulization or atomization device. Added to such droplet formulations can be, but is not limited to, flavoring agents, volatile oils, buffering agents, surface agents and preservatives.

Preparations intended for opthalmic administration may include, but are not limited to, eye drops containing a suspension of MAEs in a liquid excipient and optionally buffering agents, salts, and/or one or more other of the additional ingredients described herein.

Preparations intended for otic administration include, but are not limited to, ear drops containing a suspension of MAEs in a liquid excipient (for example Glycerin, Glycerol (E422); solutions of esters of 4-hydroxybenzoic acid in phenoxyethanol, Purified Water), and optionally buffering agents, salts, and/or one or more other of the additional ingredients described herein.

Modes of Administration

Compositions, according to the method of the present invention, may be administered to a subject using any amount and any route of administration effective for treating a disease, disorder, and/or condition. The exact amount required will vary from subject to subject, depending on the species, age, and general condition of the subject, the severity of the infection, the particular composition, its mode of administration, its mode of activity, and the like. Compositions in accordance with the invention are typically formulated in dosage unit form for ease of administration and uniformity of dosage.

The most appropriate route of administration will depend upon a variety of factors including the nature of the agent (e.g., its stability in the environment of the gastrointestinal tract), the condition of the patient (e.g. whether the patient is able to tolerate oral administration), etc. The invention encompasses the delivery of the pharmaceutical compositions by any appropriate route taking into consideration likely advances in the sciences of drug delivery. In certain embodiments, compositions in accordance with the invention may be administered parenterally at dosage levels sufficient to deliver a therapeutically effective dose to the patient.

TABLE 1

Pathogen, Indication, Antigen (Targets), and Example Antibodies

| Indication | Target(s) | Example Antibodies |
|---|---|---|
| RSV | Glycoprotein F | Palivizumab, MEDI-493 |
| Rabies | Glycoprotein antigenic site I, Glycoprotein antigenic site II, Glycoprotein antigenic site III, Glycoprotein minor site A | CR4098, CR 57, 17C7 |

TABLE 1-continued Pathogen, Indication, Antigen (Targets), and Example Antibodies

| Indication | Target(s) | Example Antibodies |
|---|---|---|
| WNV | Envelope protein, domain III | MGAWN1, CR4374 |
| SARS | S1-RBD | CR3014, CR3022 |
| CMV | Envelope glycoprotein gb | TI-23, HCMV37 |
| EBV | CD20 | Rituximab |
| VZV | Envelope glycoprotein III | TI-57 |
| HIV | Membrane proximal region (MPR) on gp41, MPR on gp41, Envelope glycoprotein gp 120 or envelope glycoprotein gp 41, gp160, RT, p17, p18, p19, p20, p21, p22, p23, p24, p24-p2p7p1p6, p2p7p1p6, Protease, Vpr, Nef, Integrase, Vif, Rev, Vpu, Tat, Env, HIV-1, TGFA, CD4, gp120-V3 tip, Aminophospholipids exposed on the surface of cells | CCR5, TNX-355, KD-247, PRO140, PRO542, HGS004, HGS101, Bavituximab |
| HCV | Envelope protein E2 | Bavituximab, AB68, AB65, HuMax-HepCl |
| Puumala hantavirus (PUUV) | Envelope glycoprotein G2, Envelope glycoprotein G1 | |
| Hantaan virus (HTNV) | Envelope glycoprotein G2, Envelope glycoprotein G1 | |
| SARS | Spike protein | |
| Ebola | GP | |
| WNV | DI/DII of E protein | |
| Yellow fever virus | Envelope protein E | |
| Hepatitis A virus (HAV) | Viral structure protein VP1, Viral structure protein VP3, Hepatitis A Antigen, VP4-VP2, 2322-2423 a.a. | |
| Hepatitis B virus | Pre-S1, Surface antigen (HBsAg), HBeAg | Ostavir |
| Hepatitis C virus | Envelope protein E2, Envelope protein E1, p22, Genotype 2a, HCV NS3, HCV NS4, Nucleocapsid (Core) 22 kDa | |
| VZV | Glycoprotein E | |
| Avian Influenza H5N1 | Hemagglutinin | |
| RSV | F protein | |
| Hendra (HeV) and Nipah virus (NiV) | Envelope glycoprotein | |
| Measles | Hemogglutinin (H) protein | |
| Parovirus | B19, Minor capsid protein VP1, major capsid protein VP2, nonstructural protein NS1 | |
| Vaccinia virus (B5) | Envelope B5 protein | |
| Vaccinia virus (A33) | Envelope A33 protein | |
| Rotavirus | Viral outer capsid protein 4 (VP4), Viral outer capsid protein 7 (VP7), CD4-binding site on gp120, Glycan cluster on gp120 | |
| *Babesia Microti* and *Duncani* | BMN1-2, BMN1-15, BMN1-17, MN-10, BMN1-17-MN-10, BMN1-17-4, BMN1-17-4, BMN1-17-11, BMN1-17-12, MN10-3, MN10-5, MN10-6, and MN10-8 | |
| HTLV-1 | Gp46 of HTLV-1 | |
| *Candida albicans* | 65?kDa mannoprotein (MP65), the secretory aspartyl Proteinase (SAP)2, Anti-β-glucan | |
| *Porphyromonas gingivalis* | | |
| Staph A | Autoinducing peptide (AIP)-4 | AP4-24 H11 |
| Staph A | Protein A, poly-N-acetyl glucosamine, GrfA (a staphylococcal ATP-binding cassette transporter protein), Capsular polysaccharide Type 5 and Type 8, ClfA, ClfB, FnBpA, FnBpB, CNa, GrfA, SdrE, IsdA, SdrD and IsdB, | mAb F598, te_bazumab, Pagibaximab, Veronate, Aurograb, 0657 nl (V710) |

TABLE 1-continued

Pathogen, Indication, Antigen (Targets), and Example Antibodies

| Indication | Target(s) | Example Antibodies |
|---|---|---|
| | PVL (Panton-Valentine Leukocidin), Alpha-Toxin (α-hemolysin) | |
| Transmissible spongiform encephalopathies (TSEs) | $PrP^C$, $PrP^{Sc}$, D18 epitope | |
| Prion | PrPSc | |
| *Bacillus anthracis* | protective antigen (PA, PA63), lethal factor (LF,), oedma factor (OF), anthrax toxin receptor (ATR1, ATR2, ATR3, TEM8/ATR) | raxibacumab, ETI-204, AIG, anthrax "plantibodies", AVP-21D9, MDX-1303, ToxBlox, Viprovex |
| *Clostridium botulinum* | toxoid A, toxoid B, toxoid E, HSV Core | anti-*Clostridium botulinum* A Toxoid, anti-*Clostridium botulinum* B Toxoid, anti-*Clostridium botulinum* E Toxoid |
| Salmon anemia virus | putative haemagglutinin of Infectious Salmon Anemia Virus (8-23 a.a.r., 296-312 a.a.r.) | |
| Rabies virus | rabies antigen, His-rNP, KL-CGVL | |
| *Clostridium tetani* | *clostridium tetani* toxin | |
| *Mycobacterium tuberculosis* | APA-antigen, RV2623, RV3134 | |
| *Borrelia burgdorferi* | Fla-p41, VlsE-IR6, OspA, OspB, OspC, OspD, OspE, OspF, BmpA, BmpB, BmpD, BlsE, BBK32, L25, LP6.6, P28, P23, P43.5, P35, P34, P31, P29, P28, P23, P22, P16.5, P15, P37, P7.5, P72, BbCsrA, BB0323, DbpA, BBK07, BB0184, bbk12, GroEL, Flagellin, FlaB, CspZ, ErpP, ErpA, ErpC, ErpX, bba74, TLR1-9, CRASP1, BmtA, EbfC, GuaA, GuaB, uPAR | |
| *M. pneumonia* | *M. pneumoniae* antigen | |
| *M. fermentans* | *M. fermentans* antigen | |
| *Haemobartonella* | *Haemobartonella* antigen | |
| *Pasmodium falciparum* | AMA-1 | |
| *Cryptococcus neoformans* | CneF | |
| *Cryptosporidium parvum* | CP15, CP60, P23 | |
| Enterovirus | enterovirus antigen | |
| Group A *streptococci* | SAN 0698, SAN 1485, SAN 1518, SAN 1577, SAN 1578, SAN 2207, SAN 0172, SAN 0480, SAN 0545, SAN 0785, SAN 1035, SAN 1460, SAN 1470, SAN 1666, SAN 0273, SAN 0710, SAN 0850, SAN 1534, SAN 1636, SAN 1898, SAN 2137, SAN 2224, SAN 0118, SAN 0317, SAN 0872, SAN 0970, SAN 1132, SAN 1449, SAN 1808, SAN 1319, SAN 1390, SAN 1012, SAN 1360, SAN 2424, PcsB protein, Gro, CAMP factor (CAMP-2), RplB, DivIVA, Tuf, Rbp, Fbp, C5a peptidase | |
| Measles virus | measles antigen | |
| Respiratory syncytial virus (RSV) | respiratory syncytial virus antigen | |
| *Streptococcus pneumoniae* | protein A | |
| Varicellazoster virus | | |
| Variola major | | |
| *Neisseria meningitidis* | | |
| Parvovirus | | |
| *Naegleria fowleri* | *naegleria* antigen | |
| *Ehrlichia* | | |

EXAMPLES

Example 1

Targeting Intestinal Parasites

Various infections, including *Enterobius vermicularis, Giardia lamblia, Ancylostoma duodenale, Necator americanus, Entamoeba histolytica*, and *Cryptosporidium* (*C. parvum, C. hominis, C. canis, C. felis, C. meleagridis*, and *C. muris*) are a serious risk to human health. Current treatments have severe limitations. These treatments include paromomycin, iodoquinol, diloxanide furoate, tetracycline, erythromycin, metronidazole, chloroquine, rifaximin, and nitazoxanide. Each suffers from specific limitations.

Problems with paromomycin include frequent GI disturbances, rare ototoxicity and nephrotoxicity, and high expense. Problems with iodoquinol include long treatment (20-day treatment course), drug contains iodine, rare optic neuritis, and atrophy with prolonged use. Problems with diloxanide furoate include the fact that it is only available from the CDC and can use severe GI disturbances. Problems with tetracycline and erythromycin include no activity for liver abscesses, frequent GI disturbances, the drug cannot be administered to children or pregnant women, and drug must be used with luminal agent. Problems with metronidazole, include anorexia, nausea, vomiting, and metallic taste in nearly one third of patients at dosages used, a disulfiram-like reaction with alcohol, and rare seizures. Problems with chloroquine include the fact that the drug is only useful for amebic liver abscess, occasional headache, pruritus, nausea, alopecia, myalgias, rare heart block, and irreversible retinal injury. Problems with rifaximin include the fact that it can only be used to treat a subset of infection and can cause substantial gastrointestinal distress and damage to beneficial micro flora. Problems with nitazoxanide include limitations regarding efficacy in HIV-infected or immunodeficient patients, and significant expense.

An MAE in accordance with the invention is chosen with an antibody that selects for the glycoprotein coat of one of *Enterobius vermicularis, Giardia lamblia, Ancylostoma duodenale, Necator americanus, Entamoeba histolytica*, and *Cryptosporidium* (*C. parvum, C. hominis, C. canis, C. felis, C. meleagridis*, and *C. muris*). The MAE may contain $Fe_3O_4$ or other magnetic material. An exemplary nanoparticle for the purpose of this example is Gastromark™ by Advanced Magnetic Pharmaceutical.

Delivery of the MAE may be oral using one or more excipients disclosed herein. The MAE shall be enteric coated to prevent damage of the targeting ligand due to stomach acids. The MAE shall be coated so as to prevent it from being absorbed through the intestinal lining.

Once swallowed, a period is time is allowed to elapse during which the enteric coating is biochemically removed, the targeting moiety is exposed, and the targeting moiety binds to the target pathogen. This period of time may be on the order of minutes to hours.

The patient shall then be placed into a magnetic field generator. An exemplary field generator is an Magnetic Resonance Imaging (MRI) diagnostic device which has been modified to permit hyperthermia treatment as described herein. The patient shall be exposed to an AMF of sufficient magnitude and frequency to induce heating of the MAEs within the patient. MR thermometry may be used during treatment to validate and adapt treatment (through a control system) to both enforce treatment safety and also to

Example 2

Using Hyperthermia to Perform Wound Debridement

In the case of treatment of a skin wound, nanoparticle hyperthermia may be simultaneously used to treat an infected wound and perform wound debridement. This could be done as an alternative to or in association with other forms of debridement (autolytic, enzymatic, mechanical, surgical, and using maggots).

In the case where wound debridement is desired, nanoparticles may be chosen with or without a targeting moiety that can be delivered to the wound environment. Delivery of the nanoparticles may be done either using a cream, sub-cutaneous injection and the like. Once applied, a period of time is allowed to elapse and the nanoparticles are allowed to disburse into the wound. This may be expedited using a magnetic field to evenly disburse the particles are described herein.

Once disbursed, the wound is exposed to an AMF that cause the nanoparticles to increase in temperature and denature necrotic tissue in and surrounding the wound. The thermal transient selected may be substantially less than that chosen for the purpose of treating an infection. In particular, the temperature is likely to be on the order of <45° C.

Example 3

Heating to Disrupt Biofilms or Prevent Biofilm Formation

Biofilms have been found to be involved in a wide variety of microbial infections in the body. Some estimates are that as much as 80% of all pathogens generate biofilms. Such biofilms substantially increase antimicrobial resistance and increase the ability of pathogens to persist, as antibodies cannot readily penetrate the biofilms. Several genetic regulation mechanisms have been implicated in biofilm regulation. These include quorum sensing and the novel secondary messenger cyclic-di-GMP.

These biofilms are implicated in urinary tract infections, catheter infections, middle-ear infections, formation of dental plaque, gingivitis, coating contact lenses, and less common but more lethal processes such as endocarditis, infections in cystic fibrosis, and infections of permanent indwelling devices such as joint prostheses and heart valves. More recently, it has been noted that bacterial biofilms may impair cutaneous wound healing and reduce topical antibacterial efficiency in healing or treating infected skin wounds. Pathogens that form biofilms include *Staphylococcus Aureus* (MSSA and MRSA), *Pseudomonas aeruginosa, Streptococcus* (*mutans, sanguis*, and others), *Legionella* (*pneumophila* and others), *Neisseria gonorrhoeae*, and others.

The biofilm is made up of an extracellular polymeric substance (EPS) or exopolysaccharide that binds the bacterial cells which make up the biofilm.

A particular use of the technology disclosed herein is for the purpose of disrupting biofilms or preventing their formation. This can be done through several mechanisms. First, MAEs may be used which target, bind, and ablate the exopolysaccharide that makes up the biofilm. Second, MAEs may be disbursed throughout the biofilm through the advent of a magnetic field. Third, an electric field may be used specifically for the purpose of heating the biofilms. Fourth, an electro-magnetic field may be used to heat metal fillings or other permanent indwelling devices (pins, joint prostheses, plates, stents) for the purpose of disrupting a biofilm that may have developed on their surface within the body.

Example 4

Target Bacterial Toxins for Ablation, Hyperthermia or Removal

Toxins released as the result of an infection may be targeted. Such toxins may include Tetanospasmin, Alpha toxin, Enterotoxin, Toxin A, Toxin B, Botoxin, Anthrax toxin, Listeriolysin O, Panton-Valentine leukocidin, *Staphylococcus aureus* alpha/beta/delta, Exfoliatin, Toxic shock syndrome toxin, SEB, Cord factor, Diphtheria toxin, Shiga toxin, Verotoxin/shiga-like toxin, *E. coli* heat-stable enterotoxin/enterotoxin, Cholera toxin, Pertussis toxi, *Pseudomonas* exotoxin, Extracellular adenylate cyclase, Superantigen, Pore forming toxins, AB toxin/AB5, Lipopolysaccharide, *Bacillus thuringiensis* delta endotoxin, Clumping factor A, Fibronectin binding protein A, A atoxin, Amatoxin (alpha-amanitin, beta-amanitin, gamma-amanitin, epsilon-amanitin), Citrinin, Cytochalasin, Ergotamine, Fumonisin (Fumonisin B1, Fumonisin B2), Gliotoxin, Ibotenic acid, Muscimol, Ochratoxin, Patulin, Sterigmatocystin, Trichothecene, Vomitoxin, Zeranol, and Zearalenone. The targeting and ablation or removal of such toxins may occur in accordance with the methodologies disclosed herein for the purpose of targeted ablation of infections and the like.

Example 5

Collagen Heating to Destroy Sequestered Pathogen

It has been previously shown that cells of *Borrelia burgdorferi* are able to persist following antimicrobial therapy (Barthold et al.). These so-called "persister cells" sequester themselves in collagen and evade host defenses and antimicrobial therapy. The mechanisms of evasion have been hypothesized to be due to insufficient blood flow to permit enervation of antibodies and antimicrobial compounds.

In addition, it has been shown that such "persister cells" are metabolically intact, but exist in a dormant or semi-dormant state. In this dormant state, such cells do not absorb extracellular molecules, including antimicrobial agents. This may be the mechanism by which antimicrobial agents (tetracyclines, cephalosporins) are rendered ineffective.

It has also been shown that *Borrelia burgdorferi* is a highly temperature sensitive organism (Schwartz et al). It has been shown that cells of *Borrelia burgdorferi* readily perish at over 40 C.

It is an exemplary use of the enclosed nanoparticle thermoablation technology to target *Borrelia burgdorferi* sequestered within collagen. This is made possible by engineering MAEs that target one or more surface antigens of the glycoprotein coat of *Borrelia burgdorferi*. These surface antigens include, but are not limited to, FIa-p41, VlsE-IR6, OspA, OspB, OspC, OspD, OspE, OspF, BmpA, BmpB, BmpD, BlsE, BBK32, L25, LP6.6, P28, P23, P43.5, P35, P34, P31, P29, P28, P23, P22, P16.5, P15, P37, P7.5, P72, BbCsrA, BB0323, DbpA, BBK07, BB0184, bbk12, GroEL, Flagellin, FlaB, CspZ, ErpP, ErpA, ErpC, ErpX, bba74, TLR1-9, CRASP1, BmtA, EbfC, GuaA, GuaB, and uPAR.

A parenteral or injectable suspension of MAEs will be delivered to a patient to target *Borrelia burgdorferi*. The patient will then be placed in a hyperthermia treatment device, and a methodology similar to that previously described herein will be used to diagnose and image the presence and location of infection. In particular, nanoparticles will be directed using magnetic fields to likely regions of infection (joints, spine, brain). Then, the patient will be told to return for treatment after a period of time (i.e., hours, days, or weeks). Once the patient returns for treatment, the patient will be exposed to an AMF of moderated intensity such that the nanoparticles rise above 40° C. In addition, it may be appreciated that such heating may be used simultaneously with antibiotic treatment (ie. I.V. ceftriaxone) to improve the efficacy of the antibiotic treatment through increased blood flow to the infection site.

Another embodiment of the present application for the purpose of treating *Borrelia burgdorferi* is to use an electric field to directly heat collagen. Electric fields have been shown to preferentially heat fats and collagen in lieu of other tissues. By exposing a patient to an electric field in the region where infection is suspected, "persister cells" may be able to be destroyed, clearing remnants of *Borrelia burgdorferi* infection from the patient. In addition, it may be appreciated that such heating may be used simultaneously with antibiotic treatment (ie. I.V. ceftriaxone) to improve the efficacy of the antibiotic treatment through increased blood flow to the infection site.

Example 6

MRSA Experiments

An application of this technology is to provide data on the effects of bacterial colonization and infection on the early kinetics of inflammation including phagocyte influx and vascular permeability in a real-time model of wound healing and will characterize how wound infection disrupts dynamic balance in endothelial barrier function to neutrophil influx and protein leakage and contribution to delayed wound healing. The specific therapeutic affect of bacterial killing at defined therapeutic values of nanoparticle dose and thermal activation may be independently varied and evaluated with respect to these parameters. The kinetic data may be compared between aseptic wounds and wounds inoculated to *S. aureus* in presence and absence of the nanoparticles over a range of concentrations. This may determine what combination of anti-inflammatories are the most effective at maintaining low infection and accelerating healing using an established wound healing model in mice and deliver new treatment protocols to reduce wound related infections and accelerate wound healing based on steered innate immune modulation. With baseline parameters established, the targeted application of nanoparticle therapy may provide novel insights into the most pertinent players in the balance between wound resolution and fulminant infection.

An application of this technology is to use targeted thermal immunomodulation to promote bacterial clearance and wound healing. The strategy is to establish treatment protocols that maximize targeting of wound related infections and accelerate antibiotic activity and wound healing through steered innate immune modulation.

First, antibodies that specifically identify the glycoprotein coat of MRSA are coupled to magnetic nanoparticles where binding is optimized in a 96 well plate based assay. Second, MAE nanoparticles and induction magnet parameters are optimized to thermally destroy MRSA in an established murine skin wound healing model in which MRSA is introduced. Inflammatory parameters including endothelial permeability, phagocyte recruitment, bacterial burden, and healing may be quantified using noninvasive whole animal imaging. Using animal wound healing models permits a quantitative approach to validating the nanoparticle targeted killing of MRSA through real time imaging of infection control and wound healing as a function of therapeutic strategy.

To target killing of *S. aureus*, monoclonal antibodies (or other targeting moieties) against bacterial surface components may be employed. This will allow direct particle contact with the surface of the *S. aureus* bacteria, which will facilitate antimicrobial thermal treatment using the magnetic nanoparticle RF ablation technology. There have been attempts to develop vaccines and passive immunization strategies to promote antibody-mediated responses against *S. aureus* in humans. For example, a conjugate vaccine that contains *S. aureus* type 5 and type 8 capsular polysaccharide (StaphVAX), a hyperimmune IgG preparation containing high titers of antibody against clumping factor A (ClfA) (Veronate), and a humanized monoclonal antibody directed against ClfA (tefibazumab) have all been tested in animals and humans, with disappointing success rates. The minimal response to these vaccines is likely due the multiple redundant mechanisms that *S. aureus* possesses to evade the hosts antibody-mediated phagocytosis response, including biofilm formation, phagocytic evasion, sequestration in extra-cellular matrix tissue, and the like. However, the use of magnetic nanoparticle hyperthermia may overcome many of these limitations.

To promote magnetic nanoparticle hyperthermia antimicrobial activity, we will target several *S. aureus*/MRSA cell surface antigens that are easily detected by circulating antibodies and do not require any uptake of the antibody into the bacterial cell. These candidate targets will include protein A, which is found on the capsule of all *S. aureus*/MRSA bacteria, and peptidoglycan and lipoteichoic acid, which are essential structural components of the cell wall of all *S. aureus*/MRSA bacteria. Protein A is considered an important virulence factor, since it binds the Fc portion of IgG, resulting in the binding of IgG in an incorrect orientation for detection by Fc receptors. Recent studies have demonstrated that a protein A vaccine strategy has some efficacy in preventing or controlling infection, demonstrating the feasibility of using protein A as a target for antimicrobial thermal treatment. There are commercially available mouse anti-protein A mAbs available that may be humanized to be used for this purpose (Abcam; clone 704 or clone SPA-27). In addition, *S. aureus* peptidoglycan and lipoteichoic acid are key structural components of the bacterial cell wall. By targeting these components directly, bacterial killing will be facilitated by not only heating the bacteria, but also in weakening of the cell wall. Mouse mAbs against peptidoglyccan (Abcam and ABR A_nity Bioreagents; clones Oct-34 and 10-34, respectively) and lipoteichoic acid (ABR A_nity Bioreagents; MA1-40134) are commercially available and may be humanized for this purpose.

Example 7

Nanoparticle Thermal Modeling

Preliminary temperature data have been collected through thermal computer simulations. These thermal simulations were an attempt to optimize the design of the field generator and nanoparticle conjugates. An optimal design is defined to be one that causes optimal destruction of the target pathogen while minimizing risk to the host.

In order to optimize the treatment, it is necessary to determine how the AMF frequency, AMF amplitude, nanoparticle radius, and nanoparticle tissue depth influence the transient thermal fluctuations within the nanoparticles and the surrounding tissue. To accomplish this, a transient electro-thermal model was built to explore these questions.

Nanoparticle heating occurs due to two forces acting upon each spherical magnetic particle. At steady-state, a magnetic nanoparticle experiences a force due to the externally applied magnetic field gradient and the friction of viscous drag against the fluid surrounding the particle. Therefore, the total power generation is a result of the combined effect of these two forces acting simultaneously on the particle. This power generation is described by the Neel and Brownian time constants, as has already been described above.

In our simulation, a single control volume is modeled corresponding to a region of human tissue. The tissue is modeled with reasonable approximations for blood flow. A single magnetic nanoparticle is placed in the center of the control volume. Power generation within the particle is modeled through Neel and Brownian effects, where the magnetic field amplitude is attenuated at the distance of the particle from the surface of the skin. The differential equation describing the transient temperature distribution within the control volume is fully described by the Pennes' equation, an equation commonly used to model biological bodies. The nanoparticle power density and maximum temperature rise is determined as a function of both magnetic field frequency and magnetic field amplitude.

Example 8

Diabetes Mellitus Treatment

An exemplary application of this technology is for the purpose of imaging and treatment of diabetic foot infections. There were 1.1 million new cases of diabetes mellitus (DM) in 2000, 140,000 hospital admissions for diabetic foot infection (DFI), and 81,000 lower extremity amputations (LEA) due to DM, resulting in greater than $1.1 billion in LEA-associated costs. Diabetic foot infections are polymicrobic, where *S. aureus* is the predominant aerobic species followed by *S. epidermidis*, *Streptococcus* spp., *P. aeruginosa*, *Enterococcus* spp. and coliform bacteria. Predominant anaerobic species are *Peptostreptococcus* spp. *Bacteroides* spp. and *prevotella* spp.

There is a lack of effective methods to diagnose and treatment DM. Diagnostic techniques include deep tissue techniques (biopsy and/or surgically debrided tissue) and surface sampling techniques. Imaging techniques include plain radiographs, TPBS, indium scan, TPBS/Indium Scan, MRI, and probe to bone. The sensitivity and specificity of such tests vary, costs can be prohibitive, and results are often of limited clinical relevance.

The density of microorganisms is a critical factor in determining whether a wound is likely to heal, and the presence of specific pathogens is of primary importance in delayed healing.

It has been shown that TNF-alpha blockers, commonly used in the treatment of psoriasis, Crohn's disease, ankylosing spondylitis, psoriatic arthritis, rheumatoid arthritis and ulcerative colitis may significantly increase the risk of infection in such patients. In particular, it was shown that patients undergoing treatment with infliximab have a 16.4 times greater risk of acquiring hospital-acquired tuberculosis than the general population.

As is clear from the above extensive teaching, the MAEs exhibiting a controlled response according to the invention, as well as the corresponding apparatus and method can be embodied in many ways. Therefore, the preceding is not to be construed as limiting on the invention. Rather, the scope of coverage is to be interpreted in view of the claims and all their legal equivalents.

I claim:

1. A nanoparticle-sized magnetic absorption enhancer exhibiting a controlled response to a magnetic field, said magnetic absorption enhancer comprising:
   a) a magnetic material having an inductive thermal response to said magnetic field;
   b) a coating embedding said magnetic material and conforming to a predetermined shape complementary to the shape of at least one other magnetic absorption enhancer, and producing a controlled mechanical response of said magnetic absorption enhancer to said magnetic field; and
   c) a targeting moiety for specific binding of said magnetic absorption enhancer to a pathogen target;
wherein said controlled response comprises said inductive thermal response and said controlled mechanical response comprising an interaction between said magnetic absorption enhancer and said at least one other magnetic absorption enhancer.

2. The magnetic absorption enhancer of claim 1, further comprising a flexible linker for binding said magnetic absorption enhancer to said at least one other magnetic absorption enhancer.

3. The magnetic absorption enhancer of claim 2, wherein said flexible linker is attached to said coating.

4. The magnetic absorption enhancer of claim 1, wherein said predetermined shape is selected from the group consisting of hemisphere, dome and shell.

5. The magnetic absorption enhancer of claim 4, wherein said magnetic material is distributed in a plurality of magnetic crystals embedded in said coating.

6. The magnetic absorption enhancer of claim 5, wherein each of said magnetic crystals comprises a single magnetic domain.

7. The magnetic absorption enhancer of claim 4, wherein said interaction of said magnetic absorption enhancer and said at least one other magnetic absorption enhancer forms a sphere for containing said inductive thermal response.

8. The magnetic absorption enhancer of claim 4, wherein said interaction of said magnetic absorption enhancer and said at least one other magnetic absorption enhancer forms a spherical shell for containing said inductive thermal response.

9. The magnetic absorption enhancer of claim 4, wherein said interaction of said magnetic absorption enhancer and said at least one other magnetic absorption enhancer forms a generally spherical dimer for containing said inductive thermal response.

10. The magnetic absorption enhancer of claim 4, wherein said predetermined shape is a shell, and said controlled mechanical response comprises a pinching of said shell for containing said inductive thermal response.

11. The magnetic absorption enhancer of claim 1, wherein said controlled mechanical response comprises a joining of said magnetic absorption enhancer with said at least one other magnetic absorption enhancer.

12. The magnetic absorption enhancer of claim 1, wherein said targeting moiety is in direct contact with said magnetic material.

13. The magnetic absorption enhancer of claim 12, wherein said coating has a passage for said targeting moiety to reach said magnetic material.

14. The magnetic absorption enhancer of claim 1, wherein said predetermined shape is a hemisphere and said targeting moiety is attached to the face of said hemisphere.

15. The magnetic absorption enhancer of claim 1, wherein said predetermined shape is a shell and said targeting moiety is attached to an inner face of said shell.

16. The magnetic absorption enhancer of claim 1, wherein said predetermined shape is a dome and said targeting moiety is attached to the inner portion of said dome.

17. The magnetic absorption enhancer of claim 1, wherein said targeting moiety is attached to said magnetic absorption enhancer by a bond.

18. The magnetic absorption enhancer of claim 17, wherein said bond is selected from the croup of bonding mechanisms consisting of passive absorption, covalent coupling, hydrogen bonding, secondary, or tertiary amine linkage, amide linkage, Schiff base linkage, isourea linkage, thiourea linkage, carbamate linkage, ether linkages, thioether linkages, strept(avidin)-biotin interactions, hydrazone linkages, SPDP crosslinker coupling.

19. The magnetic absorption enhancer of claim 1, wherein said coating comprises a bioccmpatible material.

20. The apparatus of claim 19, wherein said biocompatible material is selected from the group consisting of $SiO_2$, dextran, gold, silver and polyethylene glycol biodegradable polymers, modified dextran coatings, cross-linked dextran coatings, polylactide/polyglycolide copolymers, poly (orthoesters), poly(anhydrides), microemulsions, liposomes, and thermally sensitive lyposomes (LTSLs, HTSLs).

21. An apparatus for inducing transient hyperthermia in a pathogen target, said apparatus comprising:
   a) a means for generating a magnetic field;
   b) a nanoparticle-sized magnetic absorption enhancer exhibiting a controlled response to said magnetic field and comprising:
      i) a magnetic material having an inductive thermal response to said magnetic field;
      ii) a coating embedding said magnetic material and conforming to a predetermined shape, thereby producing a controlled mechanical response of said magnetic absorption enhancer to said magnetic field; and
      iii) a targeting moiety for specific binding of said magnetic absorption enhancer to a pathogen target;
wherein said controlled response comprises said inductive thermal response and said controlled mechanical response comprises an interaction of said magnetic absorption enhancer with at least one other magnetic absorption enhancer to form a geometrical arrangement for containing said inductive thermal response.

22. The apparatus of claim 21, wherein said means for generating said magnetic field comprise NMR coils and said magnetic field comprises an alternating magnetic field.

23. The apparatus of claim 21, wherein said controlled mechanical response comprises a change in said predetermined shape.

24. The apparatus of claim 23, wherein said change comprises a bending of said magnetic absorption enhancer when said magnetic field is being generated.

* * * * *